(12) United States Patent
Takaoki et al.

(10) Patent No.: US 6,586,356 B2
(45) Date of Patent: Jul. 1, 2003

(54) CATALYST COMPONENT FOR ADDITION POLYMERIZATION, CATALYST FOR ADDITION POLYMERIZATION, AND PROCESS FOR PRODUCING ADDITION POLYMER

(75) Inventors: Kazuo Takaoki, Ichihara (JP); Tatsuya Miyatake, Ichihara (JP)

(73) Assignee: Sumitomo Chemical Company, Limited, Osaka (JP)

( * ) Notice: Subject to any disclaimer, the term of this patent is extended or adjusted under 35 U.S.C. 154(b) by 126 days.

(21) Appl. No.: 09/741,173

(22) Filed: Dec. 21, 2000

(65) Prior Publication Data

US 2001/0020075 A1 Sep. 6, 2001

(30) Foreign Application Priority Data

| Dec. 27, 1999 | (JP) | ............................................ | 11-370685 |
| Dec. 27, 1999 | (JP) | ............................................ | 11-370686 |
| Dec. 27, 1999 | (JP) | ............................................ | 11-370687 |
| Dec. 27, 1999 | (JP) | ............................................ | 11-370688 |
| Mar. 22, 2000 | (JP) | ........................................ | 2000-080005 |

(51) Int. Cl.$^7$ ............................. B01J 31/38; C08F 4/44
(52) U.S. Cl. ......................... 502/155; 526/161; 526/171
(58) Field of Search ............................... 526/161, 170, 526/89, 171, 172; 502/152, 155, 104

(56) References Cited

U.S. PATENT DOCUMENTS

| 3,305,579 A | 2/1967 | Stadler et al. |
| 3,439,048 A | 4/1969 | Biller et al. |
| 3,810,952 A | 5/1974 | Durand et al. |
| 3,975,416 A | 8/1976 | Mazdiyasni et al. |

FOREIGN PATENT DOCUMENTS

| EP | 0 331 117 A1 | | 9/1989 |
| EP | 0 758 563 A1 | * | 2/1997 |
| EP | 0 758 593 A1 | * | 2/1997 |
| EP | 0 985 673 A2 | | 3/2000 |
| GB | 873226 | | 7/1961 |
| JP | 11279216 A | | 10/1999 |
| WO | WO 99/30819 | * | 6/1999 |
| WO | WO 99/51610 | | 10/1999 |

OTHER PUBLICATIONS

J. Chem.Soc. (A), G.E.Coates et al., 1966, pp. 1064–1069.
J. Amer. Chem.Soc.,89:1, Jan. 4, 1967; Hisaya Tani et al.
Chem.Ber.100, Peter Sartori et al., pp. 3016–3023, 1967.
J.Am.Chem.Soc., 90:20, Sep. 25, 1968; Wolfgang H. Eisenhuth et al.
J.of Organometallic Chem., J.G. Noltes, 12, pp.425–431, 1968.
J.of Organometallic Chem., J. Boersma et al., 13 (1968), pp. 291–299.
Angew.Chem.internatl.Ed., vol. 9, (1970), No. 11; pp. 905–906; M.F. Ziegler et al.
J.Polymer Science, vol. 11 (1973) pp.573–586; Nobuki Oguni et al.
J.of Applied Polymer Science, vol. 17, (1973), pp.1327–1338; Raff et al.
J.of Organometallic Chem., vol. 263 (1984), pp 1–7; Kuran et al.
Inorg.Chem., vol. 25 (1986); pp.1803–1805; Geerts et al.
J.Am.Chem.Soc., vol. 113 (1991), pp.3379–3385; Olmstead et al.
Acta Cryst.,C48 (1992) ,pp.641–644, Parvez et al.
J.Organometallic Chem., vol.430 (1992), pp.C33–C38; Herrmann et al.
Inorg.Chem.,vol. 32 (1993), pp.532–537; M. Bochmann et al.
J.Org.Chem.,vol. 59 (1994), pp.217–221; T. Ohkuma et al.
J.of Polymer Science:PartA:Polymer Chemistry; vol. 33 (1995) ,pp.1169–1176; A. Taquet et al.
Macromolecules, vol.28 (1995) ; pp.7577–7579; D.J.Darensbourgh et al.
J. Chem.Soc.,Dalton Trans., (1999), pp.1993–1997; J.T. Sampanthar et al.
Chemistry Letters, (1999), pp. 825–826.
J. Am.Chem.Soc., vol. 121 (1999), pp.107–116; D.J. Darensbourgh et al.
Boersma et al., J. of Organometallic Chemistry, vol. 81, p. 7–15, (1974).
Kuran et al., J. Macromol. Sci.–Chem., vol. A15(8), p. 1567–1575, (1981).
Boersma et al., Recl. Trav. Chim. Pays–Bas, vol. 92, p. 229–236 (1973).
Noltes et al., J. of Organometallic Chemistry, vol. 12, p. 425–431, (1968).
Amor et al., J. of Organometallic Chemistry, vol. 485, p. 153–160, (1995).
Acemoglu et al., Journal of Controlled Release, vol. 49, p. 263–276, (1997).
Ewart et al., J. of Organometallic Chemistry, vol. 579, p. 106–113, (1999).
Kimura et al., Chemical Abstracts, vol. 90, No. 14, (1979).
Tanaka et al., Chemical Abstracts, vol. 123, No. 12, (1995).
Okane et al., Chemical Abstracts, vol. 131, No. 20, (1999).

(List continued on next page.)

*Primary Examiner*—Robert D. Harlan
(74) *Attorney, Agent, or Firm*—Birch, Stewart, Kolasch & Birch, LLP

(57) ABSTRACT

An electron-withdrawing group-containing metal compound (I) of an atom of the Group III to the Group XII or lanthanide series of the Periodic Table of the Elements, a catalyst component for addition polymerization composed of the compound (I), a catalyst for addition polymerization obtained by contacting the compound (I) with a specific compound (II) of metal of the Group III to the Group XIII or lanthanide series and optionally an organoaluminum compound (III), and a process for producing an addition polymer using the catalyst.

11 Claims, No Drawings

OTHER PUBLICATIONS

Ewart, Sean W. et al., "Ethylene and propylene polymerization by cationic monocyclopentadienyl titanium catalysts containing the weakly coordinating anion 'B (C6F5) 4–", J.of Organometallic Chemistry (1999), 579, pp. 106–113.

Amor, J.I.et al., "Synthesis and characterization of new alkoxide and aryloxide derivatives of titanium and zirconium. X–ray molecular structure of 'ZrCp2 (OC6F5) 2"; J. of Organometallic Chemistry (1995), 485, pp. 153–160.

Deng et al., Macromol. Chem. Phys. vol. 196, pp. 1971–1980, (1995).

Takeshi et al., Macromol. Chem. Phys., vol. 199(8). pp. 1573–1579 (1998), (abstract only).

Gorecki et al., J. Organomet. Chem., vol. 312(1), pp. 1–11, (1986), (abstract only).

* cited by examiner

CATALYST COMPONENT FOR ADDITION POLYMERIZATION, CATALYST FOR ADDITION POLYMERIZATION, AND PROCESS FOR PRODUCING ADDITION POLYMER

BACKGROUND OF THE INVENTION

1. Field of the Invention

The present invention relates to a catalyst component for addition polymerization, a catalyst for addition polymerization made by using thereof, and a process for producing an addition polymer.

2. Description of Related Arts

Since olefin polymers such as polypropylene and polyethylene are excellent in mechanical properties, chemical resistance and the like and excellent in balance between those properties and economical efficiency, they have been widely used for various molding fields. These olefin polymers have been conventionally produced by polymerizing an olefin using a conventional type solid catalyst (multi-site catalyst) which combines a solid catalyst component obtained by using a metal compound of Group IV such as titanium trichloride or titanium tetrachloride, with a metal compound of Group XIII represented by an organoaluminum compound.

A process for producing an addition polymer, which polymerizes an addition-polymerizable monomer using a so-called single site catalyst prepared by combining a transition metal compound which is different from a solid catalyst component having been used from old (for example, a metallocene complex) with an aluminoxane or the like, is recently proposed. For example, JP-A-58-19309 reports a process using bis(cyclopentadienyl) zirconium dichloride and methyl aluminoxane. Further, it is reported that a specific boron compound and such transition metal compound are combined. For example, JP-A-1-50203 reports a process using bis(cyclopentadienyl)zirconium dimethyl and tri(n-butyl)ammonium tetrakis(pentafluorophenyl)borate. The olefin polymers obtained by using these single site catalysts have a narrower molecular weight distribution than that obtained by the conventional type solid catalyst (multi-site catalyst), and further, a comonomer is more homogeneously copolymerized in case of a copolymer. Accordingly, it is known that a more homogeneous copolymer than a case of using the conventional type solid catalyst is obtained.

The improvement of such catalyst component for addition polymerization has been intensively studied, and the kinds of metals used for main catalyst components are widely reported over the respective Groups of the Periodic Table. For example, in Angew. Chem. Int. Ed. 38 428 (1999), it reported that a metallocene complex of the Group III to the Group XIII and non-metallocene compound are effective as the main catalyst components. On the other hand, as a co-catalyst component as an activator for combining with the metallocene complex or non-metallocene compound, an aluminoxane belonging to a compound of the Group XIII, a boron compound and the like have been mainly developed.

Further, when an addition polymer such as an olefin polymer is produced using a single-site catalyst, the molecular weight of the addition polymer obtained is usually low, and the improvement thereof has been desired. JP-A-6-329713 reports a catalyst component of polymerizing an olefin composed of an aluminum compound having an electron withdrawing group or a group containing an electron withdrawing group. An olefin polymer having a certain degree of high molecular weight can be obtained by using the aluminum compound. However, since it cannot be always said that the high molecular weight is adequately high, a novel catalyst component as an activator, which realizes the further improvement of high molecular weight, has been desired.

SUMMARY OF THE INVENTION

An object of the present invention is to provide a compound capable of forming a catalyst for addition polymerization which reveals a high polymerization activity by using as a catalyst aid component for activation and a production method thereof, a catalyst component for addition polymerization composed of a compound, capable of forming a catalyst for addition polymerization which reveals a high polymerization activity, a catalyst for addition polymerization which is made by using the catalyst component and reveals a high polymerization activity, and an efficient process for producing an addition polymer using the catalyst for addition polymerization.

Namely, according to the present invention, an electron withdrawing group-containing metal compound (I) selected from the group consisting of [A] to [E] described below, a catalyst component for addition polymerization composed of the compound(I), a catalyst for addition polymerization prepared by contacting a transition metal complex (II) therewith or by contacting a transition metal complex (II) and an organoaluminum compound(III) therewith, and a process for producing an addition polymer with the catalyst for addition polymerization are provided:

[A] A compound obtained by contacting (a), (b) and (c) described below in the presence of an ether compound as a solvent:

(a) a compound represented by the general formula [1], $$M^1L^1{}_c \quad [1]$$

(b) a compound represented by the general formula [2], $$R^1{}_{p-1}T^1H \quad [2], \text{ and}$$

(c) a compound represented by the general formula [3], $$R^2{}_{q-2}J^1H_2 \quad [3]$$

(wherein in each of the general formulae [1] to [3], $M^1$ represents an atom of the Group III to the Group XII or lanthanide series of the Periodic Table; c represents a valence of $M^1$; $L^1$ represents a hydrogen atom, a halogen atom or a hydrocarbon group; when a plural number of $L^1$'s exist, they may be mutually the same or different; $R^1$ represents an electron-withdrawing group or a group containing an electron-withdrawing group; $R^2$ represents a hydrocarbon group or a halogenated hydrocarbon group; when a plural number of $R^2$'s exist, they may be mutually the same or different; each of $T^1$ and $J^1$ independently represents an atom of Group XV or Group XVI of the Periodic Table; and each of p and q represents a valence of $T^1$ and $J^1$, respectively.);

[B] A compound obtained by contacting (d), (e) and (f) described below:

(d) a compound represented by the general formula [4], $$M^2L^2{}_d \quad [4]$$

(e) a compound represented by the general formula [5], $$R^3{}_{r-1}T^2H \quad [5], \text{ and}$$

(f) a compound represented by the general formula [6];

(wherein in each of the general formulae [4] to [6], $M^2$ represents an atom of Group III to Group XII or lanthanide series of the Periodic Table; d represents a valence of $M^2$; $L^2$ represents a hydrogen atom, a halogen atom or a hydrocarbon group; when a plural number of $L^2$'s exist, they may be mutually the same or different; $R^3$ represents an electron-withdrawing group or a group containing an electron-withdrawing group; $R^4$ represents an organic group having a valence of f; each of $T^2$ and $J^2$ independently represents an atom of the Group XV or Group XVI of the Periodic Table; r represents a valence of $T^2$; e represents a valence of $J^2$; and "f" is an integer of 2 to 10.);

[C] A compound represented by the general formula [7]:

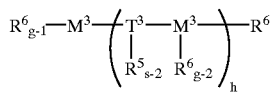

(wherein $M^3$ represents an atom of the Group III to Group XII or lanthanide series of the Periodic Table; when a plural number of $M^3$'s exist, they may be mutually the same or different; $T^3$ represents an atom of the Group XIV, Group XV or Group XVI of the Periodic Table; when a plural number of $T^3$'s exist, they may be mutually the same or different; $R^5$ represents an electron-withdrawing group or a group containing an electron-withdrawing group; when a plural number of $R^5$'s exist, they may be mutually the same or different; $R^6$ represents a hydrocarbon group; a plural number of $R^6$'s may be mutually the same or different; "g" represents a valence of $M^3$; "s" represents a valence of $T^3$; and "h" represents a numeral of 1 or more.);

[D] A compound represented by the general formula [8],

(wherein $M^4$ represents an atom of the Group III to Group XII or lanthanide series of the Periodic Table; $X^1$ represents an atom of the Group XIV, Group XV or Group XVI of the Periodic Table; when a plural number of $X^1$'s exist, they may be mutually the same or different; $R^7$ represents an electron-withdrawing group or a group containing an electron-withdrawing group; when a plural number of $R^7$'s exist, they may be mutually the same or different; $R^8$ represents a hydrogen atom, a halogen atom or a hydrocarbon group; a plural number of $R^8$'s may be mutually the same or different; "j" represents a valence of $M^4$; "t" represents a numeral satisfying $0<t\leq j$; and "i" represents a numeral less by one than the valence of $X^1$); and

[E] A compound represented by the general formula [9]:

(wherein $M^5$ represents an atom of the Group III to Group XII or lanthanide series of the Periodic Table; when a plural number of $M^5$'s exist, they may be mutually the same or different; $X^2$ represents an atom of the Group XIV, Group XV or Group XVI of the Periodic Table; when a plural number of $X^2$'s exist, they may be mutually the same or different; $R^9$ represents an electron-withdrawing group or a group containing an electron-withdrawing group; when a plural number of $R^9$'s exist, they may be mutually the same or different; $T^4$ represents an atom of the Group XIII of the Periodic Table, $R^{10}$ represents a hydrogen atom, a halogen atom or a hydrocarbon group; when a plural number of $R^{10}$'s exist, they may be mutually the same or different; "k" represents a valence of $M^5$; "u" represents a valence of $X^2$; and "m" represents a numeral satisfying $1\leq m\leq 3$.)

Further, the present invention is illustrated in detail below.

DETAILED DESCRIPTION OF THE INVENTION

Respective $M^1$ to $M^5$ in the general formulae [1], [4], [7], [8] and [9] represent an atom of the Group III to the Group XII or lanthanide series of the Periodic Table of the Elements (Revised edition of IUPAC Inorganic Chemistry Nomenclature 1989). Specific examples thereof include a scandium atom, an yttrium atom, a titanium atom, a zirconium atom, a vanadium atom, a chromium atom, a molybdenum atom, a manganese atom, a rhenium atom, an iron atom, a ruthenium atom, a cobalt atom, a rhodium atom, a nickel atom, a palladium atom, a platinum atom, a copper atom, a silver atom, a gold atom, a zinc atom, a cadmium atom, a mercury atom, a samarium atom, an ytterbium atom and the like. As $M^1$ to $M^5$, an atom of the Group XII is preferable in particular, and a zinc atom is most preferable.

Respective c, d, g, j and k in the general formulae [1], [4], [7], [8] and [9] represent a valence of Ml to $M^5$, respectively, and for example, when $M^1$ is a zinc atom, c is 2.

Respective $L^1$ and $L^2$ in the general formulae [1] and [4] represent a hydrogen atom, a halogen atom or a hydrocarbon group, and when a plural number of $L^1$'s and $L^2$'s exist, they may be mutually the same or different. Specific examples of the halogen atom in $L^1$ and $L^2$ include a fluorine atom, a chlorine atom, a bromine atom, and an iodine atom. As a hydrocarbon group in Ll and L2, an alkyl group, an aryl group or an aralkyl group is preferable.

As the alkyl group, an alkyl group having 1 to 20 carbon atoms is preferable. Examples include thereof a methyl group, an ethyl group, a n-propyl group, an isopropyl group, a n-butyl group, a sec-butyl group, a tert-butyl group, an isobutyl group, a n-pentyl group, a neopentyl group, a n-hexyl group, a n-octyl group, a n-decyl group, a n-dodecyl group, a n-pentadecyl group, a n-eicosyl group, and the like. A methyl group, an ethyl group, an isopropyl group, a tert-butyl group or an isobutyl group is more preferable.

Any one of these alkyl groups may be substituted with a halogen atom such as a fluorine atom, a chlorine atom, a bromine atom, or an iodine atom. Examples of the alkyl group having 1 to 20 carbon atoms which is substituted with the halogen atom include a fluoromethyl group, a difluoromethyl group, a trifluoromethyl group, a chloromethyl group, a dichloromethyl group, a trichloromethyl group, a bromomethyl group, a dibromomethyl group, a tribromomethyl group, an iodomethyl group, a diiodomethyl group, a triiodomethyl group, a fluoroethyl group, a difluoroethyl group, a trifluoroethyl group, a tetrafluoroethyl group, a pentafluoroethyl group, a chloroethyl group, a dichloroethyl group, a trichloroethyl group, a tetrachloroethyl group, a pentachloroethyl group, a bromoethyl group, a dibromoethyl group, a tribromoethyl group, a tetrabromoethyl group, a pentabromoethyl group, a perfluoropropyl group, a perfluorobutyl group, a perfluoropentyl group, a perfluorohexyl group, a perfluorooctyl group, a perfluorododecyl group, a perfluoropentadecyl group, a perfluoroeicosyl group, a perchloropropyl group, a perchlorobutyl group, a perchloropentyl group, a perchlorohexyl group, a perchlorooctyl group, a perchlorododecyl group, a perchloropentadecyl group, a perchloroeicosyl group, a perbromopropyl group, a perbromobutyl group, a perbromopentyl group, a perbromohexyl group, a perbromooctyl group, a perbromododecyl group, a perbromopentadecyl group, a perbromoeicosyl group and the like.

Further, these alkyl groups may be partially substituted with an alkoxy group such as a methoxy group, an ethoxy group or the like, an aryloxy group such as a phenoxy group or the like, or an aralkyloxy group such as a benzyloxy group or the like, etc.

As the aryl group, an aryl group having 6 to 20 carbon atoms is preferable. Examples thereof include a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, a n-propylphenyl group, an isopropylphenyl group, a n-butylphenyl group, a sec-butylphenyl group, a tert-butylphenyl group, a n-pentylphenyl group, a neopentylphenyl group, a n-hexylphenyl group, a n-octylphenyl group, a n-decylphenyl group, a n-dodecylphenyl group, a n-tetradecylphenyl group, a naphthyl group, an anthracenyl group and the like, and a phenyl group is more preferable.

These aryl groups may be partially substituted with a halogen atom such as a fluorine atom, a chlorine atom, a bromine atom or an iodine atom, an alkoxy group such as a methoxy group, an ethoxy group or the like, an aryloxy group such as a phenoxy group or the like, or an aralkyloxy group such as a benzyloxy group or the like, etc.

As the aralkyl group, an aralkyl group having 7 to 20 carbon atoms is preferable. Examples thereof include a benzyl group, a (2-methylphenyl)methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl) methyl group, a (2,6-dimethylphenyl)methyl group, a (3,4-dimethylphenyl)methyl group, (3,5-dimethylphenyl)methyl group, a (2,3,4-timethylphenyl)methyl group, a (2,3,5-timethylphenyl)methyl group, a (2,3,6-timethylphenyl) methyl group, a (3,4,5-timethylphenyl)methyl group, a (2,4, 6-timethylphenyl)methyl group, a (2,3,4,5-tetramethylphenyl)methyl group, a (2,3,4,6-tetramethylphenyl)methyl group, a (2,3,5,6-tetramethylphenyl)methyl group, a (pentamethylphenyl) methyl group, an (ethylphenyl)methyl group, a (n-propylphenyl)methyl group, a n (isopropylphenyl)methyl group, a (n-butylphenyl)methyl group, a (sec-butylphenyl) methyl group, a (tert-butylphenyl)methyl group, a (n-pentylphenyl)methyl group, a (neopentylphenyl)methyl group, a (n-hexylphenyl)methyl group, a (n-octylphenyl) methyl group, a (n-decylphenyl)methyl group, a (n-dodecylphenyl)methyl group, a (n-tetradecylphenyl) methyl group, a naphthylmethyl group, an anthracenylmethyl group and the like, and a benzyl group is more preferable.

These aralkyl groups may be partially substituted with a halogen atom such as a fluorine atom, a chlorine atom, a bromine atom, an iodine atom or the like, an alkoxy group such as a methoxy group, an ethoxy group or the like, an aryloxy group such as a phenoxy group or the like, or an aralkyloxy group such as a benzyloxy group or the like, etc.

Each of the above-mentioned $L^1$ and $L^2$ is preferably a hydrogen atom, an alkyl group or an aryl group, more preferably a hydrogen atom or an alkyl group, and preferably an alkyl group in particular.

Respective $T^1$, $J^1$, $T^2$ and $J^2$ in the above-mentioned general formulae [2], [3], [5] and [6]independently represent an atom of the Group XV or Group XVI of the Periodic Table of the Elements (Revised edition of IUPAC Inorganic Chemistry Nomenclature 1989). $T^1$ in the general formula [2] and $J^1$ in the general formula [3] may be the same or different. Further, $T^2$ in the general formula [5] and $J^2$ in the general formula [6] may be the same or different. Specific examples of the atom of the Group XV include a nitrogen atom, a phosphorous atom, and the like, and specific examples of the atom of the Group XVI include an oxygen atom, a sulfur atom, and the like. Respective $T^1$, $J^1$, $T^2$ and $J^2$ are preferably a nitrogen atom, or an oxygen atom, and more preferably an oxygen atom.

Respective p, q, r and e in the above-mentioned general formulae [2], [3], [5] and [6] represent a valence of $T^1$, $J^1$, $T^2$ and $J^2$, respectively, and for example, when $T^1$ is an atom of the Group XV, p is 3 and when $T^1$ is an atom of the Group XVI, p is 2.

Respective $R^1$ and $R^3$ in the above-mentioned general formulae [2] and [5] represent an electron-withdrawing group or a group containing an electron-withdrawing group, and when a plural number of $R^1$'s or $R^3$'s exist, they may be mutually the same or different. As an index of the electron-withdrawing property, the substituent constant σ of the Hammet's rule and the like are known, and a functional group in which the substituent constant σ of the Hammet's rule is positive can be mentioned as an electron-withdrawing group.

Specific examples of the electron-withdrawing group include a fluorine atom, a chlorine atom, a bromine atom, an iodine atom, a cyano group, a nitro group, a carbonyl group, a sulfone group, a phenyl group and the like.

The group containing an electron-withdrawing group preferably include a halogenated alkyl group, halogenated aryl, and a (halogenated alkyl)aryl group, cyanated aryl group and nitrated aryl group having up to 20 carbon atoms, an ester group (an alkoxycarbonyl group, aralkyloxycarbonyl group and aryloxycarbonyl group having up to 20 carbon atoms,) and the like.

Specific examples of the halogenated alkyl group include a fluoromethyl group, a chloromethyl group, a bromomethyl group, an iodomethyl group, a difluoromethyl group, a dichloromethyl group, a dibromomethyl group, a diiodomethyl group, a trifluoromethyl group, a trichloromethyl group, a tribromomethyl group, a triiodomethyl group, a 2,2,2-trifluoroethyl group, a 2,2,2-trichloroethyl group, a 2,2,2-tribromoethyl group, a 2,2,2-triiodoethyl group, a 2,2, 3,3,3-pentafluoropropyl group, a 2,2,3,3,3-pentachloropropyl group, a 2,2,3,3,3-pentabromopropyl group, a 2,2,3,3,3-pentaiodopropyl group, a 2,2,2-trifluoro-1-trifluoromethylethyl group, a 2,2,2-trichloro-1-trichloromethylethyl group, a 2,2,2-tribromo-1-tribromomethylethyl group, a 2,2,2-triiodo-1-triiodomethylethyl group, a 1,1-bis(trifluoromethyl)-2,2,2-trifluoroethyl group, a 1,1-bis(trichloromethyl)-2,2,2-trichloroethyl group, a 1,1-bis(tribromomethyl)-2,2,2-tribromoethyl group, a 1,1-bis(triiodomethyl)-2,2,2-triiodoethyl group, and the like.

Specific examples of the halogenated aryl group include a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2,6-difluorophenyl group, a 3,5-difluorophenyl group, a 3,4,5-trifluorophenyl group, a 2,6-dichlorophenyl group, a 3,5-dichlorophenyl group, a 2,6-dibromophenyl group, a 3,5-dibromophenyl group, a 2,6-dibodophenyl group, a 3,5-dibodophenyl group, a 2,4,6-trifluorophenyl group, a 2,4,6-trichlorophenyl group, a 2,4,6-tribromophenyl group, a 2,4,6-triiodophenyl group, a pentafluorophenyl group, a pentachlorophenyl group, a pentabromophenyl group, a pentaiodophenyl group, and the like.

Specific examples of the (halogenated alkyl)aryl group include a 2-(trifluoromethyl)phenyl group, a 3-(trifluoromethyl)phenyl group, a 4-(trifluoromethyl) phenyl group, a 2,6-bis(trifluoromethyl)phenyl group, a 3,5-bis(trifluoromethyl)phenyl group, a 2,4,6-tris (trifluoromethyl)phenyl group, and the like.

Specific examples of the cyanated aryl group include a 2-cyanophenyl group, a 3-cyanophenyl group, a 4-cyanophenyl group and the like.

Specific examples of the nitrated aryl group include a 2-nitrophenyl group, a 3-nitrophenyl group, a 4-nitrophenyl group and the like.

Specific examples of the ester group include a methoxycarbonyl group, an ethoxycarbonyl group, a n-propoxycarbonyl group, an isopropoxycarbonyl group, a phenoxycarbonyl group, a trifluoromethoxycarbonyl group, a pentafluorophenoxycarbonyl group, and the like.

$R^1$ and $R^3$ are preferably the halogenated hydrocarbon group, and more preferably the halogenated alkyl group or halogenated aryl group having up to 20 carbon atoms. Further preferable is a fluoromethyl group, a difluoromethyl group, a trifluoromethyl group, a 2,2,2-trifluoroethyl group, a 2,2,3,3,3-pentafluoropropyl group, a 2,2,2-trifluoro-1-trifluoromethylethyl group, a 1,1-bis(trifluoromethyl)-2,2,2-trifluoroethyl group, a 4-fluorophenyl group, a 2,6-difluorophenyl group, a 3,5-difluorophenyl group, a 3,4,5-trifluorophenyl group, a 2,4,6-trifluorophenyl group, a pentafluorophenyl group, a chloromethyl group, a dichloromethyl group, a trichloromethyl group, a 2,2,2-trichloroethyl group, a 2,2,3,3,3-pentachloropropyl group, a 2,2,2-trichloro-1-trichloromethylethyl group, a 1,1-bis (trichloromethyl)-2,2,2-trichloroethyl group, a 4-chlorophenyl group, a 2,6-dichlorophenyl group, a 3,5-dichlorophenyl group, a 2,4,6-trichlorophenyl group or a pentachlorophenyl group. A fluoroalkyl group or a fluoroaryl group is preferable in particular, and a trifluoromethyl group, a 2,2,2-trifluoro-1-trifluoromethylethyl group, a 1,1-bis (trifluoromethyl)-2,2,2-trifluoroethyl group, a 3,4,5-trifluorophenyl group, or a pentafluorophenyl group is most preferable.

$R^2$ represents in the general formula [3] represents a hydrocarbon group or a halogenated hydrocarbon group, and when a plural number of $R^2$'s exist, they may be mutually the same or different. The hydrocarbon group in $R^2$ is preferably an alkyl group, aryl group or aralkyl group having up to 20 carbon atoms, and the same hydrocarbon group as illustrated in the general formula [1] as $L^1$ is used. The halogenated hydrocarbon group in $R^2$ includes a halogenated alkyl group, halogenated aryl group, or (halogenated alkyl)aryl group having up to 20 carbon atoms, and the like, and the same halogenated alkyl group, halogenated aryl group, and (halogenated alkyl)aryl group as mentioned as specific examples of the electron-withdrawing group in $R^1$ of the general formula [2] are used.

$R^2$ in the general formula [3] is preferably a halogenated hydrocarbon group, and further preferably a fluorinated hydrocarbon group.

$R^4$ in the general formula [6] represents an organic group having a valence of f, and is preferably a saturated aliphatic hydrocarbon group having a valence of f or an aromatic hydrocarbon group having a valence of f.

"f" in the general formula [6] is a valence of $R^4$ and an integer of 2 to 10, preferably an integer of 2 to 6, more preferably an integer of 2 to 4, further more preferably an integer of 2 or 3, and most preferably 2.

Specific examples of the compounds (a) and (d) in the case in which each of $M^1$ and $M^2$ is a zinc atom, include dialkylzincs such as dimethylzinc, diethylzinc, dipropylzinc, di-n-butylzinc, di-isobutylzinc, di-n-hexylzinc, diallylzinc, bis(cyclopentadienyl) zinc and the like; diarylzincs such as diphenylzinc, dinaphthylzinc, bis(pentafluorophenyl)zinc and the like; alkylzinc halides such as methylzinc chloride, ethylzinc chloride, propylzinc chloride, n-butylzinc chloride, isobutylzinc chloride, n-hexylzinc chloride, methylzinc bromide, ethylzinc bromide, propylzinc bromide, n-butylzinc bromide, isobutylzinc bromide, n-hexylzinc bromide, methylzinc iodide, ethylzinc iodide, propylzinc iodide, n-butylzinc iodide, isobutylzinc iodide, n-hexylzinc iodide and the like; zinc halides such as zinc fluoride, zinc chloride, zinc bromide and zinc iodide; and the like.

The compounds (a) and (d) are preferably dialkylzincs, further preferably dimethylzinc, diethylzinc, dipropylzinc, di-n-butylzinc, di-isobutylzinc, di-n-hexylzinc, diallylzinc or bis(cyclopentadienyl)zinc, and in particular, dimethylzinc or diethylzinc is preferable.

Specific examples of the compounds (b) and (e) include amines such as difluoromethylamine, dichloromethylamine, dibromomethylamine, diiodomethylamine, bis (difluoromethyl)amine, bis(dichloromethyl)amine, bis (dibromomethyl)amine, bis(diiodomethyl)amine, bis (trifluoromethyl)amine, bis(trichloromethyl)amine, bis (tribromomethyl)amine, bis(triiodomethyl)amine, bis (2,2,2-trifluoroethyl) amine, bis(2,2,2-trichloroethyl)amine, bis (2,2,2-tribromoethyl)amine, bis(2,2,2-triiodoethyl)amine, bis(2,2,3,3,3-pentafluoropropyl)amine, bis(2,2,3,3,3-pentachloropropyl)amine, bis(2,2,3,3,3-pentabromopropyl) amine, bis(2,2,3,3,3-pentaiodopropyl)amine, bis(2,2,2-trifluoro-1-trifluoromethylethyl)amine, bis(2,2,2-trichloro-1-trichloromethylethyl)amine, bis(2,2,2-tribromo-1-tribromomethylethyl)amine, bis(2,2,2-triiodo-1-triiodomethylethyl)amine, bis(1,1-bis(trifluoromethyl)-2,2, 2-trifluoroethyl)amine, bis(1,1-bis(trichloromethyl)-2,2,2-trichloroethyl)amine, bis(1,1-bis(tribromomethyl)-2,2,2-tribromoethyl)amine, bis(1,1-bis(triiodomethyl)-2,2,2-triiodoethyl)amine, bis(2-fluorophenyl)amine, bis(3-fluorophenyl)amine, bis(4-fluorophenyl)amine, bis(2-chlorophenyl)amine, bis(3-chlorophenyl)amine, bis(4-chlorophenyl)amine, bis(2-bromophenyl)amine, bis(3-bromophenyl)amine, bis(4-bromophenyl)amine, bis(2-iodophenyl)amine, bis(3-iodophenyl)amine, bis(4-iodophenyl)amine, bis(2,6-difluorophenyl)amine, bis(3,5-difluorophenyl)amine, bis(2,6-dichlorophenyl)amine, bis(3, 5-dichlorophenyl)amine, bis(2,6-dibromophenyl)amine, bis (3,5-dibromophenyl)amine, bis(2,6-diiodophenyl)amine, bis(3,5-diiodophenyl)amine, bis(2,4,6-trifluorophenyl) amine, bis(2,4,6-trichlorophenyl)amine, bis(2,4,6-tribromophenyl)amine, bis(2,4,6-triiodophenyl)amine, bis (pentafluorophenyl)amine, bis (pentachorophenyl)amine, bis(pentabromophenyl)amine, bis(pentaiodophenyl)amine, bis(2-(trifluoromethyl)phenyl)amine, bis(3-

(trifluoromethyl)phenyl)amine, bis(4-(trifluoromethyl) phenyl)amine, bis(2,6-di(trifluoromethyl)phenyl)amine, bis (3,5-di(trifluoromethyl)phenyl)amine, bis(2,4,6-tri (trifluoromethyl)phenyl)amine, bis(2-cyanophenyl)amine, bis(3-cyanophenyl)amine, bis(4-cyanophenyl)amine, bis(2-nitrophenyl)amine, bis(3-nitrophenyl)amine, bis(4-nitrophenyl)amine and the like. Further, phosphine compounds in which a nitrogen atom is replaced with a phosphorus atom in the above-mentioned amine compounds, and the like are also exemplified.

When the compounds (b) and (e) are alcohols, specific examples thereof include fluoromethanol, chloromethanol, bromomethanol, iodomethanol, difluoromethanol, dichloromethanol, dibromomethanol, diiodomethanol, trifluoromethanol, trichloromethanol, tribromomethanol, triiodomethanol, 2,2,2-trifluoroethanol, 2,2,2-trichloroethanol, 2,2,2-tribromoethanol, 2,2,2-triiodoethanol, 2,2,3,3,3-pentafluoropropanol, 2,2,3,3,3-pentachloropropanol, 2,2,3,3,3-pentabromopropanol, 2,2,3,3,3-pentaiodopropanol, 2,2,2-trifluoro-1-trifluoromethylethanol, 2,2,2-trichloro-1-trichloromethylethanol, 2,2,2-tribromo-1-tribromomethylethanol, 2,2,2-triiodo-1-triiodomethylethanol, 1,1-bis(trifluoromethyl)-2,2,2-trifluoroethanol, 1,1-bis(trichloromethyl)-2,2,2-trichloroethanol, 1,1-bis(tribromomethyl)-2,2,2-tribromoethanol, 1,1-bis(triiodomethyl)-2,2,2-triiodoethanol and the like. Further, thiol compounds in which an oxygen atom is replaced with a sulfur atom in the above-mentioned alcohol compounds, and the like are also exemplified.

When the compounds (b) and (e) are phenols, specific examples thereof include 2-fluorophenol, 3-fluorophenol, 4-fluorophenol, 2-chlorophenol, 3-chlorophenol, 4-chlorophenol, 2-bromophenol, 3-bromophenol, 4-bromophenol, 2-iodophenol, 3-iodophenol, 4-iodophenol, 2,6-difluorophenol, 3,5-difluorophenol, 3,4,5-trifluorophenol, 2,6-dichlorophenol, 3,5-dichlorophenol, 2,6-dibromophenol, 3,5-dibromophenol, 2,6-diiodophenol, 3,5-diiodophenol, 2,4,6-trifluorophenol, 2,4,6-trichlorophenol, 2,4,6-tribromophenol, 2,4,6-triiodophenol, pentafluorophenol, pentachlorophenol, pentabromophenol, pentaiodophenol, 2-(trifluoromethyl)phenol, 3-(trifluoromethyl)phenol, 4-(trifluoromethyl)phenol, 2,6-bis(trifluoromethyl)phenol, 3,5-bis(trifluoromethyl)phenol, 2-cyanophenol, 3-cyanophenol, 4-cyanophenol, 2-nitrophenol, 3-nitrophenol, 4-nitrophenol and the like. Further, thiophenol compounds in which an oxygen atom is replaced with a sulfur atom in the above-mentioned phenol compounds, and the like are also exemplified.

When the compounds (b) and (e) are carboxylic acids, specific examples thereof include 2-fluorobenzoic acid, 3-fluorobenzoic acid, 4-fluorobenzoic acid, 2,3-difluorobenzoic acid, 2,4-difluorobenzoic acid, 2,5-difluorobenzoic acid, 2,6-difluorobenzoic acid, 2,3,4-trifluorobenzoic acid, 2,3,5-trifluorobenzoic acid, 2,3,6-trifluorobenzoic acid, 2,4,5-trifluorobenzoic acid, 2,4,6-trifluorobenzoic acid, 2,3,4,5-tetrafluorobenzoic acid, 2,3,4,6-tetrafluorobenzoic acid, pentafluorobenzoic acid, fluoroacetic acid, difluoroacetic acid, trifluoroacetic acid, pentafluoropropanoic acid, heptafluorobutanoic acid, 1,1-bis(trifluoromethyl)-2,2,2-trifluoroehtanoic acid and the like.

When the compounds (b) and (e) are sulfonic acids, specific examples thereof include fluoromethanesulfonic acid, difluoromethanesulfonic acid, trifluoromethanesulfonic acid, pentafluoroethanesulfonic acid, heptafluoropropanesulfonic acid, 1,1-bis(trifluoromethyl)-2,2,2-trifluoroehtanesulfonic acid and the like.

The compounds (b) and (e) are preferably, bis(trifluoromethyl)amine, bis(2,2,2-trifluoromethyl)amine, bis(2,2,3,3,3-pentafluoropropyl)amine, bis(2,2,2-trifluoro-1-trifluoromethylethyl)amine, bis(1,1-bis(trifluoromethyl)-2,2,2-trifluoroethyl)amine or bis(pentafluorophenyl)amine as amines; trifluoromethanol, 2,2,2-trifluoroethanol, 2,2,3,3,3-pentafluoropropanol, 2,2,2-trifluoro-1-trifluoromethylethanol or 1,1-bis(trifluoromethyl)-2,2,2-trifluoroethanol as alcohols; 2-fluorophenol, 3-fluorophenol, 4-fluorophenol, 2,6-difluorophenol, 3,5-difluorophenol, 3,4,5-trifluorophenol, 2,4,6-trifluorophenol, pentafluorophenol, 2-(trifluoromethyl)phenol, 3-(trifluoromethyl)phenol, 4-(trifluoromethyl)phenol, 2,6-bis(trifluoromethyl)phenol, 3,5-bis(trifluoromethyl)phenol or 2,4,6-tris(trifluoromethyl) phenol as phenols; pentafluorobenzoic acid or trifluoroacetic acid as carboxylic acids; and trifluoromethanesulfonic acid as sulfonic acids.

The compounds (b) and (e) are more preferably, bis(trifluoromethyl)amine, bis(pentafluorophenyl) amine, trifluoromethanol, 2,2,2-trifluoro-1-trifluoromethylethanol, 1,1-bis(trifluoromethyl)-2,2,2-trifluoroethanol, 4-fluorophenol, 2,6-difluorophenol, 2,4,6-trifluorophenol, 3,4,5-trifluorophenol, pentafluorophenol, 4-(trifluoromethyl)phenol, 2,6-bis(trifluoromethyl)phenol or 2,4,6-tris(trifluoromethyl)phenol, and further preferably 3,4,5-trifluorophenol, pentafluorophenol or 1,1-bis(trifluoromethyl)-2,2,2-trifluoroethanol.

The compounds (c) are preferably water, hydrogen disulfide, an alkylamine, arylamine, aralkylamine halogenated alkylamine, halogenated arylamine, and (halogenated alkyl)arylamine having up to 20 carbon atoms, and specific examples thereof include water, hydrogen disulfide, methylamine, ethylamine, n-propylamine, isopropylamine, n-butylamine, sec-butylamine, tert-butylamine, isobutyl amine, n-pentylamine, neopentylamine, amyl amine, n-hexylamine, n-octylamine, n-decyl amine, n-dodecyl amine, n-eicosylamine, allylamine, cyclopentadienylamine, aniline, 2-tolylamine, 3-tolylamine, 4-tolylamine, 2,3-xylylamine, 2,4-xylylamine, 2,5-xylylamine, 2,6-xylylamine, 3,4-xylylamine, 3,5-xylylamine, 2,3,4-trimethylaniline, 2,3,5-trimethylaniline, 2,3,6-trimethylaniline, 2,4,6-trimethylaniline, 3,4,5-trimethylaniline, 2,3,4,5-tetramethylaniline, 2,3,4,6-tetramethylaniline, 2,3,5,6-tetramethylaniline, pentamethylaniline, ethylaniline, n-propylaniline, isopropylaniline, n-butylaniline, sec-butylaniline, tert-butylaniline, n-pentylaniline, neopentylaniline, n-hexylaniline, n-octylaniline, n-decylaniline, n-dodecylaniline, n-tetradecylaniline, naphthylamine, anthracenylamine, benzylamine, (2-methylphenyl)methylamine, (3-methylphenyl)methylamine, (4-methylphenyl)methylamine, (2,3-dimethylphenyl)methylamine, (2,4-dimethylphenyl)methylamine, (2,5-dimethylphenyl)methylamine, (2,6-dimethylphenyl)methylamine, (3,4-dimethylphenyl)methylamine, (3,5-dimethylphenyl)methylamine, (2,3,4-trimethylphenyl)methylamine, (2,3,5-trimethylphenyl)methylamine, (2,3,6-trimethylphenyl)methylamine, (3,4,5-trimethylphenyl)methylamine, (2,4,6-trimethylphenyl)methylamine, (2,3,4,5-tetramethylphenyl)methylamine, (2,3,4,6-tetramethylphenyl)methylamine, (2,3,5,6-tetramethylphenyl)methylamine, (pentamethylphenyl)methylamine, (ethylphenyl)methylamine, (n-propylphenyl)methylamine, (isopropylphenyl)methylamine, (n-butylphenyl)methylamine, (sec-butylphenyl)methylamine, (tert-butylphenyl)methylamine,(n-pentylphenyl)methylamine, (neopentylphenyl)

methylamine, (n-hexylphenyl)methylamine, (n-octylphenyl)methylamine, (n-decylphenyl)methylamine, (n-dodecylphenyl)methylamine, naphtylmethylamine, anthracenylmethylamine, fluoromethylamine, chloromethylamine, bromomethylamine, iodomethylamine, difluoromethylamine, dichloromethylamine, dibromomethylamine, diiodomethylamine, trifluoromethylamine, trichloromethylamine, tribromomethylamine, triiodomethylamine, 2,2,2-trifluoroethylamine, 2,2,2-trichloroethylamine, 2,2,2-tribromoethylamine, 2,2,2-triiodoethylamine, 2,2,3,3,3-pentafluoropropylamine, 2,2,3,3,3-pentachloropropylamine, 2,2,3,3,3-pentabromopropylamine, 2,2,3,3,3-pentaiodopropylamine, 2,2,2-trifluoro-1-trifluoromethylethylamine, 2,2,2-trichloro-1-trichloromethylethylamine, 2,2,2-tribromo-1-tribromomethylethylamine, 2,2,2-triiodo-1-triiodomethylethylamine, 1,1-bis(trifluoromethyl)-2,2,2-trifluoroethylamine, 1,1-bis(trichloromethyl)-2,2,2-trichloroethylamine, 1,1-bis(tribromoethyl)-2,2,2-tribromoethylamine, 1,1-bis(triiodomethyl)-2,2,2-triiodoethylamine, 2-fluoroaniline, 3-fluoroaniline, 4-fluoroaniline, 2-chloroaniline, 3-chloroaniline, 4-chloroaniline, 2-bromoaniline, 3-bromoaniline, 4-bromoaniline, 2-iodoaniline, 3-iodoaniline, 4-iodoaniline, 2,6-difluoroaniline, 3,5-difluoroaniline, 2,6-dichloroaniline, 3,5-dichloroaniline, 2,6-dibromoaniline, 3,5-dibromoaniline, 2,6-diiodoaniline, 3,5-diiodoaniline, 2,4,6-trifluoroaniline, 2,4,6-trichloroaniline, 2,4,6-tribromoaniline, 2,4,6-triiodoaniline, pentafluoroaniline, pentachloroaniline, pentabromoaniline, pentaiodoaniline, 2-(trifluoromethyl) aniline, 3-(trifluoromethyl) aniline, 4-(trifluoromethyl)aniline, 2,6-di(trifluoromethyl)aniline, 3,5-di(trifluoromethyl)aniline and 2,4,6-tri(trifluoromethyl) aniline; more preferably water, hydrogen disulfide, methylamine, ethylamine, n-propylamine, isopropylamine, n-butylamine, sec-butylamine, tert-butylamine, isobutyl amine, n-octylamine, aniline, 2,6-xylylamine, 2,4,6-trimethylaniline, naphthylamine, anthracenylamine, benzylamine, trifluoromethylamine, pentafluoroethylamine, perfluoroproylamine, perfluorobutylamine, perfluoropentylamine, perfluorohexylamine, perfluorooctylamine, perfluorododecylamine, perfluoropentadecylamine, perfluoroeicosylamine, 2-fluoroaniline, 3-fluoroaniline, 4-fluoroaniline, 2,6-difluoroaniline, 3,5-difluoroaniline, 2,4,6-trifluoroaniline, pentafluoroaniline, 2,-(trifluoromethyl)aniline, 3-(trifluoromethyl)aniline, 4-(trifluoromethyl)aniline, 2,6-bis(trifluoromethyl)aniline, 3,5-bis(trifluoromethyl)aniline or 2,4,6-tris(trifluoromethyl)aniline; in particular, preferably water, trifluoromethylamine, perfluorobutylamine, perfluorooctylamine, perfluoropentadecylamine, 2-fluoroaniline, 3-fluoroaniline, 4-fluoroaniline, 2,6-difluoroaniline, 3,5-difluoroaniline, 2,4,6-trifluoroaniline, pentafluoroaniline, 2-(trifluoromethyl)aniline, 3-(trifluoromethyl) aniline, 4-(trifluoromethyl) aniline, 2,6-bis(trifluoromethyl)aniline, 3,5-bis(trifluoromethyl)aniline and 2,4,6-tris(trifluoromethyl)aniline; and most preferably water and pentafluoroaniline.

Further, as the compound (f) used for preparation of the compound [B], the followings and the like are mentioned.

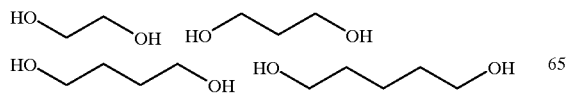

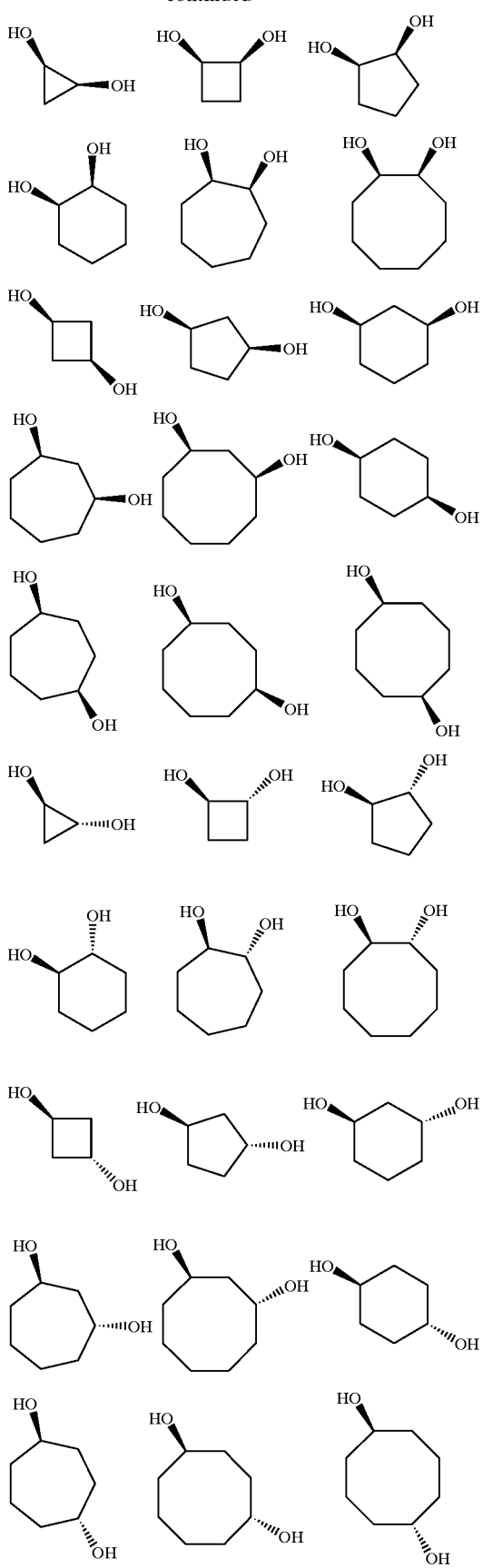

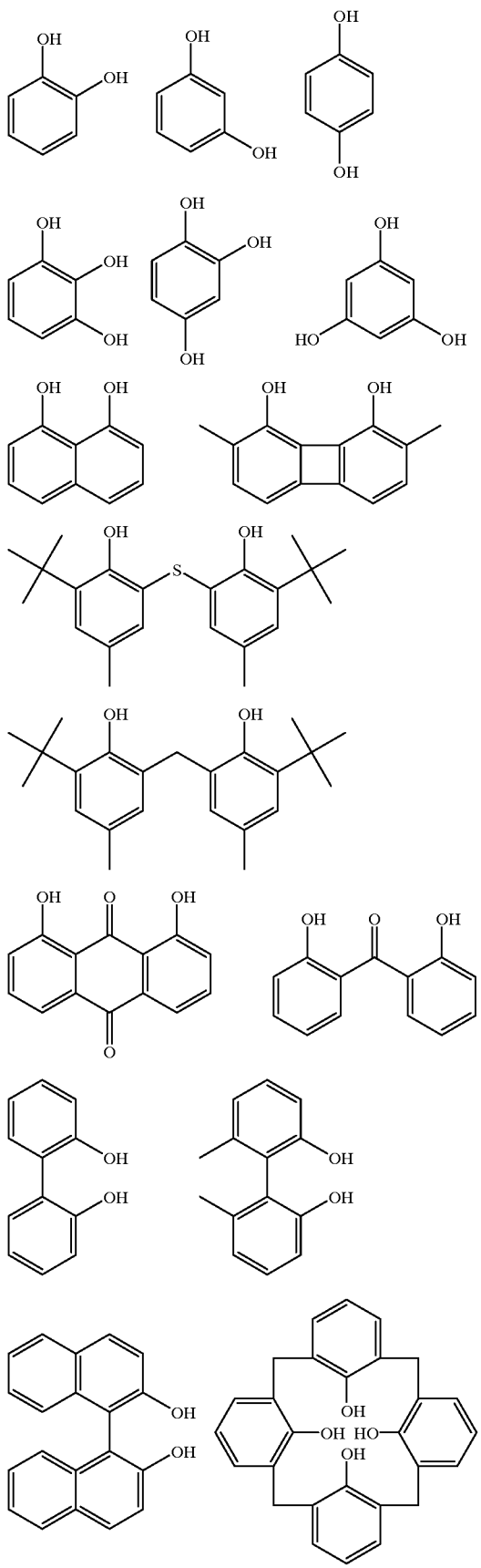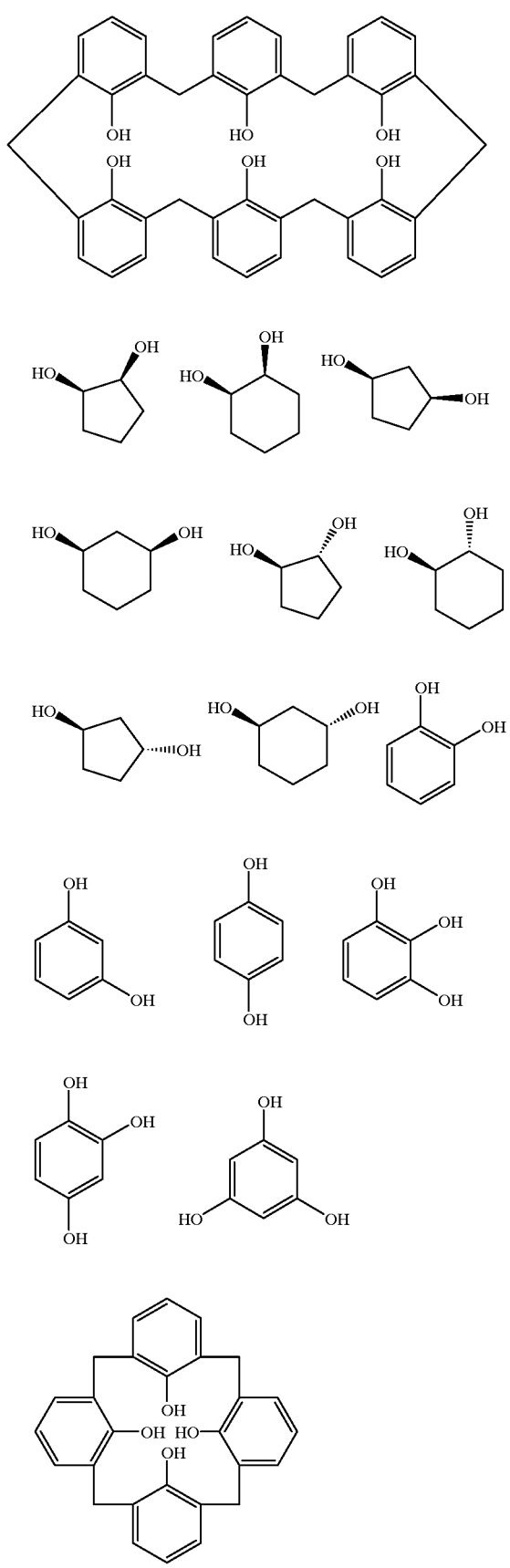

-continued

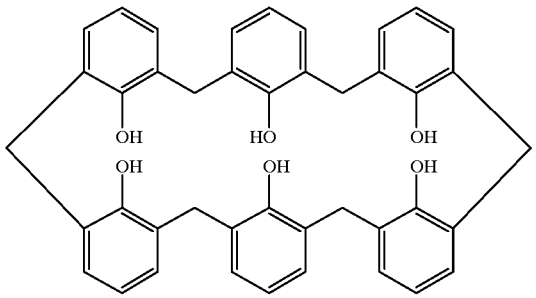

The compound [A] is a compound obtained by contacting the above-mentioned compounds (a), (b) and (c). The order of contacting the compounds (a), (b) and (c) is not specifically limited, and for example, the following order can be adopted.

① A method of contacting (c) after contacting (a) and (b).
② A method of contacting (b) after contacting (a) and (c).
③ A method of contacting (a) after contacting (b) and (c).

The contact order is preferably ① or ②. Namely, the compound [A] is preferably a compound obtained by contacting (c) with a contact product obtained by contacting (a) and (b), or a compound obtained by contacting (b) with a contact product obtained by contacting (a) and (c).

Further, the compound [B] is a compound obtained by contacting the above-mentioned compounds (d), (e) and (f). The order of contacting the compounds (d), (e) and (f) is not specifically limited, and for example, the following order can be adopted.

①' A method of contacting (f) after contacting (d) and (e).
②' A method of contacting (e) after contacting (d) and (f).
③' A method of contacting (d) after contacting (e) and (f).

The contact order is preferably ①' or ②'. Namely, the compound [B] is preferably a compound obtained by contacting (f) with a contact product obtained by contacting (d) and (e), or a compound obtained by contacting (e) with a contact product obtained by contacting (d) and (f).

The contact treatment in the preparation of the above-mentioned compounds [A] and [B] is preferably carried out under an inert gas atmosphere. The treatment temperature is usually from −100° C. to 200° C., and preferably from −80° C. to 150° C. The treatment time is usually from 1 minute to 36 hours, and preferably from 10 minutes to 24 hours. Further, the treatment may use a solvent, and these compounds may be directly treated without using it. The solvent used is inert to the raw material compounds (a), (b) and (c), or (d), (e) and (f).

Either of a non-polar solvent such as an aliphatic hydrocarbon solvent, an aromatic hydrocarbon solvent or the like, or a polar solvent such as an ethereal solvent or the like, can be used. Specific examples of the solvent include butane, hexane, heptane, octane, 2,2,4-trimethylpentane, cyclohexane, benzene, toluene, xylene, dimethyl ether, diethyl ether, diisopropyl ether, di-n-butyl ether, methyl tert-butyl ether, anisole, 1,4-dioxane, 1,2-dimethoxyethane, bis(2-methoxyethyl) ether, tetrahydrofuran, tetrahydropyran and the like.

In the present invention, a polar solvent is preferable among these solvents. As index representing the polarity of the solvent, $E_T^N$ value (C. Reichardt, "Solvents and Solvents Effects in Organic Chemistry", 2nd ed., VCH Verlag (1988)) and the like are known, and in particular, preferably, the polar solvent is a solvent which satisfies the expression:

$E_T^N$ of $0.5 \leq E_T^N \geq 0.1$

Examples of the polar solvent include ethereal solvents such as dimethyl ether, diethyl ether, diisopropyl ether, di-n-butyl ether, methyl tert-butyl ether, anisole, 1,4-dioxane, 1,2-dimethoxyethane, bis(2-methoxyethyl) ether, tetrahydrofuran, tetrahydropyran and the like, and tetrahydrofuran is most preferable as the solvent.

The amounts used of the respective compounds in the preparation of the compound [A] are not specifically limited. When the molar ratio of the amounts used of the respective compounds is defined as a molar ratio of $(a):(b):(c)=1:y^1:z^1$, it is preferable that $y^1$ and $z^1$ satisfy substantially the expression (1):

$$c = y^1 + 2z^1 \quad (1)$$

(wherein c represents a valence of $M^1$ in the expression (1)).

$y^1$ in the expression (1) is preferably a numeral of from 0.01 to 1.99, more preferably a numeral of from 0.20 to 1.80, further preferably a numeral of from 0.25 to 1.50, and most preferably a numeral of from 0.50 to 1.00. $z^1$ in the expression (1) is a numeral determined by $c, y^1$ and the expression (1).

Further, the amount used of the respective compounds is not also specifically limited in the preparation of the compound [B]. When the molar ratio of the amounts used of the respective compounds is defined as a molar ratio of $(d):(e):(f)=x^1:y^2:z^2$ it is preferable that $x^1$, $y^2$ and $z^2$ satisfy substantially the expression (2) when J in the general formula [6] is an atom of Group XVI, and the expression (3) when J in the general formula [6] is an atom of Group XV:

$$d \times x^1 = y^2 + f \times z^2 \quad (2)$$

$$y^2 + f \times z^2 \leq d \times x^1 \leq y^2 + 2 \times f \times z^2 \quad (3)$$

(wherein each of d and f in the expressions (2) and (3) is the same value as in the above-mentioned general formula [4] or [6], respectively.)

$y^2$ in the expressions (2) and (3) is preferably a numeral of $y^2/x^1$ of from 0.01 to 1.99, more preferably a numeral of from 0.2 to 1.8, further preferably a numeral of from 0.25 to 1.5, and most preferably a numeral of from 0.5 to 1.0. $z^2$ in the expressions (2) or (3) is a numeral determined by d, f, $x^1$, $y^2$ and the above-mentioned expression (2) or (3). Further, $x^1$ is a numeral being an arbitrary positive value.

Even if the use of the respective compounds are really designed so as to perfectly satisfy the above-mentioned expressions (1) to (3) in the contact treatment of the above-mentioned compounds, the amounts used may fluctuate finely, and it is usually carried out to appropriately increase and decrease the amounts used to a certain degree considering the amount of a compound which remains while being unreacted. Herein, "satisfy substantially" means that a case of designing to obtain a compound obtained by contacting the respective compounds at the molar ratio satisfying the above-mentioned expressions is included even if the above-mentioned expressions is not perfectly satisfied.

When the molar ratio of the amounts used of the respective compounds is defined as a molar ratio of $(a):(b):(c)=1:y^1:z^1$ in the preparation of the compound [A], it is preferable that $y^1$ and $z^1$ satisfy the expression (4):

$$0 \leq |c - y^1 - 2 z^1| \leq 0.2 \quad (4)$$

(c represents a valence of $M^1$ in the expression (4)).

Further, when the molar ratio of the amounts used of the respective compounds is defined as a molar ratio of (d):(e)

:(f)=x¹:y²:z² in the preparation of the compound [B], it is preferable that $x^1$, $y^2$ and $z^2$ satisfy the expression (5) when J in the general formula [6] is an atom of Group XVI:

$$0 \leq |d-(y^2+f \times z^2)+x^1| \leq 0.2 \qquad (5)$$

(each of d and f in the expression (5) is the same value as in the above-mentioned formula [4] or [6].)

As a result of the contact treatment, at least one of (a), (b) and (c) or at least one of (d), (e) and (f) which are raw materials may remain as unreacted matters concerning the compounds.

Further, it is preferable in the preparation of the compound [A] to distill the solvent from the product after the contact treatment and carry out drying at 25° C. or more for one hour or more under reduced pressure. It is more preferable to carry out drying at 60 to 200° C. for one to 24 hours and most preferable at 80 to 160° C. for 4 to 18 hours.

Specific example of the production process of the compound [A] is shown below in detail when $M^1$ is zinc atom, the compound (b) is pentafluorophenol, and the compound (c) is water. A process which include the following steps can be adopted:
Tetrahydrofuran is used as a solvent; a hexane solution of diethylzinc is added thereto and cooled to 0° C.; pentafluorophenol of the equimolar amount to diethylzinc is added dropwise thereto; after stirring at room temperature for 10 minutes to 24 hours, 0.5-fold molar amount of water to diethylzinc is further added dropwise; after stirring at room temperature for 10 minutes to 24 hours, the solvent is removed by distillation; and drying is carried out at 120° C. for 8 hours under reduced pressure.

Of course, the compounds used in these treatments are not limited to pentafluorophenol and water, the compound as a raw material is not limited to a zinc compound, and the condition at drying is not limited to at 120° C. for 8 hours.

Further, a specific example of the production process of the compound [B] is shown below in detail when $M^2$ is zinc atom, the compound (e) is pentafluorophenol, and the compound (f) is 1,3-cyclopentanediol(a mixture of cis-isomer and trans-isomer).

A process which include the following steps can be adopted:
A hexane solution of diethylzinc and toluene are charged in a flask whose atmosphere was replaced with argon and the mixture is stirred and cooled at −78° C.; a hexane solution of pentafluorophenol which is an equimolar amount to diethylzinc is added thereto dropwise and the resultant was stirred at room temperature for 1 hour; thereafter, 0.5-fold molar amount of 1,3-cyclopentanediol (a mixture of cis-isomer and trans-isomer) to diethylzinc is further added dropwise and stirring is carried out overnight; and then, a volatile material is removed by distillation and a solid prepared is dried at room temperature under reduced pressure.

Of course, the compound used in these treatments is not limited to pentafluorophenol and 1,3-cyclopentanediol (a mixture of cis-isomer and trans-isomer), and the metal compound as a raw material is not limited to a zinc compound.

Next, the compound [C] represented by the general formula [7] is illustrated.

$M^3$ has been already described.

$T^3$ in the general formula [7] represents an atom of the Group XIV, Group XV or Group XVI of the Periodic Table of the Elements (Revised edition of IUPAC Inorganic Chemistry Nomenclature 1989), and when a plural number of $T^3$'s exist, they may be mutually the same or different. Specific example of the atom of the Group XIV includes a carbon atom, a silicon atom and the like, specific example of the atom of the Group XV includes a nitrogen atom, a phosphorous atom and the like, and specific example of the atom of the Group XVI includes an oxygen atom, a sulfur atom and the like. $T^3$ is preferably a carbon atom, a nitrogen atom or an oxygen atom, further preferably a nitrogen atom or an oxygen atom, and in particular, $T^3$ is preferably an oxygen atom.

"s" in the general formula [7] represents a valence of $T^3$. When $T^3$ is the atom of the Group XIV, "s" is 4, when T is the atom of Group XV, "s" is 3, and when $T^3$ is the atom of Group XVI, "s" is 2.

$R^5$ in the general formula [7] represents an electron-withdrawing group or a group containing an electron-withdrawing group, and when a plural number of $R^5$'s exist, they may be mutually the same or different. Examples of the electron-withdrawing group or the group containing an electron-withdrawing group are selected from those already described in the illustration of $R_1$ and $R^3$, and the preferable group is the same group as in $R^1$ and $R^3$.

Further, $R^6$ represents a hydrocarbon group, and a plural number of $R^6$'s may be mutually the same or different. The hydrocarbon group in $R^6$ is preferably an alkyl group, an aryl group or an aralkyl group.

As the alkyl group herein, an alkyl group having 1 to 20 carbon atoms is preferable. Examples include a methyl group, an ethyl group, a n-propyl group, an isopropyl group, a n-butyl group, a sec-butyl group, a tert-butyl group, an isobutyl group, a n-pentyl group, a neopentyl group, a n-hexyl group, a n-octyl group, a n-decyl group, a n-dodecyl group, a n-pentadecyl group, a n-eicosyl group, and the like. A methyl group, an ethyl group, an isopropyl group, a tert-butyl group or an isobutyl group is more preferable.

Any one of these alkyl groups may be substituted with a halogen atom such as a fluorine atom, a chlorine atom, a bromine atom or an iodine atom. Examples of the alkyl group having 1 to 20 carbon atoms which is substituted with the halogen atom include a fluoromethyl group, a difluoromethyl group, a trifluoromethyl group, a chloromethyl group, a dichloromethyl group, a trichloromethyl group, a bromomethyl group, a dibromomethyl group, a tribromomethyl group, an iodomethyl group, a diiodomethyl group, a triiodomethyl group, a fluoroethyl group, a difluoroethyl group, a trifluoroethyl group, a tetrafluoroethyl group, a pentafluoroethyl group, a chloroethyl group, a dichloroethyl group, a trichloroethyl group, a tetrachloroethyl group, a pentachloroethyl group, a bromoethyl group, a dibromoethyl group, a tribromoethyl group, a tetrabromoethyl group, a pentabromoethyl group, a perfluoropropyl group, a perfluorobutyl group, a perfluoropentyl group, a perfluorohexyl group, a perfluorooctyl group, a perfluorododecyl group, a perfluoropentadecyl group, a perfluoroeicosyl group, a perchloropropyl group, a perchlorobutyl group, a perchloropentyl group, a perchlorohexyl group, a perchlorooctyl group, a perchlorododecyl group, a perchloropentadecyl group, a perchloroeicosyl group, a perbromopropyl group, a perbromobutyl group, a perbromopentyl group, a perbromohexyl group, a perbromooctyl group, a perbromododecyl group, a perbromopentadecyl group, a perbromoeicosyl group and the like.

Further, any one of these alkyl groups may be partially substituted with an alkoxy group such as a methoxy group, an ethoxy group or the like, an aryloxy group such as a phenoxy group or the like, or an aralkyloxy group such as a benzyloxy group or the like, etc.

As the aryl group, an aryl group having 6 to 20 carbon atoms is preferable. Examples thereof include a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, a n-propylphenyl group, an isopropylphenyl group, a n-butylphenyl group, a sec-butylphenyl group, a tert-butylphenyl group, a n-pentylphenyl group, a neopentylphenyl group, a n-hexylphenyl group, a n-octylphenyl group, a n-decylphenyl group, a n-dodecylphenyl group, a n-tetradecylphenyl group, a naphthyl group, an anthracenyl group and the like, and a phenyl group is more preferable.

Any one of these aryl groups may be partially substituted with a halogen atom such as a fluorine atom, a chlorine atom, a bromine atom or an iodine atom, an alkoxy group such as a methoxy group, an ethoxy group or the like, an aryloxy group such as a phenoxy group or the like, or an aralkyloxy group such as a benzyloxy group or the like, etc.

As the aralkyl group, an aralkyl group having 7 to 20 carbon atoms is preferable. Examples include a benzyl group, a (2-methylphenyl)methyl group, a (3-methylphenyl) methyl group, a (4-methylphenyl)methyl group, a (2,3-dimethylphenyl)methyl group, a (2,4-dimethylphenyl) methyl group, a (2,5-dimethylphenyl)methyl group, a (2,6-dimethylphenyl)methyl group, a (3,4-dimethylphenyl) methyl group, a (3,5-dimethylphenyl)methyl group, a (2,3,4-timethylphenyl)methyl group, a (2,3,5-timethylphenyl) methyl group, a (2,3,6-timethylphenyl)methyl group, a (3,4,5-timethylphenyl)methyl group, a (2,4,6-timethylphenyl) methyl group, a (2,3,4,5-tetramethylphenyl)methyl group, a (2,3,4,6-tetramethylphenyl)methyl group, a (2,3,5,6-tetramethylphenyl)methyl group, a (pentamethylphenyl) methyl group, an (ethylphenyl)methyl group, a (n-propylphenyl)methyl group, an (isopropylphenyl)methyl group, a (n-butylphenyl)methyl group, a (sec-butylphenyl) methyl group, a (tert-butylphenyl)methyl group, a (n-pentylphenyl)methyl group, a (neopentylphenyl)methyl group, a (n-hexylphenyl)methyl group, a (n-octylphenyl) methyl group, a (n-decylphenyl)methyl group, a (n-dodecylphenyl)methyl group, a (n-tetradecylphenyl) methyl group, a naphthylmethyl group, an anthracenylmethyl group and the like, and a benzyl group is more preferable.

Any one of these aryl groups may be partially substituted with a halogen atom such as a fluorine atom, a chlorine atom, a bromine atom or an iodine atom, an alkoxy group such as a methoxy group, an ethoxy group or the like, an aryloxy group such as a phenoxy group or the like, or an aralkyloxy group such as a benzyloxy group or the like, etc.

$R^6$ in the general formula [7] is preferably an aryl group or an alkyl group.

"h" in the general formula [7] represents a numeral of 1 or more, and usually an integer. "h" is preferably an integer of 1 to 5, and in particular, 1.

The compound represented by the general formula [7] is preferably a $\mu$-oxo-bis(alkylzinc) or $\mu$-oxo-bis(arylzinc), in particular.

Two or more of molecules of the compound represented by the general formula [7] may be associated.

The production process of the compound represented by the general formula [7] is not specifically limited, and for example, a process of treating an organometallic compound such as an alkylmetal, a halogenated alkylmetal or the like with a compound selected from a gem-dihalogenohydrocarbon, a silane, a germane, an amine, a phosphine, water, a hydrate of metal salt, hydrogen disulfide and the like, is mentioned.

The treatment is preferably carried out under inert gas atmosphere. The treatment temperature is usually from −100° C. to 200° C., and preferably from −80° C. to 150° C. The treatment time is usually from 1 minute to 36 hours, and preferably from 10 minutes to 24 hours. Further, the treatment may use a solvent, and these compounds may be directly treated without using it. The solvent used is preferably an aliphatic hydrocarbon solvent, an aromatic hydrocarbon solvent or an ethereal solvent which is inert to an organometallic compound such as an alkylmetal, a halogenated alkylmetal or the like and a compound selected from a gem-dihalogenohydrocarbon, a silane, a germane, an amine, a phosphine, water, a hydrate of metal salt, hydrogen disulfide and the like. Specific examples of the solvent include butane, hexane, heptane, octane, benzene, toluene, diethyl ether, di-n-butyl ether, tetrahydrofuran and the like.

Further, in the treatment, the order of dropwise addition of the compound selected from a gem-dihalogenohydrocarbon, a silane, a germane, an amine, a phosphine, water, a hydrate of metal salt, hydrogen disulfide and the like is not specifically limited, it may be successively dropwise added, may be simultaneously dropwise added, and 2 or more of solvents may be dropwise added after mixing. Arbitrary amounts of $R^5$ and $R^6$ can be introduced by adjusting the molar number of the compound selected from a gem-dihalogenohydrocarbon, a silane, a germane, an amine, a phosphine, water, a hydrate of metal salt, hydrogen disulfide and the like to the organometallic compound.

Further, as a result of the treatment, the organometallic compound being a raw material and the compound selected from a gem-dihalogenohydrocarbon, a silane, a germane, an amine, a phosphine, water, a hydrate of metal salt, hydrogen disulfide and the like may remain as an unreacted matter. The compound represented by the general formula [7] which was obtained by the treatment can be used as a catalyst component for addition polymerization after separation and purification such as recrystallization or the like, but the reacted solution can be also used as a catalyst component for addition polymerization. The solvent is preferably removed by distillation from the reacted solution, and drying is preferably carried out at a temperature of 25° C. or more for 1 hour or more under reduced pressure. It is more preferable to carry out drying at 60 to 200° C. for one to 24 hours, and most preferable at 80 to 160° C. for 4 to 18 hours.

Specific example of the production process of the compound represented by the general formula [7] is further shown below in detail when $M^3$ is zinc atom and a treating agent is water.

A process that toluene is a solvent, a hexane solution of a dialkylzinc (for example, diethylzinc) is added thereto and cooled at 0° C., water of an equimolar amount to the dialkylzinc is added dropwise, and the mixture is stirred at room temperature for 10 minutes to 24 hours, can be adopted. Of course, those used in these treatments are not limited to the dialkylzinc and water.

Then, the compound [D] represented by the general formula [8] is illustrated.

$M^4$ has been already described.

As $X^1$, specific examples of the atom of the Group XIV as $X^1$ include a carbon atom, a silicon atom and the like, specific examples of the atom of Group the XV include a nitrogen atom, a phosphorous atom and the like, and specific examples of the atom of the Group XVI include an oxygen atom, a sulfur atom and the like. $X^1$ is preferably a carbon atom, a nitrogen atom or an oxygen atom, further preferably a nitrogen atom or an oxygen atom, and in particular, $X^1$ is preferably an oxygen atom.

"i" in the general formula [8] represents a numeral by 1 smaller than a valence of $X^1$. When $X^1$ is the atom of the Group XIV, "i" is 3, when $X^1$ is the atom of the Group XV, "i" is 2, and when $X^1$ is the atom of the Group XIV, "i" is 1.

$R^7$ in the general formula [8] represents an electron-withdrawing group or a group containing an electron-withdrawing group, and when a plural number of $R^7$'s exist, they may be mutually the same or different. The examples of the electron-withdrawing group or the group containing an electron-withdrawing group are selected from those already described in the illustration of $R^1$ and $R^3$, and the preferable group is the same group as in $R^1$ and $R^3$.

Specific examples of $X^1R^7i$ which is a combination of $X^1$ and $R^7$ when $X^1$ is a carbon atom, include a tri(fluoromethyl)methyl group, a tri(chloromethyl)methyl group, a tri(bromomethyl)methyl group, a tri(iodomethyl)methyl group, a tri(difluoromethyl)methyl group, a tri(dichloromethyl)methyl group, a tri(dibromomethyl)methyl group, a tri(diiodomethyl)methyl group, a tri(trifluoromethyl)methyl group, a tri(trichloromethyl)methyl group, a tri(tribromomethyl)methyl group, a tri(triiodomethyl)methyl group, a tri(2,2,2-trifluoromethyl)methyl group, a tri(2,2,2-trichloromethyl)methyl group, a tri(2,2,2-tribromomethyl)methyl group, a tri(2,2,2-triiodomethyl)methyl group, a tri(2,2,3,3,3-pentafluoropropyl)methyl group, a tri(2,2,3,3,3-pentachloropropyl)methyl group, a tri(2,2,3,3,3-pentabromopropyl)methyl group, a tri(2,2,3,3,3-pentaiodopropyl)methyl group, a tri(2,2,2-trifluoro-1-trifluoromethylethyl)methyl group, a tri(2,2,2-trichloro-1-trichloromethylethyl)methyl group, a tri(2,2,2-tribromo-1-tribromomethylethyl)methyl group, a tri(2,2,2-triiodo-1-triiodomethylethyl)methyl group, a tri(1,1-di(trifluoromethyl)-2,2,2-trifluoroethyl)methyl group, a tri(1,1-di(trichloromethyl)-2,2,2-trichloroethyl)methyl group, a tri(1,1-di(tribromomethyl)-2,2,2-tribromoethyl)methyl group, a tri(1,1-di(triiodomethyl)-2,2,2-triiodoethyl)methyl group, a tri(2-fluorophenyl)methyl group, a tri(3-fluorophenyl)methyl group, a tri(4-fluorophenyl)methyl group, a tri(2-chlorophenyl)methyl group, a tri(3-chlorophenyl)methyl group, a tri(4-chlorophenyl)methyl group, a tri(2-bromophenyl)methyl group, a tri(3-bromophenyl)methyl group, a tri(4-bromophenyl)methyl group, a tri(2-iodophenyl)methyl group, a tri(3-iodophenyl)methyl group, a tri(4-iodophenyl)methyl group, a tri(2,6-difluorophenyl)methyl group, a tri(3,5-difluorophenyl)methyl group, a tri(2,6-dichlorophenyl)methyl group, a tri(3,5-dichlorophenyl)methyl group, a tri(2,6-dibromophenyl)methyl group, a tri(3,5-dibromophenyl)methyl group, a tri(2,6-diiodophenyl)methyl group, a tri(3,5-diiodophenyl)methyl group, a tri(2,4,6-trifluorophenyl)methyl group, a tri(2,4,6-trichlorophenyl)methyl group, a tri(2,4,6-tribromophenyl)methyl group, a tri(2,4,6-triiodophenyl)methyl group, a tri(pentafluorophenyl)methyl group, a tri(pentachlorophenyl)methyl group, a tri(pentabromophenyl)methyl group, a tri(pentaiodophenyl)methyl group, a tri(3-(trifluoromethyl)phenyl)methyl group, a tri(4-(trifluoromethyl)phenyl)methyl group, a tri(2,6-di(trifluoromethyl)phenyl)methyl group, a tri(3,5-di(trifluoromethyl)phenyl)methyl group, a tri(2,4,6-tri(trifluoromethyl)phenyl)methyl group, a tri(2-cyanophenyl)methyl group, a tri(3-cyanophenyl)methyl group, a tri(4-cyanophenyl)methyl group, a tri(2-nitrophenyl)methyl group, a tri(3-nitrophenyl)methyl group, a tri(4-nitrophenyl)methyl group and the like. Further, functional groups obtained by substituting X from carbon atom to silicon atom, and functional groups represented by replacing a methyl group in the above-mentioned specific examples with a silyl group, can be also exemplified.

Similarly, specific examples of $X^1R^7i$ when $X^1$ is a nitrogen atom, include a di(fluoromethyl)amino group, a di(chloromethyl)amino group, a di(bromomethyl)amino group, a di(iodomethyl)amino group, a di(difluoromethyl)amino group, a di(dichloromethyl)amino group, a di(dibromomethyl) amino group, a di (diiodomethyl) amino group, a di(trifluoromethyl)amino group, a di(trichloromethyl)amino group, a di(tribromomethyl)amino group, a di(triiodomethyl)amino group, a di(2,2,2-trifluoroethyl)amino group, a di(2,2,2-trichloroethyl)amino group, a di(2,2,2-tribromoethyl)amino group, a di(2,2,2-di(triiodoethyl)amino group, a di(2,2,3,3,3-pentafluoropropyl)amino group, a di(2,2,3,3,3-pentachloropropyl)amino group, a di(2,2,3,3,3-pentabromopropyl)amino group, a di(2,2,3,3,3-pentaiodopropyl)amino group, a di(2,2,2-trifluoro-1-trifluoromethylethyl)amino group, a di(2,2,2-trichloro-1-trichloromethylethyl)amino group, a di(2,2,2-tribromo-1-tribromomethylethyl)amino group, a di(2,2,2-triiodo-1-triiodomethylethyl)amino group, a di(1,1-bis(trifluoromethyl)-2,2,2-trifluoroethyl)amino group, a di(1,1-di(trichloromethyl)-2,2,2-trichloroethyl)amino group, a di(1,1-di(tribromomethyl)-2,2,2-tribromoethyl)amino group, a di(1,1-di(triiodomethyl)-2,2,2-triiodoethyl)amino group, a di(2-fluorophenyl)amino group, a di(3-fluorophenyl)amino group, a di(4-fluorophenyl)amino group, a di(2-chlorophenyl)amino group, a di(3-chlorophenyl)amine, a di(4-chlorophenyl)amino group, a di(2-bromophenyl) amino group, a di(3-bromophenyl)amino group, a di(4-bromophenyl)amino group, a di(2-iodophenyl)amino group, a di(3-iodophenyl)amino group, a di(4-iodophenyl)amino group, a di(2,6-difluorophenyl)amino group, a di(3,5-difluorophenyl)amino group, a di(2,6-dichlorophenyl)amino group, a di(3,5-dichlorophenyl)amino group, a di(2,6-dibromophenyl)amino group, a di(3,5-dibromophenyl)amino group, a di(2,6-diiodophenyl)amino group, a di(3,5-diiodophenyl)amino group, a di(2,4,6-trifluorophenyl)amino group, a di(2,4,6-trichlorophenyl)amino group, a di(2,4,6-tribromophenyl)amino group, a di(2,4,6-triiodophenyl)amino group, a di(pentafluorophenyl)amino group, a di(pentachlorophenyl)amino group, a di(pentabromophenyl)amino group, a di(pentaiodophenyl)amino group, a di(2-(trifluoromethyl)phenyl)amino group, a di(3-(trifluoromethyl)phenyl)amino group, a di(4-(trifluoromethyl)phenyl)amino group, a di(2,6-di(trifluoromethyl)phenyl)amino group, a di(3,5-di(trifluoromethyl)phenyl)amino group, a di(2,4,6-tri(trifluoromethyl)phenyl)amino group, a di(2-cyanophenyl)amino group, a di(3-cyanophenyl)amino group, a di(4-cyanophenyl)amino group, a di(2-nitrophenyl)amino group, a di(3-nitrophenyl)amino group, a di(4-nitrophenyl)amino group, and the like.

Further, a functional group obtained by substituting X from nitrogen atom to phosphorous atom, and a functional group represented by replacing an amino group in the above-mentioned specific example with a phosphino group can be also exemplified.

Further, specific examples, when $X^1$ is an oxygen atom, include a fluoromethoxy group, a chloromethoxy group, a bromomethoxy group, an iodomethoxy group, a difluoromethoxy group, a dichloromethoxy group, a dibromomethoxy group, a diiodomethoxy group, a trifluoromethoxy group, a trichloromethoxy group, a tribromomethoxy group, a triiodomethoxy group, a 2,2,2-trifluoroethoxy group, a 2,2,2-trichloroethoxy group, a 2,2,2-tribromoethoxy group, a 2,2,2-triiodoethoxy group, a 2,2,3,3,3-pentafluoropropoxy group, a 2,2,3,3,3-pentachloropropoxy group, a 2,2,3,3,3-pentabromopropoxy group, a 2,2,3,3,3-pentaiodopropoxy group, a 2,2,2-trifluoro-1-trifluoromethylethoxy group, a 2,2,2-trichloro-1-trichloromethylethoxy group, a 2,2,2-tribromo-1-tribromomethylethoxy group, a 2,2,2-triiodo-1-triiodomethylethoxy group, a 1,1-di(trifluoromethyl)-2,2,2-trifluoroethoxy group, a 1,1-di(trichloromethyl)-2,2,2-trichloroethoxy group, a 1,1-di(tribromomethyl)-2,2,2-tribromoethoxy group, a 1,1-di(triiodomethyl)-2,2,2-triiodoethoxy group, a 2-fluorophenoxy group, a 3-fluorophenoxy group, a 4-fluorophenoxy group, a 2-chlorophenoxy group, a 3-chlorophenoxy group, a 4-chlorophenoxy group, a 2-bromophenoxy group, a 3-bromophenoxy group, a 4-bromophenoxy group, a 2-iodophenoxy group, a 3-iodophenoxy group, a 4-iodophenoxy group, a 2,6-difluorophenoxy group, a 3,5-difluorophenoxy group, a 3,4,5-trifluorophenoxy group, a 2,6-dichlorophenoxy group, a 3,5-dichlorophenoxy group, a 2,6-dibromophenoxy group, a 3,5-dibromophenoxy group, a 2,6-diiodophenoxy group, a 3,5-diiodophenoxy group, a 2,4,6-trifluorophenoxy group, a 2,4,6-trichlorophenoxy group, a 2,4,6-tribromophenoxy group, a 2,4,6-triiodophenoxy group, a pentafluorophenoxy group, a pentachlorophenoxy group, a pentabromophenoxy group, a pentaiodophenoxy group, a 2-(trifluoromethyl)phenoxy group, a 3-(trifluoromethyl)phenoxy group, a 4-(trifluoromethyl)phenoxy group, a 2,6-di(trifluoromethyl)phenoxy group, a 3,5-di(trifluoromethyl)phenoxy group, a 2,4,6-tri(trifluoromethyl) phenoxy group, a 2-cyanophenoxy group, a 3-cyanophenoxy group, a 4-cyanophenoxy group, a 2-nitrophenoxy group, a 3-nitrophenoxy group, a 4-nitrophenoxy group and the like. Further, a functional group obtained by substituting X from oxygen atom to sulfur atom, and a functional group represented by replacing an oxy group in the above-mentioned specific example with a thioxy group can be also exemplified.

$X^1R^7i$ is preferably a tri(fluoroalkyl)methyl group, a tri(fluoroaryl)methyl group, a di(fluoroalkyl)amino group, a di(fluoroaryl)amino group, a fluoroalkyloxy group or a fluoroaryloxy group, such as a tri(fluoromethyl)methyl group, a tri(pentafluorophenyl)methyl group, a di(fluoromethyl) amino group, a di(pentafluorophenyl) amino group, a trifluoromethoxy group, a 2,2,2-trifluoro-1-trifluoromethylethoxy group, a 1,1-di(trifluoromethyl)-2,2,2-trifluoroethoxy group, a 3,4,5-trifluorophenoxy group, or a pentafluorophenoxy group, more preferably a fluoroalkyloxy group or a fluoroaryloxy group such as a 2,2,2-trifluoro-1-trifluoromethylethoxy group, a 1,1-di(trifluoromethyl)-2,2,2-trifluoroethoxy group, a 3,4,5-trifluorophenoxy group, or a pentafluorophenoxy group.

$R^8$ in the general formula [8] represents a hydrogen atom, a halogen atom or a hydrocarbon group. Specific examples of the halogen atom in $R^8$ include a fluorine atom, a chlorine atom, a bromine atom and an iodine atom. As a hydrocarbon group in $R^8$, an alkyl group, an aryl group or an aralkyl group is preferable. Specific examples thereof include the same compounds as in $R^6$ in the general formula [7] as described above.

$R^8$ in the general formula [8] is preferably an alkyl group or an aryl group, and more preferably an alkyl group, and "t" represents a numeral satisfying $0<t\leq j$. "t" is preferably the same numeral as "j".

Two or more of molecules of the compound represented by the general formula [8] may be associated.

Among the compound represented by the general formula [8], specific examples of a case in which M is a zinc atom, include trifluoromethoxy(trimethylsiloxy)zinc, trifluoromethoxy(triethylsiloxy)zinc, trifluoromethoxy(triphenylsiloxy)zinc, 2,2,2-trifluoroethoxy(trimethylsiloxy)zinc, 2,2,2-trifluoroethoxy(triethylsiloxy)zinc, 2,2,2-trifluoroethoxy(triphenylsiloxy)zinc, 1,1-di(trifluoromethyl)-2,2,2-trifluoroethoxy(trimethylsiloxy)zinc, 1,1-di(trifluoromethyl)-2,2,2-trifluoroethoxy(triethylsiloxy)zinc, 1,1-di(trifluoromethyl)-2,2,2-trifluoroethoxy(triphenylsiloxy)zinc, 2,2,2-trifluoro-1-trifluoromethylethoxy(trimethylsiloxy)zinc, 2,2,2-trifluoro-1-trifluoromethylethoxy(triethylsiloxy)zinc, 2,2,2-trifluoro-1-trifluoromethylethoxy(triphenylsiloxy)zinc, 2,2,2,3,3,3-pentafluoropropoxy(trimethylsiloxy)zinc, 2,2,2,3,3,3-pentafluoropropoxy(triethylsiloxy)zinc, 2,2,2,3,3,3-pentafluoropropoxy(triphenylsiloxy)zinc, 2,4,6-trifluorophenoxy(trimethylsiloxy)zinc, 2,4,6-trifluorophenoxy(triethylsiloxy)zinc, 2,4,6-trifluorophenoxy(triphenylsiloxy)zinc, 3,4,5-trifluorophenoxy(trimethylsiloxy)zinc, 3,4,5-trifluorophenoxy(triethylsiloxy)zinc, 3,4,5-trifluorophenoxy(triphenylsiloxy)zinc, pentafluorophenoxy(trimethylsiloxy)zinc, pentafluorophenoxy(triethylsiloxy)zinc, pentafluorophenoxy(triphenylsiloxy)zinc, 4-trifluoromethylphenoxy(trimethylsiloxy)zinc, 4-trifluoromethylphenoxy(triethylsiloxy)zinc, 4-trifluoromethylphenoxy(triphenylsiloxy)zinc, trifluoromethylamido(trimethylsiloxy)zinc, trifluoromethylamido(triethylsiloxy)zinc, trifluoromethylamido(triphenylsiloxy)zinc, 2,2,2-trifluoroethylamido(trimethylsiloxy)zinc, 2,2,2-trifluoroethylamido(triethylsiloxy)zinc, 2,2,2-trifluoroethylamido(triphenylsiloxy)zinc, pentafluoroanilido(trimethylsiloxy)zinc, pentafluoroanilido(triethylsiloxy)zinc, pentafluoroanilido(triphenylsiloxy)zinc, n-trifluoromethylanilido (trimethylsiloxy)zinc, n-trifluoromethylanilido(triethylsiloxy)zinc, n-trifluoromethylanilido(triphenylsiloxy)zinc, trichloromethoxy(trimethylsiloxy)zinc, trichloromethoxy(triethylsiloxy)zinc, trichloromethoxy(triphenylsiloxy)zinc, 2,2,2-trichloroethoxy(trimethylsiloxy)zinc, 2,2,2-trichloroethoxy(triethylsiloxy)zinc, 2,2,2-trichloroethoxy(triphenylsiloxy)zinc, 1,1-di(trichloromethyl)-2,2,2-trichloroethoxy(trimethylsiloxy)zinc, 1,1-di(trichloromethyl)-2,2,2-trichloroethoxy(triethylsiloxy)zinc, 1,1-di(trichloromethyl)-2,2,2-trichloroethoxy(triphenylsiloxy)zinc, 2,2,2-trichloro-m-trichloromethylethoxy(trimethylsiloxy)zinc, 2,2,2-trichloro-1-trichloromethylethoxy(triethylsiloxy)zinc, 2,2,2-trichloro-1-trichloromethylethoxy(triphenylsiloxy)zinc, 2,2,3,3,3-pentachloropropoxy(trimethylsiloxy)zinc, 2,2,3,3,3-pentachloropropoxy(triethylsiloxy)zinc, 2,2,3,3,3-pentachloropropoxy(triphenylsiloxy)zinc, 2,4,6-trichlorophenoxy(trimethylsiloxy)zinc, 2,4,6-trichlorophenoxy(triethylsiloxy)zinc, 2,4,6-trichlorophenoxy(triphenylsiloxy)zinc, pentachlorophenoxy(trimethylsiloxy)zinc, pentachlorophenoxy(triethylsiloxy)zinc, pentachlorophenoxy(triphenylsiloxy)zinc, 4-trichloromethylphenoxy(trimethylsiloxy)zinc, 4-trichloromethylphenoxy(triethylsiloxy)zinc, 4-trichloromethylphenoxy(triphenylsiloxy)zinc, trichloromethylamido (trimethylsiloxy)zinc, trichloromethylamido(triethylsiloxy)zinc, trichloromethylamido(triphenylsiloxy)zinc, 2,2,2-trichloroethylamido(trimethylsiloxy)zinc, 2,2,2- trichloroethylamido(triethylsiloxy)zinc, 2,2,2-trichloroethylamido(triphenylsiloxy)zinc, pentachloroanilido(trimethylsiloxy)zinc, pentachloroanilido(triethylsiloxy)zinc, pentachloroanilido(triphenylsiloxy)zinc, n-trichloromethylanilido(trimethylsiloxy)zinc, n-trichloromethylanilido(triethylsiloxy)zinc, n-trichloromethylanilido(triphenylsiloxy)zinc, bis(trifluoromethoxy)zinc, bis(2,2,2-trifluoroethoxy)zinc, bis(1,1-di(trifluoromethyl)-2,2,2-trifluoroethoxy)zinc, bis(2,2,2-trifluoro-1-trifluoromethylethoxy)zinc, bis(2,2,3,3,3-pentafluoropropoxy)zinc, bis(2,4,6-trifluorophenoxy)zinc, bis(3,4,5-trifluorophenoxy)zinc, bis(pentafluorophenoxy)zinc, bis(4-trifluoromethylphenoxy)zinc, bis(trifluoromethylamido)zinc, bis(pentafluoroanilido)zinc, bis(N-trifluoromethylanilido)zinc, trifluoromethoxyzinc methyl, 2,2,2-trifluoroethoxyzinc methyl, 1,1-di(trifluoromethyl)-2,2,2-trifluoroethoxyzinc methyl, 2,2,2-trifluoro-1-trifluoromethylethoxyzinc methyl, 2,2,3,3,3-pentafluoropropoxyzinc methyl, 2,4,6-trifluorophenoxyzinc methyl, 3,4,5-trifluorophenoxyzinc methyl, pentafluorophenoxyzinc methyl, 4-trifluoromethylphenoxyzinc methyl, 4-trifluoromethylamidozinc methyl, 2,2,2-trifluoroethylamidozinc methyl, pentafluoroanilidozinc methyl, n-trifluoromethylanilidozinc methyl, trifluoromethoxyzinc ethyl, 2,2,2-trifluoroethoxyzinc ethyl, 1,1-di(trifluoromethyl)-2,2,2-trifluoroethoxyzinc ethyl, 2,2,2-trifluoro-1-trifluoromethylethoxyzinc ethyl, 2,2,3,3,3-pentafluoropropoxyzinc ethyl, 2,4,6-trifluorophenoxyzinc ethyl, 3,4,5-trifluorophenoxyzinc ethyl, pentafluorophenoxyzinc ethyl, 4-trifluoromethylphenoxyzinc ethyl, 4-trifluoromethylamidozinc ethyl, 2,2,2-trifluoroethylamidozinc ethyl, pentafluoroanilidozinc ethyl, N-trifluoromethylanilidozinc ethyl and the like.

In particular, the compound represented by the general formula [8] is preferably a bis(fluoroalkyloxy)zinc or a bis(fluoroaryloxy)zinc, and most preferably bis(2,2,2-trifluoro-1-trifluoromethylethoxy)zinc, bis(3,4,5-trifluorophenoxy) zinc, bis (pentafluorophenoxy) zinc or bis(1,1-di(trifluoromethyl)-2,2,2-trifluoroethoxy)zinc.

The production process of the compound represented by the above-mentioned general formula [8] is not specifically limited, and for example, a process of treating an organometallic compound such as an alkylmetal, a halogenated alkylmetal or the like with a compound represented by $LiX^1R^7i$ such as an alkyloxylithium compound having an electron-withdrawing substituent, an aryloxylithium compound having an electron-withdrawing substituent, an aminolithium compound having an electron-withdrawing substituent or the like, or a compound represented by $HX^1R^7i$ such as an alcohol having an electron-withdrawing substituent, a phenol having an electron-withdrawing substituent, an amine having an electron-withdrawing substituent or the like, is mentioned.

The treatment is preferably carried out under inert gas atmosphere. The treatment temperature is usually from −80° C. to 200° C., and preferably from −5° C. to 120° C. The treatment time is usually from 1 minute to 36 hours, and preferably from 10 minutes to 24 hours. Further, the treatment may use a solvent, and these compounds may be directly treated without using it. The solvent used is preferably an aliphatic hydrocarbon solvent, an aromatic hydrocarbon solvent or an ethereal solvent which is inert to the organometallic compound, the compound represented by $LiX^1R^7i$, the compound represented by $HX^1R^7i$ and the like.

Specific examples of the solvent is the same examples as specifically mentioned in the item of the compound [A].

Further, in the treatment, the order of dropwise addition of the organometallic compound, the compound represented by $LiX^1R^7i$ and the compound represented by $HX^1R^7i$ is not specifically limited, it may be successively dropwise added, may be simultaneously dropwise added, and 2 or more of solvents may be dropwise added after mixing. Arbitrary amounts of $(X^1R^7i)$ and $R^8$ can be introduced by adjusting the molar number of the compound represented by $LiX^1R^7i$ and the compound represented by $HX^1R^7i$ to the organometallic compound. Further, as a result of the treatment, the organometallic compound being a raw material, the compound represented by $LiX^1R^7i$, the compound represented by $HX^1R^7i$ and the like, may remain as unreacted matters. The compound represented by the general formula [8], which was obtained by the treatment can be used as a catalyst for addition polymerization after separation and purification such as recrystallization or the like, but the reacted solution can be also used as a catalyst component for addition polymerization. The solvent is preferably removed by distillation from the reacted solution, and drying is preferably carried out at a temperature of 25° C. or more for 1 hour or more under reduced pressure. It is more preferable to carry out drying at 60 to 200° C. for one to 24 hours, and most preferable at 80 to 160° C. for 4 to 18 hours.

Specific example of the production process of the compound represented by the general formula [8] is further shown below in detail when $M^4$ is a zinc atom and the treating agent is a phenol, include the following steps: hexane is used as a solvent; a hexane solution of a dialkylzinc (for example, diethylzinc) is added thereto and cooled at −78° C.; a hydrocarbon solution of the phenol which are 2-fold molar amount to the dialkylzinc is added dropwise; and the resulting mixture is stirred at room temperature for 10 minutes to 24 hours. Of course, those used in these treatments are not limited to the dialkylzinc and phenol.

Then, the compound [E] represented by the above-mentioned general formula [9] is illustrated.

$M^5$ has been already illustrated.

$X^2$ in the general formula [9] is the same as $X^1$ in the general formula [8] which has been already illustrated, and preferable elements are also the same as in $X^1$.

Further, "u" in the above-mentioned general formula [9] represents a valence of $X^2$, when $X^2$ is an atom of the Group XIV, "u" is 4, when $X^2$ is an atom of the Group XV, "u" is 3, and when $X^2$ is an atom of Group XVI, "u" is 2.

$R^9$ in the general formula [9] represents an electron-withdrawing group or a group containing an electron-withdrawing group, and when a plural number of $R^9$'s exist, they may be mutually the same or different. The exemplification of the electron-withdrawing group or the group containing an electron-withdrawing group is selected from those already described in the illustration of $R^1$ and $R^3$, and the preferable group is the same group as in $R^1$ and $R^3$. Specific example of $X^2R^9_{u-1}$ which is a combination of $X^2$ and $R^9$ and preferable specific example thereof are the same as the specific example $X^1R^7i$ which is previously illustrated when $X^2$ is a carbon atom, a nitrogen atom or an oxygen atom.

$R^{10}$ in the general formula [9] represents a hydrogen atom, a halogen atom or a hydrocarbon group, and when a plural number of $R^{10}$'s exist, they may be mutually the same or different.

Specific example and preferable specific example of $R^{10}$ are also the same as in $R^8$ in the general formula [8] which is previously described.

$T^4$ in the general formula [9] represents an atom of Group XIII of the Periodic Table. Specific examples thereof include a boron atom, an aluminum atom, a gallium atom and the like, and in particular, a boron atom is preferable. "m" in the general formula [9] represents a numeral satisfying $1 \leq m \leq 3$, and "m" is preferably 2. Two or more of molecules of the compound represented by the general formula [9] may be associated.

Among the compound represented by the general formula [9], specific examples of a case in which $M^5$ is a zinc atom include bis(fluoroalkyloxyzincoxy)alkylborane such as bis(trifluoromethoxyzincoxy)methylborane, bis(1,1,3,3,3-pentafluoro-2-trifluoromethylpropoxyzincoxy)methylborane and bis(2,2,2-trifluoro-1-trifluoromethylmethoxyzincoxy)methylborane; bis(fluoroalkyloxyzincoxy)alkylborane such as bis(2,2,2-trifluoroethoxyzincoxy)methylborane and bis(2,2,3,3,3-pentafluoropropoxyzincoxy)methylborane; bis(fluoroaryloxyzincoxy)alkylborane such as bis(2,4,6-trifluorophenoxyzincoxy)methylborane, bis(3,4,5-trifluorophenoxyzincoxy)methylborane and bis(pentafluorophenoxyzincoxy)methylborane; and bis(4-trifluoromethylphenoxyzincoxy)methylborane, bis(trifluoromethylamidozincoxy)methylborane, bis(2,2,2-trifluoroethylamidozincoxy)methylborane, bis(pentafluoroanilidozincoxy)methylborane, bis(N-trifluoromethylanilidozincoxy)methylborane and the like.

In particular, the compound represented by the general formula [9] is preferably a bis(fluoroalkyloxyzincoxy) alkylborane or a bis(fluoroaryloxyzincoxy)alkylborane, and further preferably bis(2,2,2-trifluoro-1-trifluoromethylethoxyzincoxy)methylborane, bis(3,4,5-trifluorophenoxyzincoxy)methylborane, bis(pentafluorophenoxyzincoxy)methylborane or bis(1,1,3,3,3-pentafluoro-2-trifluoromethylpropoxyzincoxy)methylborane.

The production process of the compound represented by the general formula [9] is not specifically limited, and for example, a process of treating the organometallic compound such as an alkylmetal, a halogenated alkylmetal or the like with an inorganic acid such as an alkylboric acid or the like, and thereafter, with the compound represented by $LiX^2R^9_{u-1}$ such as an alkyloxylithium compound, aryloxylithium compound or aminolithium compound having an electron-withdrawing substituent, or the compound represented by $HX^2R^9_{u-1}$ such as an alcohol, phenol or amine having an electron-withdrawing substituent or the like, is mentioned. A process of treating the organometallic compound such as an alkylmetal, a halogenated alkylmetal or the like with the compound selected from an alcohol, phenol or amine having an electron-withdrawing substituent, is preferable.

The treatment is preferably carried out under inert gas atmosphere. The treatment temperature is usually from $-100°$ C. to $200°$ C., and preferably from $-80°$ C. to $150°$ C. The treatment time is usually from 1 minute to 36 hours, and preferably from 10 minutes to 24 hours. Further, the treatment may use a solvent, and these compounds may be directly treated without using it. The solvent used is preferably an aliphatic hydrocarbon solvent, an aromatic hydrocarbon solvent or an ether-based compound which is inert to the organometallic compound, the compound represented by $LiX^2R^9_{u-1}$, the compound represented by $HX^2R^9_{u-1}$ and the like. Specific examples of the solvent is the same examples specifically mentioned in the item of the compound [A].

Further, in the treatment, the order of dropwise addition of the organometallic compound, the compound represented by $LiX^2R^9_{u-1}$ and the compound represented by $HX^2R^9_{u-1}$ is not specifically limited, it may be successively dropwise added, may be simultaneously dropwise added, and 2 or more of solvents may be dropwise added after mixing. Arbitrary amounts of $(X^2R^9_{u-1})$ and $R^{10}$ can be introduced by adjusting the molar number of the compound represented by $LiX^2R^9_{u-1}$ and the compound represented by $HX^2R^9_{u-1}$ to the organometallic compound. Further, as a result of the treatment, the organometallic compound being a raw material, the compound represented by $LiX^2R^9_{u-1}$, the compound represented by $HX^2R^9_{u-1}$ and the like may remain as unreacted matters. The compound represented by the general formula [9] which was obtained by the treatment can be used as a catalyst component for addition polymerization after carrying out separation and purification such as recrystallization or the like, but the reacted solution can be also used as a catalyst component for addition polymerization. The solvent is preferably removed by distillation from the reacted solution, and drying is preferably carried out at a temperature of $25°$ C. or more for 1 hour or more under reduced pressure. It is more preferable to carry out drying at 60 to $200°$ C. for one to 24 hours, and most preferable at 80 to $160°$ C. for 4 to 18 hours.

Specific example of the production process of the compound represented by the general formula [9] is further shown below in detail when $M^5$ is a zinc atom, an inorganic acid is an alkylboric acid and the treating agent is a phenol. A process that a toluene slurry of the alkylboric acid is cooled to $-78°$ C., a prescribed amount of a hexane solution of a dialkylzinc is added dropwise while vigorously stirring the slurry, the temperature of the mixture is gradually raised to room temperature after completion of dropwise addition, further stirring is carried out for a fixed time, a prescribed amount of phenols is gradually added dropwise, and further stirring is carried out for a fixed time, can be adopted.

Of course, compounds used in these treatments are not limited to the alkylboric acid, the dialkylzinc and the phenol.

The compounds [A] to [E] which are described above in detail are useful as the catalyst component for addition polymerization (particularly, catalyst component for olefin polymerization). Specific examples of the catalyst for addition polymerization of the present invention include a catalyst for addition polymerization obtained by contacting the compound (I) selected from the above-mentioned compounds [A] to [E] as a catalyst component for addition polymerization with the compound with a metal compound (II) of the Group III to the Group XII or lanthanide series, and a catalyst for addition polymerization obtained by contacting the catalyst component for addition polymerization (I), a metal compound (II) of the Group III to the Group XII or lanthanide series, and an organoaluminum compound (III).

Next, a catalyst for addition polymerization is described in detail below.

(II) Metal compound of the Groups III to XIII or Lanthanide Series

As the metal compound (II) of the Groups III to XII or Lanthanide Series used for addition polymerization catalyst of the present invention, a metal compound which is different from the above-described compound(I) is used, and it is not specifically limited so far as it is a metal compound of the Groups III to XIII or Lanthanide Series of the Periodic Table exhibiting an addition polymerization activity by using together with the compound(I), or compound(I) and an organoaluminum compound, as an activating co-catalyst component. Examples of the metal compound(II) includes metal compounds indicated by the general formula [10] described below, $\mu$-oxo type metal compounds and the like.

$$L_aMX_b \qquad [10]$$

(wherein M is a metal atom of the Group 3 to Group 13 or Lanthanide Series of the Periodic Table of the Elements; L is a group having a cyclopentadienyl type anion skeleton or a group containing a hetero-atom, a plurality of L groups may be the same or different, and a plurality of L groups may be optionally linked in direct, or through a group containing a carbon atom, a silicone atom, a nitrogen atom, an oxygen atom, a sulfur atom or a phosphorus atom; X is a halogen atom or a hydrocarbon group having 1 to 20 carbon atoms; a represents a numeral satisfying an expression of $0<a\leq 8$; b represents a numeral satisfying an expression of $0<b\leq 8$.)

In the general formula [10] representing the metal compound, M is a metal atom of the Group 3 to Group 13 of the Periodic Table (IUPAC 1985) or Lanthanide Series. Specific examples of the metal atom include a scandium atom, yttrium atom, titanium atom, zirconium atom, hafnium atom, vanadium atom, niobium atom, tantalum atom, chromium atom, iron atom, ruthenium atom, cobalt atom, rhodium atom, nickel atom, palladium atom, samarium atom, ytterbium atom, aluminum atom, boron atom and the like.

As the metal compound, M is preferably a transition metal compound, more preferably a titanium atom, zirconium atom or hafnium atom.

In the general formula [10], L is a group having a cyclopentadienyl type anion skeleton or a group containing a hetero-atom, and a plurality of L groups may be the same or different. Further, L groups may be optionally linked in direct, or through a group containing a carbon atom, a silicone atom, a nitrogen atom, an oxygen atom, a sulfur atom or a phosphorus atom.

A cyclopentadienyl type anion skeleton in L includes a cyclopentadienyl group, a substituted cyclopentadienyl group, an indenyl group, a substituted -indenyl group, a fluorenyl group, a substituted fluorenyl group and the like. Examples of the group having a cyclopentadiene type anion skeleton include an $\eta^5$-(substituted)cyclopentadienyl group, an $\eta^5$-(substituted)indenyl group, an $\eta^5$-(substituted) fluorenyl group and the like. Specific examples include an $\eta^5$-cyclopentadienyl group, an $\eta^5$-methylcyclopentadienyl group, an $\eta^5$-tert-butylcyclopentadienyl group, an $\eta^5$-1,2-dimethylcyclopentadienyl group, an $\eta^5$-1,3-dimethylcyclopentadienyl group, an $\eta^5$-1-tert-butyl-2-methylcyclopentadienyl group, an $\eta^5$-1-tert-butyl-3-methylcyclopentadienyl group, an $\eta^5$-1-methyl-2-isopropylcyclopentadienyl group, an $\eta^5$-1-methyl-3-isopropylcyclopentadienyl group, an $\eta^5$-1,2,3-trimethylcyclopentadienyl group, an $\eta^5$-1,2,4-trimethylcyclopentadienyl group, an $\eta^5$-tetramethylcyclopentadienyl group, an $\eta^5$-pentamethylcyclopentadienyl group, an $\eta^5$-indenyl group, an $\eta^5$-4,5,6,7-tetrahydroindenyl group, an $\eta^5$-2-methylindenyl group, an $\eta^5$-3-methylindenyl group, an $\eta^5$-4-methylindenyl group, an $\eta^5$-5-methylindenyl group, an $\eta^5$-6-methylindenyl group, an $\eta^5$-7-methylindenyl group, an $\eta^5$-2-tert-butylindenyl group, an $\eta^5$-3-tert-butylindenyl group, an $\eta^5$-4-tert-butylindenyl group, an $\eta^5$-5-tert-butylindenyl group, an $\eta^5$-6-tert-butylindenyl group, an $\eta^5$-7-tert-butylindenyl group, an $\eta^5$-2,3-dimethylindenyl group, an $\eta^5$-4,7-dimethylindenyl group, an $\eta^5$-2,4,7-trimethylindenyl group, an $\eta^5$-2-methyl-4-isopropylindenyl group, an $\eta^5$-4,5-benzindenyl group, an $\eta^5$-2-methyl-4,5-benzindenyl group, an $\eta^5$-2-4-phenylindenyl group, an $\eta^5$-2-methyl-5-phenylindenyl group, an $\eta^5$-2-methyl-4-phenylindenyl group, an $\eta^5$-2-methyl-4-naphthylindenyl group, an $\eta^5$-fluorenyl group, an $\eta^5$-2,7-dimethylfluorenyl group, an $\eta^5$-2,7-di-tert-butylfluorenyl group(herein-after, $\eta^5$ may be omitted for simplifying), and substitution products thereof, etc.

The hetero-atom in the group containing a hetero-atom includes an oxygen atom, a sulfur atom, a nitrogen atom, a phosphorus atom and the like, and examples thereof include an alkoxy group, an aryloxy group, a thioalkoxy group, a thioaryloxy group, an alkylamino group, an arylamino group, an alkylphosphino group, an arylphosphino group, or an aromatic or aliphatic heterocyclic group having an oxygen atom, a sulfur atom, a nitrogen atom and/or a phosphorus atom within the ring, and a chelating ligand.

Specific examples of the group containing a hetero-atom include a methoxy group, an ethoxy group, a n- or iso-propoxy group, a n-, sec-, iso- or tert-butoxy group, a phenoxy group, a 2-methylphenoxy group, a 2,6-dimethylphenoxy group, a 2,4,6-trimethylphenoxy group, a 2-ethylphenoxy group, a 4-n-propylphenoxy group, a 2-isopropylphenoxy group, a 2,6-diisopropylphenoxy group, a 4-sec-butylphenoxy group, a 4-tert-butylphenoxy group, a 2,6-di-sec-butylphenoxy group, a 4-tert-butyl-4-methylphenoxy group, a 2,6-di-tert-butylphenoxy group, a 4-methoxyphenoxy group, a 2,6-dimethoxyphenoxy group, a 3,5-dimethoxyphenoxy group, a 2-chlorophenoxy group, a 4-nitrosophenoxy group, a 4-nitrophenoxy group, a 2-aminophenoxy group, a 3-aminophenoxy group, a 4-aminothiophenoxy group, a 2,3,6-trichlorophenoxy group, a 2,4,6-trifluorophenoxy group, a thiomethoxy group, a dimethylamino group, a diethylamino group, a di-n- or iso-propylamino group, a diphenylamino group, an isopropylamino group, a tert-butylamino group, a pyrrolyl group, a dimethylphosphino group, a 2-(2-oxy-1-propyl)phenoxy group, catechol, resorcinol, 4-isopropylcatechol, 3-methoxycatechol, a 1,8-dihydroxynahpthyl group, a 1,2-dihydroxynahpthyl group, a 2,2'-biphenyldiol group, a 1,1'-bi-2-naphthol group, a 2,2'-dihydroxy-6,6'-dimethylbiphenyl group, a 4,4',6,6'-tetra-tert-butyl-2,2'-methylenediphenoxy group, a 4,4',6,6'-tetramethyl-2,2'-isobutylidenediphenoxy group and the like.

Further, the hetero atom-containing group includes a group represented by the formula [11]:

(wherein $R^a$ represents a hydrogen atom, halogen atom or hydrocarbon group, $R^a$ groups may be the same or different, and two of them may be bonded mutually and may form a ring.)

Specific Examples of $R^a$ include a hydrogen atom, fluorine atom, chlorine atom, bromine atom, iodine atom, methyl group, ethyl group, n-propyl group, isopropyl group, n-butyl group, tert-butyl group, cyclohexyl group, phenyl group, 1-naphtyl group, benzyl group and the like, but are not limited thereto.

Further, the hetero atom-containing group also includes a group represented by the general formula [12]:

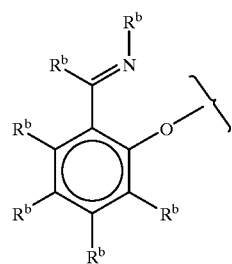

[12]

(wherein respective $R^b$ groups independently represent a hydrogen atom, halogen atom, hydrocarbon group, halogenated hydrocarbon group, hydrocarbon oxy group, silyl group or amino group, they may be the same or different, and two or more of them may be bonded mutually and may form a ring.)

Specific Examples of $R^b$ in the general formula [12] include a hydrogen atom, fluorine atom, chlorine atom, bromine atom, iodine atom, phenyl group, 1-naphtyl group, 2-naphtyl group, tert-butyl group, 2,6-dimethylphenyl group, 2-fluorenyl group, 2-methylphenyl group, 4-trifluoromethylphenyl group, 4-methoxyphenyl group, 4-pyridyl group, cyclohexyl group, 2-isopropylphenyl group, benzyl group, methyl group, triethylsilyl group, diphenylmethylsilyl group, 1-methy-1-phenylethyl group, 1,1-dimethyl propyl group, 2-chlorophenyl group and the like, but are not limited thereto.

Further, the chelating ligand means a ligand having a plural number of coordinating positions, and specific examples thereof include an acetylacetonate, diimine, oxazoline, bisoxazoline, terpyridine, acylhydrazone, diethylenetriamine, triethylenetetramine, porphyrin, crown ether, cryptate and the like.

The mutual groups having the cyclopentadienyl type anion skeleton, the group having a cyclopentadienyl type anion skeleton and the group containing a hetero-atom, or the mutual groups containing a hetero-atom may be directly linked, or may be linked through a group containing a carbon atom, a silicone atom, a nitrogen atom, an oxygen atom, a sulfur atom or a phosphorus atom, respectively. Examples of the group include alkylene groups such as an ethylene group, a propylene group and the like, substituted alkylene groups such as a dimethylmethylene group, a diphenylmethylene group and the like, or a silylene group, substituted silylene groups such as a dimethylsilylene group, a diphenylsilylene group, a tetramethyldisilylene group and the like, or hetero-atoms such as a nitrogen atom, an oxygen atom, a sulfur atom and/or a phosphorus atom and the like, etc.

X in the general formula [10] representing the transition metal compound is a halogen atom or a hydrocarbon group having 1 to 24 carbon atoms. Specific examples of X include a halogen atom such as a fluorine atom, chlorine atom, bromine atom, and iodine atom and hydrocarbon group having 1 to 24 carbon atoms such as a methyl group, ethyl group, n-propyl group, isopropyl group, n-butyl group, phenyl group, benzyl group and the like, and preferably include a halogen atom, alkyl group having 1 to 24 carbon atoms and aralkyl group having 7 to 24 carbon atoms.

In the general formula [10], "a" represents a numeral satisfying an expression of $0<a\leqq8$, "b" represents a numeral satisfying an expression of $0<b\leqq8$, and "a" and "b" are properly selected depending on the valency of M.

Among the metal compounds(II), specific examples of the compound in which a metal atom is a titanium atom include bis(cyclopentadienyl)titanium dichloride, bis(methylcyclopentadienyl)titanium dichloride, bis(n-butylcyclopentadienyl)titanium dichloride, bis(dimethylcyclopentadienyl)titanium dichloride, bis(ethylmethylcyclopentadienyl)titanium dichloride, bis(trimethylcyclopentadienyl)titanium dichloride, bis(tetramethylcyclopentadienyl)titanium dichloride, bis(pentamethylcyclopentadienyl)titanium dichloride, bis(indenyl)titanium dichloride, bis(4,5,6,7-tetrahydroindenyl)titanium dichloride, bis(fluorenyl)titanium dichloride, cyclopentadienyl(pentamethylcyclopentadienyl) titanium dichloride, cyclopentadienyl(indenyl) titanium dichloride, cyclopentadienyl(fluorenyl) titanium dichloride, indenyl(fluorenyl)titanium dichloride, pentamethylcyclopentadienyl (indenyl)titanium dichloride, pentamethylcyclopentadienyl(fluorenyl)titanium dichloride, ethylenebis(cyclopentadienyl)titanium dichloride, ethylenebis(2-methylcyclopentadienyl)titanium dichloride, ethylenebis(3-methylcyclopentadienyl)titanium dichloride, ethylenebis(2-n-butylcyclopentadienyl)titanium dichloride, ethylenebis(3-n-butylcyclopentadienyl)titanium dichloride, ethylenebis(2,3-dimethylcyclopentadienyl)titanium dichloride, ethylenebis(2,4-dimethylcyclopentadienyl)titanium dichloride, ethylenebis(2,5-dimethylcyclopentadienyl) titanium dichloride, ethylenebis(3,4-dimethylcyclopentadienyl)titanium dichloride, ethylenebis(2,3-ethylmethylcyclopentadienyl)titanium dichloride, ethylenebis(2,4-ethylmethylcyclopentadienyl)titanium dichloride, ethylenebis(2,5-ethylmethylcyclopentadienyl) titanium dichloride, ethylenebis(3,5-ethylmethylcyclopentadienyl)titanium dichloride, ethylenebis(2,3,4-trimethylcyclopentadienyl)titanium dichloride, ethylenebis(2,3,5-trimethylcyclopentadienyl)titanium dichloride, ethylenebis(tetramethylcyclopentadienyl) titanium dichloride, ethylenebis(indenyl)titanium dichloride, ethylenebis(4,5,6,7-tetrahydroindenyl)titanium dichloride, ethylenebis(2-phenylindenyl)titanium dichloride, ethylenebis(2-methylindenyl)titanium dichloride, ethylenebis(2-methyl-4-phenylindenyl)titanium dichloride, ethylenebis(2-methyl-4-naphthylindenyl)titanium dichloride, ethylenebis(2-methyl-4,5-benzoindenyl)titanium dichloride, ethylenebis(fluorenyl)titanium dichloride, ethylene(cyclopentadienyl) (pentamethylcyclopentadienyl) titanium dichloride, ethylene(cyclopentadienyl)(indenyl) titanium dichloride, ethylene(methylcyclopentadienyl) (indenyl)titanium dichloride, ethylene(n-butylcyclopentadienyl)(indenyl)titanium dichloride, ethylene(tetramethylcyclopentadienyl) (indenyl)titanium dichloride, ethylene(cyclopentadienyl)(fluorenyl)titanium dichloride, ethylene(methylcyclopentadienyl) (fluorenyl) titanium dichloride, ethylene (pentamethylcyclopentadienyl)(fluorenyl)titanium dichloride, ethylene (n-butylcyclopentadienyl) (fluorenyl)titanium dichloride, ethylene (tetramethylpentadienyl)(fluorenyl)titanium dichloride, ethylene(indenyl)(fluorenyl)titanium dichloride, isopropylidenebis(cyclopentadienyl) titanium dichloride, isopropylidenebis(2-methylcyclopentadienyl)titanium dichloride, isopropylidenebis(3-methylcyclopentadienyl) titanium dichloride, isopropylidenebis(2-n-butylcyclopentadienyl)titanium dichloride, isopropylidenebis(3-n-butylcyclopentadienyl)titanium dichloride, isopropylidenebis(2,3-dimethylcyclopentadienyl)titanium dichloride, isopropylidenebis(2,4-dimethyl- cyclopentadienyl)titanium dichloride, isopropylidenebis(2,5-dimethyl- cyclopentadienyl)titanium dichloride, isopropylidenebis(3,4-dimethylcyclopentadienyl)titanium dichloride, isopropylidenebis(2,3-ethylmethyl- cyclopentadienyl)titanium dichloride, isopropylidenebis(2,4-ethylmethylcyclopentadienyl) titanium dichloride, isopropylidenebis(2,5-ethylmethylcyclopentadienyl)titanium dichloride, isopropylidenebis(3,5-ethylmethylcyclopentadienyl) titanium dichloride, isopropylidenebis(2,3,4-trimethylcyclopentadienyl)titanium dichloride, isopropylidenebis(2,3,5-trimethyl-cyclopentadienyl) titanium dichloride, isopropylidenebis (tetramethylcyclopentadienyl)-titanium dichloride, isopropylidenebis(indenyl) titanium dichloride, isopropylidenebis(4,5,6,7-tetrahydroindenyl)titanium dichloride, isopropylidenebis(2-phenylindenyl)titanium dichloride, isopropylidenebis(2-methylindenyl)titanium dichloride, isopropylidenebis(2-methyl-4-phenylindenyl) titanium dichloride, isopropylidenebis(2-methyl-4-naphthylindenyl)titanium dichloride, isopropylidenebis(2-methyl-4,5-benzoindenyl)titanium dichloride, isopropylidenebis(fluorenyl)titanium dichloride, isopropylidene(cyclopentadienyl) (tetramethylcyclopentadienyl)titanium dichloride, isopropylidene (cyclopentadienyl)(indenyl)titanium dichloride, isopropylidene(methylcyclopentadienyl) (indenyl)titanium dichloride, isopropylidene(n-butylcyclopentadienyl) (indenyl)titanium dichloride, isopropylidene (tetramethylcyclopentadienyl) (indenyl)titanium dichloride, isopropylidene (cyclopentadienyl)(fluorenyl)titanium dichloride, isopropylidene(methylcyclopentadienyl) (fluorenyl)titanim dichloride, isopropylidene(n-butylcyclopentadienyl) (fluorenyl) titanium dichloride, isopropylidene (tetramethylcyclopentadienyl) (fluorenyl) titanium dichloride, isopropylidene (indenyl)(fluorenyl) titanium dichloride, dimethylsilylenebis(cyclopentadienyl)titanium dichloride, dimethylsilylenebis(2-methylcyclopentadienyl) titanium dichloride, dimethylsilylenebis(3-methylcyclopentadienyl)titanium dichloride, dimethylsilylenebis(2-n-butylcyclopentadienyl)titanium dichloride, dimethylsilylenebis(3-n-butylcyclopentadienyl) titanium dichloride, dimethylsilylenebis(2,3-dimethylcyclopentadienyl)titanium dichloride, dimethylsilylenebis(2,4-dimethylcyclopentadienyl)titanium dichloride, dimethylsilylenebis(2,5-dimethylcyclopentadienyl)titanium dichloride, dimethylsilylenebis (3,4-dimethylcyclopentadienyl)titanium dichloride, dimethylsilylenebis(2,3-ethylmethylcyclopentadienyl) titanium dichloride, dimethylsilylenebis(2,4-ethylmethylcyclopentadienyl)titanium dichloride, dimethylsilylenebis(2,5-ethylmethylcyclopentadienyl) titanium dichloride, dimethylsilylenebis(3,5-ethylmethylcyclopentadienyl)titanium dichloride, dimethylsilylenebis(2,3,4-trimethylcyclopentadienyl) titanium dichloride, dimethylsilylenebis(2,3,5-trimethylcyclopentadienyl)titanium dichloride, dimethylsilylenebis(tetramethylcyclopentadienyl)-titanium dichloride, dimethylsilylenebis(indenyl)titanium dichloride, dimethylsilylenebis(4,5,6,7-tetrahydroindenyl)titanium dichloride, dimethylsilylenebis(2-methylindenyl)titanium dichloride, dimethylsilylenebis(2-methyl-4-phenylindenyl) titanium dichloride, dimethylsilylenebis(2-methyl-4-naphthylindenyl)titanium dichloride, dimethylsilylenebis(2-methyl-4,5-benzoindenyl)titanium dichloride, dimethylsilylene(cyclopentadienyl)(indenyl)titanium dichloride, dimethylsilylene(methylcyclopentadienyl) (indenyl)titanium dichloride, dimethylsilylene(n-butylcyclopentadienyl)(indenyl)titanium dichloride, dimethylsilylene(tetramethylcyclopentadienyl) (indenyl) titanium dichloride, dimethylsilylene (cyclopentadienyl) (fluorenyl)titanium dichloride, dimethylsilylene (methylcyclopentadienyl)(fluorenyl) titanium dichloride, dimethylsilylene(n-butylcyclopentadienyl) (fluorenyl) titanium dichloride, dimethylsilylene-(tetramethylcyclopentadienyl) (indenyl)titanium dichloride, dimethylsilylene-(indenyl)(fluorenyl)titanium dichloride, cyclopentadienyltitanium trichloride, pentamethylcyclopentadienyltitanium trichloride, cyclopentadienyl (dimethylamido)titanium dichloride, cyclopentadienyl (phenoxy)titanium dichloride, cyclopentadienyl(2,6-dimethylphenyl)titanium dichoride, cyclopentadienyl (2,6-d-isopropylphenyl)titanium dichloride, cyclopentadienyl(2, 6-di-tert-butylphenyl)titanium dichloride, pentamethylcyclopentadienyl(2,6-dimethylphenyl)titanium dichloride, pentamethylcyclopentadienyl(2,6-disopropylphenyl)titanium dichloride, pentamethylcyclopentadienyl(2,6-di-tert-butylphenyl)titanium dichloride, indenyl(2,6-diisopropylphenyl)titanium dichloride, fluorenyl-(2,6-diisopropylphenyl)titanium dichloride, methylene(cyclopentadienyl)(3,5-dimethyl-2-phenoxy)titanium dichloride, methylene(cyclopentadienyl) (3-tert-butyl-2-phenoxy)titanium dichloride, methylene (cyclopentadienyl)(3-tert-butyl-5-methyl-2-phenoxy) titanium dichloride, methylene(cyclopentadienyl)(3-phenyl-2-phenoxy)titanium dichloride, methylene (cyclopentadienyl)(3-tert-butyldimethylsilyl-5-methyl-2-phenoxy)titanium dichloride, methylene(cyclopentadienyl) (3-trimethylsilyl-5-methyl-2-phenoxy)titanium dichloride, methylene(cyclopentadienyl)(3-tert-butyl-5-methoxy-2-phenoxy)titanium dichloride, methylene(cyclopentadienyl) (3-tert-butyl-5-chloro-2-phenoxy)titanium dichloride, methylene(methylcyclopentadienyl)(3,5-dimethyl-2-phenoxy)titanium dichloride, methylene (methylcyclopentadienyl)(3-tert-butyl-2-phenoxy)titanium dichloride, methylene(methylcyclopentadienyl)(3-tert-butyl-5-methyl-2-phenoxy)titanium dichloride, methylene (methylcyclopentadienyl)(3-phenyl-2-phenoxy)titanium dichloride, methylene(methylcyclopentadienyl)(3-tert-butyldimethylsilyl-5-methyl-2-phenoxy)titanium dichloride, methylene(methylcyclopentadienyl)(3-trimethylsilyl-5-methyl-2-phenoxy)titanium dichloride, methylene(methylcyclopentadienyl)(3-tert-butyl-5-methoxy-2-phenoxy)titanium dichloride, methylene (methylcyclopentadienyl)(3-tert-butyl-5-chloro-2-phenoxy) titanium dichloride, methylene(tert-butylcyclopentadienyl) (3,5-dimethyl-2-phenoxy)titanium dichloride, methylene (tert-butylcyclopentadienyl)(3-tert-butyl-2-phenoxy) titanium dichloride, methylene(tert-butylcyclopentadienyl) (3-tert-butyl-5-methyl-2-phenoxy)titanium dichloride, methylene(tert-butylcyclopentadienyl)(3-phenyl-2-phenoxy)titanium dichloride, methylene(tert-butylcyclopentadienyl)(3-tert-butyldimethylsilyl-5-methyl-2-phenoxy)titanium dichloride, methylene(tert-butylcyclopentadienyl)(3-trimethylsilyl-5-methyl-2-phenoxy)titanium dichloride, methylene(tert-butylcyclopentadienyl)(3-tert-butyl-5-methoxy-2-phenoxy) titanium dichloride, methylene(tert-butylcyclopentadienyl) (3-tert-butyl-5-chloro-2-phenoxy)titanium dichloride, methylene(tetramethylcyclopentadienyl)(3,5-dimethyl-2-phenoxy)titanium dichloride, methylene (tetramethylcyclopentadienyl)(3-tert-butyl-2-phenoxy) titanium dichloride, methylene(tetramethyl-cyclopentadienyl)(3-tert-butyl-5-methyl-2-phenoxy) titanium dichloride, methylene(tetramethylcyclopentadienyl)(3-phenyl-2-phenoxy)titanium dichloride, methylene(tetramethylcyclopentadienyl)(3-tert-butyldimethylsilyl-5-methyl-2-phenoxy)titanium dichloride, methylene(tetramethylcyclopentadienyl) (3-trimethylsilyl-5-methyl-2-phenoxy)titanium dichloride, methylene(tetramethylcyclopentadienyl) (3-tert-butyl-5-methoxy-2-phenoxy)titanium dichloride, methylene (tetramethylcyclopentadienyl) (3-tert-butyl-5-chloro-2-phenoxy) titanium dichloride, methylene (trimethylsilylcyclopentadienyl)(3,5-dimethyl-2-phenoxy) titanium dichloride, methylene(trimethylsilylcyclopentadienyl)(3-tert-butyl-2-phenoxy)titanium dichloride, methylene(trimethylsilylcyclopentadienyl)(3-tert-butyl-5-methyl-2-phenoxy)titanium dichloride, methylene(trimethylsilylcyclopentadienyl)(3-phenyl-2- phenoxy)titanium dichloride, methylene(trimethylsilylcyclopentadienyl)(3-tert-butyldimethylsilyl-5-methyl-2-phenoxy)titanium dichloride, methylene(trimethylsilylcyclopentadienyl)(3-trimethylsilyl-5-methyl-2-phenoxy)titanium dichloride, methylene(trimethylsilylcyclopentadienyl)(3-tert-butyl-5-methoxy-2-phenoxy)titanium dichloride, methylene(trimethylsilylcyclopentadienyl)(3-tert-butyl-5-chloro-2-phenoxy)titanium dichloride, methylene(fluorenyl)(3,5-dimethyl-2-phenoxy)titanium dichloride, methylene(fluorenyl)(3-tert-butyl-2-phenoxy)titanium dichloride, methylene(fluorenyl)(3-tert-butyl-5-methyl-2-phenoxy)titanium dichloride, methylene(fluorenyl)(3-phenyl-2-phenoxy)titanium dichloride, methylene(fluorenyl)(3-tert-butyldimethylsilyl-5-methyl-2-phenoxy)titanium dichloride, methylene(fluorenyl)(3-trimethylsilyl-5-methyl-2-phenoxy)titanium dichloride, methylene(fluorenyl)(3-tert-butyl-5-methoxy-2-phenoxy)titanium dichloride, methylene(fluorenyl)(3-tert-butyl-5-chloro-2-phenoxy)titanium dichloride, isopropylidene(cyclopentadienyl)(3,5-dimethyl-2-phenoxy)titanium dichloride, isopropylidene(cyclopentadienyl)(3-tert-butyl-2-phenoxy)titanium dichloride, isopropylidene(cyclopentadienyl)(3-tert-butyl-5-methyl-2-phenoxy)titanium dichloride, isopropylidene(cyclopentadienyl)(3-phenyl-2-phenoxy)titanium dichloride, isopropylidene(cyclopentadienyl)(3-tert-butyldimethylsilyl-5-methyl-2-phenoxy)titanium dichloride, isopropylidene(cyclopentadienyl)(3-trimethylsilyl-5-methyl-2-phenoxy)titanium dichloride, isopropylidene(cyclopentadienyl)(3-tert-butyl-5-methoxy-2-phenoxy)titanium dichloride, isopropylidene(cyclopentadienyl)(3-tert-butyl-5-chloro-2-phenoxy)titanium dichloride, isopropylidene(methylcyclopentadienyl)(3,5-dimethyl-2-phenoxy)titanium dichloride, isopropylidene(methylcyclopentadienyl)(3-tert-butyl-2-phenoxy)titanium dichloride, isopropylidene(methylcyclopentadienyl)(3-tert-butyl-5-methyl-2-phenoxy)titanium dichloride, isopropylidene(methylcyclopentadienyl)(3-phenyl-2-phenoxy)titanium dichloride, isopropylidene(methylcyclopentadienyl)(3-tert-butyldimethylsilyl-5-methyl-2-phenoxy)titanium dichloride, isopropylidene(methylcyclopentadienyl)(3-trimethylsilyl-5-methyl-2-phenoxy)titanium dichloride, isopropylidene(methylcyclopentadienyl)(3-tert-butyl-5-methoxy-2-phenoxy)titanium dichloride, isopropylidene(methylcyclopentadienyl)(3-tert-butyl-5-chloro-2-phenoxy)titanium dichloride, isopropylidene(tert-butylcyclopentadienyl)(3,5-dimethyl-2-phenoxy)titanium dichloride, isopropylidene(tert-butylcyclopentadienyl)(3-tert-butyl-2-phenoxy)titanium dichloride, isopropylidene(tert-butylcyclopentadienyl)(3-tert-butyl-5-methyl-2-phenoxy)titanium dichloride, isopropylidene(tert-butylcyclopentadienyl)(3-phenyl-2-phenoxy)titanium dichloride, isopropylidene(tert-butylcyclopentadienyl)(3-tert-butyldimethylsilyl-5-methyl-2-phenoxy)titanium dichloride, isopropylidene(tert-butylcyclopentadienyl)(3-trimethylsilyl-5-methyl-2-phenoxy)titanium dichloride, isopropylidene(tert-butylcyclopentadienyl)(3-tert-butyl-5-methoxy-2-phenoxy)titanium dichloride, isopropylidene(tert-butylcyclopentadienyl)(3-tert-butyl-5-chloro-2-phenoxy)titanium dichloride, isopropylidene(tetramethylcyclopentadienyl)(3,5-dimethyl-2-phenoxy)titanium dichloride, isopropylidene(tetramethylcyclopentadienyl)(3-tert-butyl-2-phenoxy)titanium dichloride, isopropylidene(tetramethylcyclopentadienyl)(3-tert-butyl-5-methyl-2-phenoxy)titanium dichloride, isopropylidene(tetramethylcyclopentadienyl)(3-phenyl-2-phenoxy)titanium dichloride, isopropylidene(tetramethylcyclopentadienyl)(3-tert-butyldimethylsilyl-5-methyl-2-phenoxy)titanium dichloride, isopropylidene(tetramethylcyclopentadienyl)(3-trimethylsilyl-5-methyl-2-phenoxy)titanium dichloride, isopropylidene(tetramethylcyclopentadienyl)(3-tert-butyl-5-methoxy-2-phenoxy)titanium dichloride, isopropylidene(tetramethylcyclopentadienyl)(3-tert-butyl-5-chloro-2-phenoxy)titanium dichloride, isopropylidene(trimethylsilylcyclopentadienyl)(3,5-dimethyl-2-phenoxy)titanium dichloride, isopropylidene(trimethylsilylcyclopentadienyl)(3-tert-butyl-2-phenoxy)titanium dichloride, isopropylidene(trimethylsilylcyclopentadienyl)(3-tert-butyl-5-methyl-2-phenoxy)titanium dichloride, isopropylidene(trimethylsilylcyclopentadienyl)(3-phenyl-2-phenoxy)titanium dichloride, isopropylidene(trimethylsilylcyclopentadienyl)(3-tert-butyldimethylsilyl-5-methyl-2-phenoxy)titanium dichloride, isopropylidene(trimethylsilylcyclopentadienyl)(3-trimethylsilyl-5-methyl-2-phenoxy)titanium dichloride, isopropylidene(trimethylsilylcyclopentadienyl)(3-tert-butyl-5-methoxy-2-phenoxy)titanium dichloride, isopropylidene(trimethylsilylcyclopentadienyl)(3-tert-butyl-5-chloro-2-phenoxy)titanium dichloride, isopropylidene(fluorenyl)(3,5-dimethyl-2-phenoxy)titanium dichloride, isopropylidene(fluorenyl)(3-tert-butyl-2-phenoxy)titanium dichloride, isopropylidene(fluorenyl)(3-tert-butyl-5-methyl-2-phenoxy)titanium dichloride, isopropylidene(fluorenyl)(3-phenyl-2-phenoxy)titanium dichloride, isopropylidene(fluorenyl)(3-tert-butyldimethylsilyl -5-methyl-2-phenoxy)titanium dichloride, isopropylidene(fluorenyl)(3-trimethylsilyl-5-methyl-2-phenoxy)titanium dichloride, isopropylidene(fluorenyl)(3-tert-butyl-5-methoxy-2phenoxy)titanium dichloride, isopropylidene(fluorenyl)(3-tert-butyl-5-chloro-2-phenoxy)titanium dichloride, diphenylmethylene(cyclopentadienyl)(3,5-dimethyl-2-phenoxy)titanium dichloride, diphenylmethylene(cyclopentadienyl)(3-tert-butyl-2-phenoxy)titanium dichloride, diphenylmethylene(cyclopentadienyl)(3-tert-butyl-5-methyl-2-phenoxy)titanium dichloride, diphenylmethylene(cyclopentadienyl)(3-phenyl-2-phenoxy)titanium dichloride, diphenylmethylene(cyclopentadienyl)(3-tert-butyldimethylsilyl-5-methyl-2-phenoxy)titanium dichloride, diphenylmethylene(cyclopentadienyl)(3-trimethylsilyl-5-methyl-2-phenoxy)titanium dichloride, diphenylmethylene(cyclopentadienyl)(3-tert-butyl-5-methoxy-2-phenoxy)titanium dichloride, diphenylmethylene(cyclopentadienyl)(3-tert-butyl-5-chloro-2-phenoxy)titanium dichloride, diphenylmethylene(methylcyclopentadienyl)(3,5-dimethyl-2-phenoxy)titanium dichloride, diphenylmethylene(methylcyclopentadienyl)(3-tert-butyl-2-phenoxy)titanium dichloride, diphenylmethylene(methylcyclopentadienyl)(3-tert-butyl-5-methyl-2-phenoxy)titanium dichloride, diphenylmethylene(methylcyclopentadienyl)(3-phenyl-2-phenoxy)titanium dichloride, diphenylmethylene(methylcyclopentadienyl)(3-tert-butyldimethylsilyl-5-methyl-2-phenoxy)titanium dichloride, diphenylmethylene(methylcyclopentadienyl)(3-trimethylsilyl-5-methyl-2-phenoxy)titanium dichloride, diphenylmethylene (methylcyclopentadienyl)(3-tert-butyl-5-methoxy-2-phenoxy)titanium dichloride, diphenylmethylene(methylcyclopentadienyl)(3-tert-butyl-5-chloro-2-phenoxy)titanium dichloride, diphenylmethylene(tert-butylcyclopentadienyl)(3,5-dimethyl-2-phenoxy)titanium dichloride, diphenylmethylene(tert-butylcyclopentadienyl)(3-tert-butyl-2-phenoxy)titanium dichloride, diphenylmethylene(tert-butylcyclopentadienyl)(3-tert-butyl-5-methyl-2-phenoxy)titanium dichloride, diphenylmethylene(tert-butylcyclopentadienyl)(3-phenyl-2-phenoxy)titanium dichloride, diphenylmethylene(tert-butylcyclopentadienyl)(3-tert-butyldimethylsilyl-5-methyl-2-phenoxy)titanium dichloride, diphenylmethylene(tert-butylcyclopentadienyl)(3-trimethylsilyl-5-methyl-2-phenoxy)titanium dichloride, diphenylmethylene(tert-butylcyclopentadienyl)(3-tert-butyl-5-methoxy-2-phenoxy)titanium dichloride, diphenylmethylene(tert-butylcyclopentadienyl)(3-tert-butyl-5-chloro-2-phenoxy)titanium dichloride, diphenylmethylene(tetramethylcyclopentadienyl)(3,5-dimethyl-2-phenoxy)titanium dichloride, diphenylmethylene(tetramethylcyclopentadienyl)(3-tert-butyl-2-phenoxy)titanium dichloride, diphenylmethylene(tetramethylcyclopentadienyl)(3-tert-butyl-5-methyl-2-phenoxy)titanium dichloride, diphenylmethylene(tetramethylcyclopentadienyl)(3-phenyl-2-phenoxy)titanium dichloride, diphenylmethylene(tetramethylcyclopentadienyl)(3-tert-butyldimethylsilyl-5-methyl-2-phenoxy)titanium dichloride, diphenylmethylene(tetramethylcyclopentadienyl)(3-trimethylsilyl-5-methyl-2-phenoxy)titanium dichloride, diphenylmethylene(tetramethylcyclopentadienyl)(3-tert-butyl-5-methoxy-2-phenoxy)titanium dichloride, diphenylmethylene(tetramethylcyclopentadienyl)(3-tert-butyl-5-chloro-2-phenoxy)titanium dichloride, diphenylmethylene(trimethylsilylcyclopentadienyl)(3,5-dimethyl-2-phenoxy)titanium dichloride, diphenylmethylene(trimethylsilylcyclopentadienyl)(3-tert-butyl-2-phenoxy)titanium dichloride, diphenylmethylene(trimethylsilylcyclopentadienyl)(3-tert-butyl-5-methyl-2-phenoxy)titanium dichloride, diphenylmethylene(trimethylsilylcyclopentadienyl)(3-phenyl-2-phenoxy)titanium dichloride, diphenylmethylene(trimethylsilylcyclopentadienyl)(3-tert-butyldimethylsilyl-5-methyl-2-phenoxy)titanium dichloride, diphenylmethylene(trimethylsilylcyclopentadienyl)(3-trimethylsilyl-5-methyl-2-phenoxy)titanium dichloride, diphenylmethylene(trimethylsilylcyclopentadienyl)(3-tert-butyl-5-methoxy-2-phenoxy)titanium dichloride, diphenylmethylene(trimethylsilylcyclopentadienyl)(3-tert-butyl-5-chloro-2-phenoxy)titanium dichloride, diphenylmethylene(fluorenyl)(3,5-dimethyl-2-phenoxy)titanium dichloride, diphenylmethylene(fluorenyl)(3-tert-butyl-2-phenoxy)titanium dichloride, diphenylmethylene(fluorenyl)(3-tert-butyl-5-methyl-2-phenoxy)titanium dichloride, diphenylmethylene(fluorenyl)(3-phenyl-2-phenoxy)titanium dichloride, diphenylmethylene(fluorenyl)(3-tert-butyldimethylsilyl-5-methyl-2-phenoxy)titanium dichloride, diphenylmethylene(fluorenyl)(3-trimethylsilyl-5-methyl-2-phenoxy)titanium dichloride, diphenylmethylene(fluorenyl)(3-tert-butyl-5-methoxy-2-phenoxy)titanium dichloride, diphenylmethylene(fluorenyl)(3-tert-butyl-5-chloro-2-phenoxy)titanium dichloride, dimethylsilylene(cyclopentadienyl)(2-phenoxy)titanium dichloride, dimethylsilylene-(cyclopentadienyl)(3-methyl-2-phenoxy)titanium dichloride, dimethylsilylene(cyclopentadienyl)(3,5-dimethyl-2-phenoxy)titanium dichloride, dimethylsilylene(cyclopentadienyl)(3-tert-butyl-2-phenoxy)titanium dichloride, dimethylsilylene(cyclopentadienyl)(3-tert-butyl-5-methyl-2-phenoxy)titanium dichloride, dimethylsilylene(cyclopentadienyl)(3,5-di-tert-butyl-2-phenoxy)titanium dichloride, dimethylsilylene(cyclopentadienyl)(5-methyl-3-phenyl-2-phenoxy)titanium dichloride, dimethylsilylene(cyclopentadienyl)(3-tert-butyldimethylsilyl-5-methyl-2-phenoxy)titanium dichloride, dimethylsilylene(cyclopentadienyl)(5-methyl-3-trimethylsilyl-2-phenoxy)titanium dichloride, dimethylsilylene(cyclopentadienyl)(3-tert-butyl-5-methoxy-2-phenoxy)titanium dichloride, dimethylsilylene(cyclopentadienyl)(3-tert-butyl-5-chloro-2-phenoxy)titanium dichloride, dimethylsilylene(cyclopentadienyl)(3,5-diamyl-2-phenoxy)titanium dichloride, dimethylsilylene(methylcyclopentadienyl)(2-phenoxy)titanium dichloride, dimethylsilylene(methylcyclopentadienyl)(3-methyl-2-phenoxy)titanium dichloride, dimethylsilylene(methylcyclopentadienyl)(3,5-dimethyl-2-phenoxy)titanium dichloride, dimethylsilylene(methylcyclopentadienyl)(3-tert-butyl-2-phenoxy)titanium dichloride, dimethylsilylene(methylcyclopentadienyl)(3-tert-butyl-5-methyl-2-phenoxy)titanium dichloride, dimethylsilylene(methylcyclopentadienyl)(3,5-di-tert-butyl-2-phenoxy)titanium dichloride, dimethylsilylene(methylcyclopentadienyl)(5-methyl-3-phenyl-2-phenoxy)titanium dichloride, dimethylsilylene(methyl-cyclopentadienyl)(3-tert-butyldimethylsilyl-5-methyl-2-phenoxy)titanium dichloride, dimethylsilylene(methylcyclopentadienyl)(5-methyl-3-trimethylsilyl-2-phenoxy)titanium dichloride, dimethylsilylene(methylcyclopentadienyl)(3-tert-butyl-5-methoxy-2-phenoxy)titanium dichloride, dimethylsilylene(methylcyclopentadienyl)(3-tert-butyl-5-chloro-2-phenoxy)titanium dichloride, dimethylsilylene(methyl-cyclopentadienyl)(3,5-diamyl-2-phenoxy)titanium dichloride, dimethylsilylene(n-butylcyclopentadienyl)(2-phenoxy)titanium-dichloride, dimethylsilylene(n-butylcyclopentadienyl)(3-methyl-2-phenoxy)titanium dichloride, dimethylsilylene(n-butylcyclopentadienyl)(3,5-dimethyl-2-phenoxy)titanium dichloride, dimethylsilylene(n-butylcyclopentadienyl)(3-tert-butyl-2-phenoxy)titanium dichloride, dimethylsilylene(n-butylcyclopentadienyl)(3-tert-butyl-5-methyl-2-phenoxy)titanium dichloride, dimethylsilylene(n-butylcyclopentadienyl)(3,5-di-tert-butyl-2-phenoxy)titanium dichloride, dimethylsilylene(n-butylcyclopentadienyl)(5-methyl-3-phenyl-2-phenoxy)titanium dichloride, dimethylsilylene(n-butylcyclopentadienyl)(3-tert-butyldimethylsilyl-5-methyl-2-phenoxy)titanium dichloride, dimethylsilylene(n-butylcyclopentadienyl)(5-methyl-3-trimethylsilyl-2-phenoxy)titanium dichloride, dimethylsilylene(n-butylcyclopentadienyl)(3-tert-butyl-5-methoxy-2-phenoxy)titanium dichloride, di-methylsilylene(n-butylcyclopentadienyl)(3-tert-butyl-5-chloro-2-phenoxy)titanium dichloride, dimethylsilylene(n-butylcyclopentadienyl)(3,5-diamyl-2-phenoxy)titanium dichloride, dimethylsilylene(tert-butylcyclopentadienyl)(2-phenoxy)titanium dichloride, dimethylsilylene(tert-butylcyclopentadienyl)(3-methyl-2-phenoxy)titanium dichloride, dimethylsilylene(tert-butylcyclopentadienyl)(3,5-dimethyl-2-phenoxy)titanium dichloride, dimethylsilylene(tert-butylcyclopentadienyl)(3-tert-butyl-2-phenoxy)titanium dichloride, dimethylsilylene(tert-butylcyclopentadienyl)(3-tert-butyl-5-methyl-2-phenoxy)titanium dichloride, dimethylsilylene(tert-butylcyclopentadienyl)(3,5-di-tert-butyl-2-phenoxy)

titanium dichloride, dimethylsilylene(tert-butylcyclopentadienyl)(5-methyl-3-phenyl-2-phenoxy) titanium dichloride, dimethylsilylene(tert-butylcyclopentadienyl)(3-tert-butyldimethylsilyl-5-methyl-2-phenoxy)titanium dichloride, dimethylsilylene(tert-butylcyclopentadienyl)(5-methyl-3-trimethylsilyl-2-phenoxy)titanium dichloride, dimethylsilylene(tert-butylcyclopentadienyl)(3-tert-butyl-5-methoxy-2-phenoxy) titanium dichloride, dimethylsilylene(tert-butylcyclopentadienyl)(3-tert-butyl-5-chloro-2-phenoxy) titanium dichloride, dimethylsilylene(tert-butylcyclopentadienyl)(3,5-diamyl-2-phenoxy)titanium dichloride, dimethylsilylene(tetramethylcyclopentadienyl) (2-phenoxy) titanium dichloride, dimethylsilylene (tetramethylcyclopentadienyl)(3-methyl-2-phenoxy) titanium dichloride, dimethylsilylene(tetramethylcyclopentadienyl)(3,5-dimethyl-2-phenoxy)titanium dichloride, dimethylsilylene(tetramethylcyclopentadienyl) (3-tert-butyl-2-phenoxy)titanium dichloride, dimethylsilylene(tetramethylcyclopentadienyl)(3-tert-butyl-5-methyl-2-phenoxy)titanium dichloride, dimethylsilylene (tetramethylcyclopentadienyl)(3,5-di-tert-butyl-2-phenoxy) titanium dichloride, dimethylsilylene(tetramethylcyclopentadienyl)(5-methyl-3-phenyl-2-phenoxy) titanium dichloride, dimethylsilylene(tetramethylcyclopentadienyl)(3-tert-butyldimethylsilyl-5-methyl-2-phenoxy)titanium dichloride, dimethylsilylene (tetramethylcyclopentadienyl)(5-methyl-3-trimethylsilyl-2-phenoxy)titanium dichloride, dimethylsilylene (tetramethylcyclopentadienyl)(3-tert-butyl-5-methoxy-2-phenoxy)titanium dichloride, dimethylsilylene (tetramethylcyclopentadienyl)(3-tert-butyl-5-chloro-2-phenoxy)titanium dichloride, dimethylsilylene (tetramethylcyclopentadienyl)(3,5-diamyl-2-phenoxy) titanium dichloride, dimethylsilylene (trimethylsilylcyclopentadienyl)(2-phenoxy)titanium dichloride, dimethylsilylene(trimethylsilylcyclopentadienyl)(3-methyl-2-phenoxy)titanium dichloride, dimethylsilylene(trimethylsilylcyclopentadienyl)(3,5-dimethyl-2-phenoxy)titanium dichloride, dimethylsilylene(trimethylsilylcyclopentadienyl)(3-tert-butyl-2-phenoxy)titanium dichloride, dimethylsilylene(trimethylsilylcyclopentadienyl)(3-tert-butyl-5-methyl-2-phenoxy) titanium dichloride, dimethylsilylene (trimethylsilylcyclopentadienyl)(3,5-di-tert-butyl-2-phenoxy)titanium dichloride, dimethylsilylene (trimethylsilylcyclopentadienyl)(5-methyl-3-phenyl-2-phenoxy)titanium dichloride, dimethylsilylene (trimethylsilylcyclopentadienyl)(3-tert-butyldimethylsilyl-5-methyl-2-phenoxy)titanium dichloride, dimethylsilylene (trimethylsilylcyclopentadienyl)(5-methyl-3-trimethylsilyl-2-phenoxy)titanium dichloride, dimethylsilylene (trimethylsilylcyclopentadienyl)(3-tert-butyl-5-methoxy-2-phenoxy)titanium dichloride, dimethylsilylene (trimethylsilylcyclopentadienyl)(3-tert-butyl-5-chloro-2-phenoxy)titanium dichloride, dimethylsilylene (trimethylsilylcyclopentadienyl)(3,5-diamyl-2-phenoxy) titanium dichloride, dimethylsilylene(indenyl)(2-phenoxy) titanium dichloride, dimethylsilylene(indenyl)(3-methyl-2-phenoxy)titanium dichloride, dimethylsilylene(indenyl)(3,5-dimethyl-2-phenoxy)titanium dichloride, dimethylsilylene(indenyl)(3-tert-butyl-2-phenoxy)titanium dichloride, dimethylsilylene(indenyl)(3-tert-butyl-5-methyl-2-phenoxy)titanium dichloride, dimethylsilylene(indenyl) (3,5-di-tert-butyl-2-phenoxy)titanium dichloride, dimethylsilylene(indenyl)(5-methyl-3-phenyl-2-phenoxy) titanium dichloride dimethylsilylene(indenyl)(3-tert-butyldimethylsilyl-5-methyl-2-phenoxy)titanium dichloride, dimethylsilylene(indenyl)(5-methyl-3-trimethylsilyl-2-phenoxy)titanium dichloride, dimethylsilylene(indenyl)(3-tert-butyl-5-methoxy-2-phenoxy)titanium dichloride, dimethylsilylene(indenyl)(3-tert-butyl-5-chloro-2-phenoxy)titanium dichloride, dimethylsilylene(indenyl)(3,5-diamyl-2-phenoxy)titanium dichloride, dimethylsilylene(fluorenyl)(2-phenoxy)titanium dichloride, dimethylsilylene(fluorenyl)(3-methyl-2-phenoxy)titanium dichloride, dimethylsilylene(fluorenyl)(3,5-dimethyl-2-phenoxy)titanium dichloride, dimethylsilylene(fluorenyl)(3-tert-butyl-2-phenoxy) titanium dichloride, dimethylsilylene(fluorenyl)(3-tert-butyl-5-methyl-2-phenoxy) titanium dichloride, dimethylsilylene(fluorenyl)(3,5-di-tert-butyl-2-phenoxy) titanium dichloride, dimethylsilylene(fluorenyl)(5-methyl-3-phenyl-2-phenoxy)titanium dichloride, dimethylsilylene (fluorenyl)(3-tert-butyldimethylsilyl-5-methyl-2-phenoxy) titanium dichloride, dimethylsilylene(fluorenyl)(5-methyl-3-trimethylsilyl-2-phenoxy)titanium dichloride, dimethylsilylene(fluorenyl)(3-tert-butyl-5-methoxy-2-phenoxy)titanium dichloride, dimethylsilylene(fluorenyl)(3-tert-butyl-5-chloro-2-phenoxy)titanium dichloride, dimethylsilylene(fluorenyl)(3,5-diamyl-2-phenoxy)titanium dichloride, dimethylsilylene(tetramethylcyclopentadienyl) (1-naphthox-2-yl)titanium dichloride and the like, and compounds wherein (2-phenoxy) of these compounds is replaces with (3-phenyl-2-phenoxy), (3-trimethylsilyl-2-phenoxy) or (3-tert-butyldimethylsilyl-2-phenoxy), compounds wherein dimethylsilylene of these compounds is replaced with diethylsilylene, diphenylsilylene or dimethoxysilylene, compounds wherein dichloride of these compounds is replaced with difluoride, dibromide, diiodide, dimethyl, diethyl, diisopropyl, bis(dimethylamido), bis(diethylamido), dimethoxide, diethoxide, di-n-butoxide or diisopropoxide. (tert-butylamido)tetramethylcyclopentadienyl-1,2-ethanediyltitanium dichloride, (tert-butylamido) tetramethylcyclopentadienyl-1,2-ethanediyltitanium dimethyl, (tert-butylamido)tetramethylcyclopentadienyl-1, 2-ethanediyltitanium dibenzyl, (methylamido) tetramethylcyclopentadienyl-1,2-ethanediyltitanium dichloride, (ethylamido)tetramethylcyclopentadienyl-1,2-ethanediyltitanium dichloride, (tert-butylamido) tetramethylcyclopentadienyldimethylsilane titanium dichloride, (tert-butylamido)tetramethylcyclopentadienyldimethylsilane titanium dimethyl, (tert-butylamido) tetramethylcyclopentadienyldimethylsilane -titanium dibenzyl, (benzylamido)tetramethylcyclopentadienyl-dimethylsilanetitanium dichloride, (phenylphosphido) tetramethylcyclopentadienyldimethyl -silanetitanium dibenzyl, (tert-butylamido)indenyl-1,2-ethanedlyltitanium dichloride, (tert-butylamido)indenyl-1,2-ethanediyltitanium dimethyl, (tert-butylamido)tetrahydroindenyl-1,2-ethanediyltitanium dichloride, (tert-butylamido) tetrahydroindenyl-1,2-ethanediyltitanium dimethyl, (tert-butylamido)fluorenyl-1,2-ethanediyltitanium dichloride, (tert-butylamido)fluorenyl-1,2-ethanediyltitanium dimethyl, (tert-butylamido)indenyldimethylsilanetitanium dichloride, (tert-butylamido)indenyldimethylsilanetitanium dimethyl, (tert-butylamido)tetrahydroindenyldimethylsilanetitanium dichloride, (tert-butylamido)tetrahydroindenyl- dimethylsilanetitanium dimethyl, (tert-butylamido) fluorenyldimethylsilanetitanium dichloride, (tert-butylamido)fluorenyldimethylsilanetitanium dimethyl, (dimethylaminomethyl)tetramethylcyclopentadienyl-titanium(III) dichloride, (dimethylaminoethyl)

tetramethylcyclopentadienyl-titanium(III) dichloride, (dimethylaminopropyl)tetramethylcyclopentadienyl-titanium(III) dichloride, (N-pyrrolidinylethyl)tetramethylcyclopentadienyl-titanium dichloride, (B-dimethylaminoborabenzene)cyclopentadienylzirconium dichloride, cyclopentadienyl(9-mesitylboraanthracenyl)zirconium dichloride, 2,2'-thiobis[4-methyl-6-(1-methylethyl)phenoxy]titanium dichloride, 2,2'-thiobis(4,6-dimethylphenoxyltitanium dichloride, 2,2'-thiobis(4-methyl-6-tert-butylphenoxy)titanium dichloride, 2,2'-methylenebis(4-methyl-6-tert-butylphenoxy)titanium dichloride, 2,2'-ethylenebis(4-methyl-6-tert-butylphenoxy)titanium dichloride, 2,2'-sulfinylbis(4-methyl-6-tert-butylphenoxy)titanium dichloride, 2,2'-(4,4',6,6'-tetra-tert-butyl-1,1'-biphenoxy)titanium dichloride, 2,2'-thiobis[4-methyl-6-tert-butylphenoxy]titanium diisopropoxide, 2,2'-methylenebis(4-methyl-6-tert-butylphenoxy)titanium diisopropoxide, 2,2'-ethylenebis(4-methyl-6-tert-butylphenoxy)titanium diisopropoxide, 2,2'-sulfinylbis(4-methyl-6-tert-butylphenoxy)titanium diisopropoxide, (di-tert-butyl-1,3-propanediamido)titanium dichloride, (dicyclohexyl-1,3-propanediamido) titanium dichloride, [bis(trimethylsilyl)-1,3-propanediamido]titanium dichloride, [bis(tert-butyldimethylsilyl)-1,3-propanediamido]titanium dichloride, [bis(2,6-dimethylphenyl)-1,3-propanediamido] titanium dichloride, [bis(2,6-diisopropylphenyl)-1,3-propanediamido]titanium dichloride, [bis(2,6-di-tert-butylphenyl)-1,3-propanediamido]titanium dichloride, [bis(triisopropylsilyl)naphthalenediamido]titanium dichloride, [bis(trimethylsilyl)naphthalenediamido]titanium dichloride, [bis(tert-butyldimethylsilyl)naphthalenediamido]titanium dichloride, [bis(tert-butyldimethylsilyl)naphthalenediamido]titanium dibromide, [hydrotris(3,5-dimethylpyrazolyl)borate]titanium trichloride, [hydrotris(3,5-dimethylpyrazolyl)borate] titanium tribromide, [hydrotris(3,5-dimethylpyrazolyl)borate]titanium triiodide, [hydrotris(3,5-diethylpyrazolyl)borate]titanium trichloride, [hydrotris(3,5-diethylpyrazolyl)borate]titanium tribromide, [hydrotris(3,5-diethylpyrazolyl)borate]titanium triiodide, [hydrotris(3,5-di-tert-butylpyrazolyl)borate]titanium trichloride, [hydrotris(3,5-di-tert-butylpyrazolyl)borate]titanium tribromide, [hydrotris(3,5-di-tert-butylpyrazolyl)borate]titanium triiodide, [tris(3,5-dimethylpyrazolyl)methyl]titanium trichloride, [tris(3,5-dimethylpyrazolyl)methyl]titanium tribromide, [tris(3,5-dimethylpyrazolyl)methyl]titanium triiodide, [tris(3,5-diethylpyrazolyl)methyl]titanium trichloride, [tris(3,5-diethylpyrazolyl)methyl]titanium tribromide, [tris (3,5-diethylpyrazolyl)methyl]titanium triiodide, [tris(3,5-di-tert-butylpyrazolyl)methyl]titanium trichloride, [tris(3,5-di-tert-butylpyrazolyl)methyl]titanium tribromide, [tris(3,5-di-tert-butylpyrazolyl)methyl]titanium triiodide and the like, compounds in which titanium of these compounds is replaced with zirconium or hafnium, compounds in which (2-phenoxy) of these compounds is replaced with (3-phenyl-2-phenoxy), (3-trimethylsilyl-2-phenoxy) or (3-tert-butyldimethylsilyl-2-phenoxy), compounds in which dimethylsilylene of these compounds is replaced with diethylsilylene, diphenylsilylene, or dimethoxysilylene, compounds in which dichloride of these compounds is replaced with difluoride, dibromide, diiodide, dimethyl, diethyl, diisopropyl, bis(dimethylamide), bis(diethylamide), dimethoxide, diethoxide, di-n-butoxide, diisopropoxide or bis(diacetoxy) and the like.

Among the metal compounds(II) represented by the general formula [10], specific examples of a compound in which a metal atom is a nickel atom include 2,2'-methylenebis[(4R)-4-phenyl-5,5'-dimethyloxazoline]nickel dichloride, 2,2'-methylenebis[(4R)-4-phenyl-5,5'-dimethyloxazoline] nickel dibromide, 2,2'-methylenebis[(4R)-4-phenyl-5,5'-diethyloxazoline]nickel dichloride, 2,2'-methylenebis[(4R)-4-phenyl-5,5'-diethyloxazoline]nickel dibromide, 2,2'-methylenebis[(4R)-4-phenyl-5,5!-di-n-propyloxazoline] nickel dichloride, 2,2!-methyleneb[(4R)-4-phenyl-5,51-di-n-propyloxazoline]nickel dibromide, 2,2! -methyleneb[(4R)-4-phenyl-5,5'-disopropyloxazoline]nickel dichloride, 2,2'-methyleneb[(4R)-4-phenyl-5,5'-diisopropyloxazoline] nickel dibromide, 2,2'-methyleneb[(4R)-4-phenyl-5,5'-dicyclohexyloxazoline]nickel dichloride, 2,2'-methyleneb[(4R)-4-phenyl-5,5'-dicyclohexyloxazoline]nickel dibromide, 2,2'-methyleneb[(4R)-4-phenyl-5,5'-dimethoxyoxazoline]nickel dichloride, 2,2'-methyleneb[(4R)-4-phenyl-5,5'-dimethoxyoxazoline]nickel dibromide, [(4R)-4-phenyl-5,5'-diethoxyoxazoline]nickel dichloride, 2,2'-methylenebis[(4R)-4-phenyl-5,5'-diethoxyoxazoline]nickel dibromide, 2,2'-methylenebis[(4R)-4-phenyl-5,5'-diphenyloxazoline]nickel dichloride, 2,2'-methylenebis[(4R)-4-phenyl-5,5'-diphenyloxazoline] nickel dibromide, methylenebis[(4R)-4-methyl-5,5'-di-(2-methylphenyl)oxazoline]nickel dibromide, methylenebis[(4R)-4-methyl-5,5'-di-(3-methylphenyl)oxazoline]nickel dibromide, methylenebis[(4R)-4-methyl-5,5'-di-(4-methylphenyl)oxazoline]nickel dibromide, methylenebis[(4R)-4-methyl-5,5'-di-(2-methoxyphenyl)oxazoline]nickel dibromide, methylenebis[(4R)-4-methyl-5,5'-di-(3-methoxyphenyl)oxazoline]nickel dibromide, methylenebis[(4R)-4-methyl-5,5'-di-(4-methoxyphenyl)oxazoline]nickel dibromide, methylenebis[spiro{(4R)-4-methyloxazoline-5,1'-cyclobutane}]nickel dibromide, methylenebis[spiro{(4R)-4-methyloxazoline-5,1'-cyclopentane}]nickel dibromide, methylenebis[spiro{(4R)-4-methyloxazoline-5,1'-cyclohexane}]nickel dibromide, methylenebis[spiro{(4R)-4-methyloxazoline-5,1'-cycloheptane}]nickel dibromide, 2,2'-methylenebis[(4R)-4-isopropyl-5,5-dimethyloxazoline]nickel dibromide, 2,21-methylenebis[(4R)-4-isopropyl-5,5-diethyloxazoline]nickel dibromide, 2,2'-methylenebis[(4R)-4-isopropyl-5,5-di-n-propyloxazoline]nickel dibromide, methylenebis[(4R)-4-isopropyl-5,5-diisopropyloxazoline]nickel dibromide, 2,2'-methylenebis[(4R)-4-isopropyl-5,5-dicyclohexyloxazoline]nickel dibromide, 2,2'-methylenebis[(4R)-4-isopropyl-5,5-diphenyloxazoline]nickel dibromide, 2,2'-methylenebis[(4R)-4-isopropyl-5,5-di-(2-methylphenyl)oxazoline]nickel dibromide, 2,2'-methylenebis[(4R)-4-isopropyl-5,5-di-(3-methylphenyl)oxazoline]nickel dibromide, 2,2'-methylenebis[(4R)-4-isopropyl-5,5-di-(4-methylphenyl)oxazoline]nickel dibromide, 2,2'-methylenebis[(4R)-4-isopropyl-5,5-di-(2-methoxyphenyl)oxazoline]nickel dibromide, 2,2'-methylenebis[(4R)-4-isopropyl-5,5-di-(3-methoxyphenyl)oxazoline]nickel dibromide, 2,2'-methylenebis[(4R)-4-isopropyl-5,5-di-(4-methoxyphenyl)oxazoline]nickel dibromide, 2,2'-methylenebis[spiro{(4R)-4-isopropyloxazoline-5,1'-cyclobutane}]nickel dibromide, 2,2'-methylenebis[spiro{(4R)-4-isopropyloxazoline-5,1'-cyclopentane}]nickel dibromide, 2,2'-methylenebis[spiro{(4R)-4-isopropyloxazoline-5,1'-cyclohexane}]nickel dibromide, 2,2'-methylenebis[spiro{(4R)-4-isopropyloxazoline-5,1'-cycloheptane}]nickel dibromide, 2,2'-methylenebis[(4R)-4-isobutyl-5,5-dimethyloxazoline] nickel dibromide, 2,2'-methylenebis[(4R)-4-isobutyl-5,5-diethyloxazoline]nickel dibromide, 2,2'-methylenebis[(4R)-4-isobutyl-5,5-di-n-propyloxazoline]nickel dibromide, 2,2'-methylenebis[(4R)-4-isobutyl-5,5-diisopropyloxazoline]

nickel dibromide, 2,2'-methylenebis[(4R)-4-isobutyl-5,5-dicyclohexyloxazoline]nickel dibromide, 2,2'-methylenebis[(4R)-4-isobutyl-5,5-diphenyloxazoline]nickel dibromide, 2,2'-methylenebis[(4R)-4-isobutyl-5,5-di-(2-methylphenyl)oxazoline]nickel dibromide, 2,2'-methylenebis[(4R)-4-isobutyl-5,5-di-(3-methylphenyl)oxazoline]nickel dibromide, 2,2'-methylenebis[(4R)-4-isobutyl-5,5-di-(4-methylphenyl)oxazoline]nickel dibromide, 2,2'-methylenebis[(4R)-4-isobutyl-5,5-di-(2-methoxyphenyl)oxazoline]nickel dibromide, 2,2'-methylenebis[(4R)-4-isobutyl-5,5-di-(3-methoxyphenyl)oxazoline]nickel dibromide, 2,2'-methylenebis[(4R)-4-isobutyl-5,5-di-(4-methoxyphenyl)oxazoline]nickel dibromide, 2,2'-methylenebis[spiro{(4R)-4-isobutyloxazoline-5,1'-cyclobutanel}]nickel dibromide, 2,2'-methylenebis[spiro{(4R)-4-isobutyloxazoline-5,1'-cyclopentane}]nickel dibromide, 2,2'-methylenebis[spiro{(4R)-4-isobutyloxazoline-5,1'-cyclohexane}]nickel dibromide, 2,2'-methylenebis[spiro{(4R)-4-isobutyloxazoline-5,1'-cycloheptane}]nickel dibromide, 2,2'-methylenebis[(4R)-4-tert-butyl-5,5-dimethyloxazoline]nickel dibromide, 2,2'-methylenebis[(4R)-4-tert-butyl-5,5-diethyloxazoline]nickel dibromide, 2,2'-methylenebis[(4R)-4-tert-butyl-5,5-di-n-propyloxazoline]nickel dibromide, 2,2'-methylenebis[(4R)-4-tert-butyl-5,5-diisopropyloxazoline]nickel dibromide, 2,2'-methylenebis[(4R)-4-tert-butyl-5,5-diphenyloxazoline]nickel dibromide, 2,2'-methylenebis[(4R)-4-tert-butyl-5,5-dicyclohexyloxazoline]nickel dibromide, 2,2'-methylenebis[(4R)-4-tert-butyl-5,5-di-(2-methylphenyl)oxazoline]nickel dibromide, 2,21-methylenebis[(4R)-4-tert-butyl-5,5-di-(3-methylphenyl)oxazoline]nickel dibromide, 2,2'-methylenebis[(4R)-4-tert-butyl-5,5-di-(4-methylphenyl)oxazoline]nickel dibromide, 2,2'-methylenebis[(4R)-4-tert-butyl-5,5-di-(2-methoxyphenyl)oxazoline]nickel dibromide, 2,2'-methylenebis[(4R)-4-tert-butyl-5,5-di-(3-methoxyphenyl)oxazoline]nickel dibromide, 2,2'-methylenebis[(4R)-4-tert-butyl-5,5-di-(4-methoxyphenyl)oxazoline]nickel dibromide, 2,2'-methylenebis[spiro{(4R)-4-tert-butyloxazoline-5,1'-cyclobutane}]nickel dibromide, 2,2'-methylenebis[spiro{(4R)-4-tert-butyloxazoline-5,1'-cyclopentane}]nickel dibromide, 2,2'-methylenebis[spiro{(4R)-4-tert-butyloxazoline-5,1'-cyclohexane}]nickel dibromide, 2,2'-meth methylenebis[spiro{(4R)-4-phenyloxazoline-5,1'-cyclobutane)}nickel dibromide, 2,2'-methylenebis[spiro{(4R)-4-phenyloxazoline-5,1'-cyclopentane}]nickel dibromide, 2,2'-methylenebis[spiro{(4R)-4-phenyloxazoline-5,1'-cyclohexane}]nickel dibromide, 2,2'-methylenebis[spiro{(4R)-4-phenyloxazoline-5,1'-cycloheptane}]nickel dibromide, 2,2'-methylenebis[(4R)-4-benzyl-5,5-dimethyloxazoline]nickel dibromide, 2,2'-methylenebis[(4R)-4-benzyl-5,5-diethyloxazoline]nickel dibromide, 2,2'-methylenebis[(4R)-4-benzyl-5,5-di-n-propyloxazoline]nickel dibromide, 2,2'-methylenebis[(4R)-4-benzyl-5,5-diisopropyloxazoline]nickel dibromide, 2,2'-methylenebis[(4R)-4-benzyl-5,5-dicyclohexyloxazoline]nickel dibromide, 2,2'-methylenebis[(4R)-4-benzyl-5,5-diphenyl)oxazoline]nickel dibromide, 2,2'-methylenebis[(4R)-4-benzyl-5,5-di-(2-methylphenyl)oxazoline]nickel dibromide, 2,21-methylenebis[(4R)-4-benzyl-5,5-di-(3-methylphenyl)oxazoline]nickel dibromide, 2,2'-methylenebis[(4R)-4-benzyl-5,5-di-(4-methylphenyl)oxazoline]nickel dibromide, 2,2'-methylenebis[(4R)-4-benzyl-5,5-di-(2-methoxyphenyl)oxazoline]nickel dibromide, 2,2'-methylenebis[(4R)-4-benzyl-5,5-di-(3-methoxyphenyl)oxazoline]nickel dibromide, 2,2-methylenebis[(4R)-4-benzyl-5,5-di-(4-methoxyphenyl)oxazoline]nickel dibromide, 2,2'-methylenebis[spiro{(4R)-4-benzyloxazoline-5,1'-cyclobutane}] nickel dibromide, 2,2'-methylenebis[spiro{(4R)-4-benzyloxazoline-5,1'-cyclopentane}]nickel dibromide, 2,2'-methylenebis[spiro{(4R)-4-benzyloxazoline-5,1'-cyclohexane}]nickel dibromide, 2,2'-methylenebis[spiro{(4R)-4-benzyloxazoline-5,1'-cycloheptane}]nickel dibromide, and compounds in which (4R) in each of the above-mentioned compounds corresponds to (4S), etc. Further, examples of the meso type isomer include compounds in which (4R) of two skeletons in each of the compounds which are mentioned above as the optically active substances of bisoxazolines were changed to (4R) of one oxazoline skeleton and (4S) of another oxazoline skeleton, and [hydrotris(3,5-dimethylpyrazolyl)borate]nickel chloride, [hydrotris(3,5-dimethylpyrazolyl)borate]nickel bromide, [hydrotris(3,5-dimethylpyrazolyl)borate]nickel iodide, [hydrotris(3,5-dimethylpyrazolyl)borate]nickel methyl, [hydrotris(3,5-dimethylpyrazolyl)borate]nickel ethyl, [hydrotris (3,5-dimethylpyrazolyl) borate] nickel allyl, [hydrotris(3,5-dimethylpyrazolyl)borate]nickel methallyl, (hydrotris(3,5-diethylpyrazolyl)borate]nickel chloride, [hydrotris(3,5-diethylpyrazolyl)borate]nickel bromide, [hydrotris(3,5-diethylpyrazolyl)borate]nickel iodide, [hydrotris(3,5-diethylpyrazolyl)borate]nickel methyl, [hydrotris(3,5-diethylpyrazolyl)borate]nickel ethyl, [hydrotris(3,5-diethylpyrazolyl)borate]nickel allyl, [hydrotris(3,5-diethylpyrazolyl)borate]nickel methallyl, [hydrotris(3,5-di-tert-butylpyrazolyl)borate]nickel chloride, [hydrotris(3,5-di-tert-butylpyrazolyl)borate]nickel bromide, [hydrotris(3,5-di-tert-butylpyrazolyl)borate]nickel iodide, [hydrotris(3,5-di-tert-butylpyrazolyl)borate]nickel methyl, [hydrotris(3,5-di-tert-butylpyrazolyl)borate]nickel ethyl, [hydrotris(3,5-di-tert-butylpyrazolyl)borate]nickel allyl, [hydrotris(3,5-di-tert-butylpyrazolyl)borate]nickel methallyl, compounds indicated by the structural formula described below:

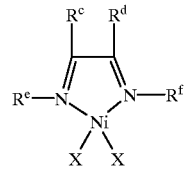

(wherein each of $R^c$ and $R^d$ is a 2,6-diisopropylphenyl group, and X, $R^e$ and $R^f$ are any one of the combination of the substituents represented in Table 1 described below.) $R^9$ and $R^{10}$ may be one bi-valent group (e.g. a acenaphthyl group) in one united body.

TABLE 1

| | | |
|---|---|---|
| $R^e = R^f = H$ | $R^e = R^f$ = methyl | Acenaphthyl by $R^e$ & $R^f$ |
| $X^a = F$ | $X^a = F$ | $X^a = F$ |
| $R^e = R^f = H$ | $R^e = R^f$ = methyl | Acenaphthyl by $R^e$ & $R^f$ |
| $X^a = Cl$ | $X^a = Cl$ | $X^a = Cl$ |
| $R^e = R^f = H$ | $R^e = R^f$ = methyl | Acenaphthyl by $R^e$ & $R^f$ |
| $X^a = I$ | $X^a = I$ | $X^a = I$ |
| $R^e = R^f = H$ | $R^e = R^f$ = methyl | Acenaphthyl by $R^e$ & $R^f$ |
| $X^a$ = Methyl | $X^a$ = methyl | $X^a$ = methyl |
| $R^e = R^f = H$ | $R^e = R^f$ = methyl | Acenaphthyl by $R^e$ & $R^f$ |
| $X^a$ = Ethyl | $X^a$ = ethyl | $X^a$ = ethyl |
| $R^e = R^f = H$ | $R^e = R^f$ = methyl | Acenaphthyl by $R^e$ & $R^f$ |
| $X^e$ = n-propyl | $X^a$ = n-propyl | $X^a$ = n-propyl |
| $R^e = R^f = H$ | $R^e = R^f$ = methyl | Acenaphthyl by $R^e$ & $R^f$ |
| $X^a$ = isopropyl | $X^a$ = isopropyl | $X^a$ = isopropyl |
| $R^e = R^f = H$ | $R^e = R^f$ = methyl | Acenaphthyl by $R^e$ & $R^f$ |
| $X^a$ = n-butyl | $X^a$ = n-butyl | $X^a$ = n-butyl |
| $R^e = R^f = H$ | $R^e = R^f$ = methyl | Acenaphthyl by $R^e$ & $R^f$ |

TABLE 1-continued

| $X^a$ = phenyl<br>$R^e$ = $R^f$ = H<br>$X^a$ = benzyl | $X^a$ = phenyl<br>$R^e$ = $R^f$ = methyl<br>$X^a$ = benzyl | $X^a$ = phenyl<br>Acenaphthyl by $R^e$ & $R^f$<br>$X^a$ = benzyl |
|---|---|---|

Further, compounds wherein a nickel atom is replaced with a palladium atom, a cobalt atom, a rhodium atom or a ruthenium atom can be similarly exemplified in the above-mentioned nickel compounds.

Among the metal compounds(II) represented by the general formula [11], specific examples of a compound in which a transition metal atom is an iron atom include 2,6-bis-[1-(2,6-dimethylphenylimino)ethyl]pyridineiron dichloride, 2,6-bis-[1-(2,6-diisopropylphenylimino)ethyl] pyridineiron dichloride, 2,6-bis-[1-(2-tert-butylphenylimino)ethyl] pyridineiron dichloride, [hydrotris(3,5-dimethylpyrazolyl)borate]iron chloride, [hydrotris(3,5-dimethylpyrazolyl)borate]iron bromide, [hydrotris(3,5-dimethylpyrazolyl)borate]iron iodide, [hydrotris(3,5-dimethylpyrazolyl)borate] iron methyl, [hydrotris(3,5-dimethylpyrazolyl)borate]iron ethyl, [hydrotris(3,5-dimethylpyrazolyl)borate]iron allyl, [hydrotris(3,5-dimethylpyrazolyl)borate]iron methallyl, [hydrotris(3,5-diethylpyrazolyl) borate]iron chloride, [hydrotris(3,5-diethylpyrazolyl)borate]iron bromide, [hydrotris(3,5-diethylpyrazolyl)borate]iron iodide, [hydrotris(3,5-diethylpyrazolyl)borate]iron methyl, [hydrotris(3,5-diethylpyrazolyl)borate]iron ethyl, [hydrotris(3,5-diethylpyrazolyl)borate]iron allyl, [hydrotris(3,5-diethylpyrazolyl)borate]iron methallyl, [hydrotris(3,5-di-tert-butylpyrazolyl)borate]iron chloride, [hydrotris(3,5-di-tert-butylpyrazolyl)borate]iron bromide, [hydrotris(3,5-di-tert-butylpyrazolyl)borate]iron iodide, [hydrotris(3,5-di-tert-butylpyrazolyl)borate]iron methyl, [hydrotris(3,5—di-tert-butylpyrazolyl)borate]iron ethyl, [hydrotris(3,5-di-tert-butylpyrazolyl)borate]iron allyl, [hydrotris(3,5-di-tert-butylpyrazolyl)borate]iron methallyl, and the like.

Further, compounds wherein an iron atom is replaced with a cobalt atom or a nickel atom can be similarly exemplified in the above-mentioned iron compounds.

Moreover, among the metal compounds(II) represented by the general formula [11], specific examples of μ-oxo type compounds include μ-oxobis{isopropylidene (cyclopentadienyl)(2-phenoxy)titanium chloride}, μ-oxobis{isopropylidene(cyclopentadienyl)(2-phenoxy) titanium methoxide}, μ-oxobis{isopropylidene (cyclopentadienyl)(3-tert--butyl-5-methyl-2-phenoxy) titanium chloride}, μ-oxobis{isopropylidene (cyclopentadienyl)(3-tert-butyl-5-methyl-2-phenoxy) titanium methoxide}, μ-oxobis{isopropylidene (methylcyclopentadienyl)(2-phenoxy)titanium chloride}, μ-oxobis{isopropylidene(methylcyclopentadienyl)(2-phenoxy)titanium methoxide}, μ-oxobis{isopropylidene (methylcyclopentadienyl)(3-tert-butyl-5-methyl-2-phenoxy)titanium chloride}, μ-oxobis{isopropylidene (methylcyclopentadienyl)(3-tert-butyl-5-methyl-2-phenoxy)titanium methoxide}, μ-oxobis{isopropylidene (tetramethylcyclopentadienyl)(2-phenoxy)titanium chloride}, μ-oxobis{isopropylidene(tetramethylcyclopentadienyl)(2-phenoxy)titanium methoxide}, μ-oxobis{isopropylidene(tetramethylcyclopentadienyl)(3-tert-butyl-5-methyl-2-phenoxy)titanium chloride}, μ-oxobis{isopropylidene (tetramethylcyclopentadienyl)(3-tert-butyl-5-methyl-2-phenoxy)titanium methoxide}, μoxobis{dimethylsilylene(cyclopentadienyl)(2-phenoxy) titanium chloride}, μoxobis{dimethylsilylene (cyclopentadienyl)(2-phenoxy)titanium methoxide}, μ-oxobis{dimethylsilylene(cyclopentadienyl)(3-tert-butyl-5-methyl-2-phenoxy)titanium chloride}, μ-oxobis{dimethylsilylene(cyclopentadienyl) (3-tert-butyl-5-methyl-2-phenoxy)titanium methoxide}, μ-oxobis{dimethylsilylene(methylcyclopentadienyl) (2-phenoxy)titanium chloride}, μ-oxobis{dimethylsilylene (methylcyclopentadienyl)(2-phenoxy)titanium methoxide}, μ-oxobis{dimethylsilylene(methylcyclopentadienyl)(3-tert-butyl-5-methyl-2-phenoxy)titanium chloride}, μ-oxobis{dimethylsilylene(methylcyclopentadienyl)(3-tert-butyl-5-methyl-2-phenoxy)titanium methoxide}, μ-oxobis{dimethylsilylene (tetramethylcyclopentadienyl) (2-phenoxy)titanium chloride}, μ-oxobis{dimethylsilylene (tetramethylcyclopentadienyl)(2-phenoxy)titanium methoxide}, μ-oxobis{dimethylsilylene(tetramethylcyclopentadienyl) (3-tert-butyl-5-methyl-2-phenoxy) titanium chloride}, μ-oxobis{dimethylsilylene (tetramethylcyclopentadienyl)(3-tert-butyl-5-methyl-2-phenoxy)titanium methoxide} di-μ-oxobis[isopropylidene (cyclopentadienyl)(2-phenoxy)titanium], di-μ-oxobis [isopropylidene(cyclopentadienyl)(3-tert-butyl-5-methyl-2-phenoxy)titanium], di-μ-oxobis[isopropylidene (methylcyclopentadienyl)(2-phenoxy)titanium], di-μ-oxobis [isopropylidene(methylcyclopentadienyl)(3-tert-butyl-5-methyl-2-phenoxy)titanium], di-μ-oxobis[isopropylidene (tetramethylcyclopentadienyl)(2-phenoxy)titanium), di-μ-oxobis isopropylidene (tetramethylcyclopentadienyl)(3-tert-butyl-5-methyl-2-phenoxy)titanium], di-μ-oxobis [dimethylsilylene(cyclopentadienyl)(2-phenoxy)titanium], di-μ-oxobis[dimethylsilylene(cyclopentadienyl)(3-tert-butyl-5-methyl-2-phenoxy)titanium], di-μ-oxobis {dimethylsilylene(methylcyclopentadienyl)(2-phenoxy) titanium), di-μ-oxobis }dimethylsilylene (methylcyclopentadienyl)[(3-tert-butyl-5-methyl-2-phenoxy)titanium], di-9-oxobis[dimethylsilylene (tetramethylcyclopentadienyl) (2-phenoxy)titanium], di-μ-oxobis[dimethylsilylene(tetramethylcyclopentadienyl) (3-tert-butyl-5-methyl-2-phenoxy)titanium] and the like.

Furthermore, compounds in which a titanium atom is replaced with a zirconium atom or a hafnium atom can be similarly exemplified in the above-mentioned titanium compounds.

Specific Examples of the metal compounds(II) other than the metal compounds represented by the general formula [11] and μ-oxo type metal compounds include nickel chloride, nickel bromide, nickel iodide, nickel sulfate as a compound in which metal atom is nickel atom, nickel-nitrate, nickel perchlorate, nickel acetate, nickel trifluoroacetate, nickel cyanide, nickel oxalate, nickel acetylacetonate, bis (allyl) nickel, bis(1,5-cyclooctadiene) nickel, dichloro(1,5-cyclooctadiene) nickel, dichlorobis (acetonitrile)nickel, dichlorobis(benzonitrile)nickel, carbonyl tris(triphenylphosphine)nickel, dichlorobis (triethylphosphine)nickel, di-acetobis (triphenylphosphine) nickel, tetrakis(triphenylphosphine)nickel, dichloro[1,2-bis (diphenylphosphino)ethane]nickel, bis[1,2-bis (diphenylphosphino)ethane]nickel, dichloro[1,3-bis (diphenylphosphino)propane]nickel, bis[1,3-bis (diphenylphosphino)propane]nickel, tetraamine nickel nitrate, tetrakis(acetonitrile)nickel tetrafluoroborate, nickel phthalocyanine, etc.

Among the metal compounds(II), specific examples of a compound in which a transition metal atom is a vanadium atom include vanadium acetylacetonate, vanadium tetrachloride, vanadium oxy trichloride and the like.

Among the metal compounds(II), specific examples of a compound in which a transition metal atom is a samarium atom include bis(pentamethylcyclopentadienyl)samarium methyltetrahydrofuran and the like.

Among the metal compounds(II), specific examples of a compound in which a transition metal atom is an ytterbium atom include bis(pentamethylcyclopentadienyl)ytterbium methyltetrahydrofuran and the like.

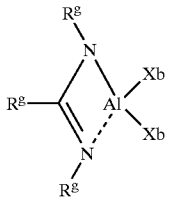

(wherein respective $R^g$ groups independently represent a hydrogen atom, halogen atom or hydrocarbon group, they may be the same or different, and two or more of them may be bonded mutually and may form a ring. Xb groups independently represent a hydrogen atom, halogen atom or hydrocarbon group, they may be the same or different, and may be bonded mutually and may form a ring.)

These metal compounds(II) may be used alone, or in combination of 2 or more kinds of the compounds.

In the metal compounds described above, as a metal compound(II) used in the present invention, compounds represented by the general formula [11] are preferable.

Among these, metal compounds in which M in the general formula [10] is a transition metal are preferable, and further, particularly metal compounds in which L in the general formula [10] is a group having at least one cyclopentadiene type anion skeleton, are preferable.

(III) Organoaluminum Compound

As the organoaluminum compound (III) which is a component used for the catalyst for addition polymerization of the present invention, known organoaluminum compounds can be used. The organoaluminum compound indicated by the general formula [13] described below is preferable.

 [13]

(wherein Rh represents a hydrocarbon group, all of Rhis may be the same or different. Z represents a hydrogen atom, a halogen atom, an alkoxy group, an aralkyloxy group or an aryloxy group, and "b" represents a numeral satisfying $0<b\leq 3$.)

$R^h$ in the general formula [13] representing the organoaluminum compound is preferably a hydrocarbon group having 1 to 24 carbon atoms, and more preferably an alkyl group having 1 to 24 carbon atoms. Specific examples include a methyl group, an ethyl group, a n-propyl group, a n-butyl group, an isobutyl group, a n-hexyl group, a 2-methylhexyl group, a n-octyl group and the like, and an ethyl group, a n-butyl group, an isobutyl group or a n-hexyl group is preferable.

Further, specific example of a case in which Z is a halogen atom includes a fluorine atom, a chlorine atom, a bromine atom, an iodine atom, and a chlorine atom is preferable.

The alkoxy group in Z is preferably an alkoxy group having 1 to 24 carbon atoms, and specific examples include a methoxy group, an ethoxy group, a n-propoxy group, an isopropoxy group, a n-butoxy group, a sec-butoxy group, a tert-butoxy group, a n-pentoxy group, a neopentoxy group, a n-hexoxy group, a n-octoxy group, a n-dodecoxy group, a n-pentadecoxy group, a n-icosoxy -group and the like, and a methoxy group, an ethoxy group or a tert-butoxy group is preferable.

Any one of these alkoxy groups may be substituted with a halogen atom such as a fluorine atom, a chlorine atom, a bromine atom or an iodine atom, an alkoxy group such as a methoxy group, an ethoxy group or the like, or an aryloxy group such as a phenoxy group or the like.

The aryloxy group in Y is preferably an aryloxy group having 6 to 24 carbon atoms, and specific examples include a phenoxy group, a 2-methylphenoxy group, a 3-methyl phenoxy group, a 4-methylphenoxy group, a 2,3-dimethyl phenoxy group, a 2,4-dimethylphenoxy group, a 2,5-dimethylphenoxy group, a 2,6-dimethylphenoxy group, a 3,4-dimethylphenoxy group, a 3,5-dimethylphenoxy group, a 2,3,4-trimethylphenoxy group, a 2,3,5-trimethylphenoxy group, a 2,3,6-trimethylphenoxy group, a 2,4,5-trimethylphenoxy group, a 2,4,6-trimethylphenoxy group, a 3,4,5-trimethylphenoxy group, a 2,3,4,5-tetramethylphenoxy group, a 2,3,4,6-tetramethylphenoxy group, 2,3,5,6-tetramethylphenoxy group, a pentamethylphenoxy group, an ethylphenoxy group, a n-propylphenoxy group, an isopropylphenoxy group, a n-butylphenoxy group, a sec-butylphenoxy group, a tert-butylphenoxy group, a n-hexylphenoxy group, a n-octylphenoxy group, a n-decylphenoxy group, a n-tetradecylphenoxy group, a naphthoxy group, an anthrathenoxy group and the like.

Any one of these aryloxy groups may be substituted with a halogen atom such as a fluorine atom, a chlorine atom, a bromine atom, an iodine atom or the like, an alkoxy group such as a methoxy group, an ethoxy group or the like, or an aryloxy group such as a phenoxy group or the like.

The aralkyloxy group in Y is preferably an aralkyloxy group having 7 to 24 carbon atoms, and specific examples include a benzyloxy group, a (2-methylphenyl)methoxy group, a (3-methylphenyl)methoxy group, a (4-methylphenyl)methoxy group, a (2,3-dimethylphenyl) methoxy group, a (2,4-dimethylphenyl)methoxy group, a (2,5-dimethylphenyl)methoxy group, a (2,6-dimethylphenyl)methoxy group, a (3,4-dimethylphenyl) methoxy group, a (3,5-dimethylphenyl)methoxy group, a (2,3,4-trimethylphenyl)methoxy group, a (2,3,5-trimethylphenyl)methoxy group, a (2,3,6-trimethylphenyl) methoxy group, a (2,4,5-trimethylphenyl)methoxy group, a (2,4,6-trimethylphenyl)methoxy group, a (3,4,5-trimethylphenyl)methoxy group, a (2,3,4,5-tetramethylphenyl)methoxy group, a (2,3,4,6-tetramethylphenyl)methoxy group, a (2,3,5,6-tetramethylphenyl)methoxy group, a (pentamethylphenyl) methoxy group, an (ethylphenyl)methoxy group, a (n-propylphenyl)methoxy group, an (isopropylphenyl) methoxy group, a (n-butylphenyl)methoxy group, a (sec-butylphenyl)methoxy group, a (tert-butylphenyl)methoxy group, a (n-hexylphenyl)methoxy group, a (n-octylphenyl) methoxy group, a (n-decylphenyl)methoxy group, a (n-tetradecylphenyl)methoxy group, a naphthylmethoxy group, an anthrathenylmethoxy group and the like, and a benzyloxy group is preferable.

Any one of these aralkyloxy groups may be substituted with a halogen atom such as a fluorine atom, a chlorine atom, a bromine atom, an iodine atom or the like, an alkoxy group such as a methoxy group, an ethoxy group or the like, or an aryloxy group such as a phenoxy group or the like.

Specific examples of the organoaluminum compound represented by the general formula (13) include trialkylaluminums such as trimethylaluminum, triethylaluminum, tri-n-propylaluminum, tri-n-butylaluminum, triisobutylaluminum, tri-n-hexylaluminum, tri-n-octylaluminum and the like; dialkylaluminum chlorides such as dimethylaluminum chloride, diethylaluminum chloride, di-n-propylaluminum chloride, di-n-butylaluminum chloride, diisobutylaluminum chloride, di-n-hexylaluminum chloride and the like; alkylaluminum dichlorides such as methylaluminum dichloride, ethylaluminum dichloride, n-propylaluminum dichloride, n-butylaluminum dichloride, isobutylaluminum dichloride, n-hexylaluminum dichloride and the like; dialkylaluminum hydrides such as dimethylaluminum hydride, diethylaluminum hydride, di-n-propylaluminum hydride, di-n-butylaluminum hydride, diisobutylaluminum hydride, di-n-hexylaluminum hydride and the like, alkyl(dialkoxy) aluminums such as methyl(dimethoxy)aluminum, methyl (diethoxy)aluminum, methyl(di-tert-butoxy)aluminum and the like; dialkyl(alkoxy)aluminums such as dimethyl (methoxy) aluminum, dimethyl(ethoxy) aluminum, dimethyl(tert-butoxy)aluminum and the like; alkyl (diaryloxy)aluminums such as methyl(diphenoxy) aluminum, methylbis(2,6-diisopropylphenoxy)aluminum, methylbis(2,6-diphenylphenoxy)aluminum and the like; dialkyl(aryloxy)aluminums such as dimethyl(phenoxy) aluminum, dimethyl(2,6-diisopropylphenoxy)aluminum, dimethyl(2,6-diphenylphenoxy)aluminum and the like, etc.

Among these, a trialkylaluminum is preferable, and trimethylaluminum, triethylaluminum, tri-n-butylaluminum, triisobutylaluminum or tri-n-hexylaluminum, is more preferable, and in particular, triisobutylaluminum or tri-n-hexylaluminum is preferable.

These organoaluminum compounds may be used alone, or in combination of two or more.

The ratio (molar ratio) of the amount used of the respective catalyst components in the present invention is not particularly limited, and the molar ratio of the component (I) to the component (II) is usually a molar ratio of a range of (I) (II)=from 1:1 to 10000:1, preferably from 1:1 to 5000:1, and more preferably a molar ratio of a range of from 1:1 to 1000:1. The amount used in case of using the component (III) is usually a molar ratio of a range of (II) (III)=from 0.1:1 to 1:10000, and preferably a molar ratio of a range of from 1:1 to 1:1000.

As the catalyst for addition polymerization of the present invention, a reaction product obtained by preliminarily contacting the component (I) and the component (II), optionally, further the component (III) may be also used, and they may be also used by being separately charged in a polymerization vessel. The arbitrary two components among them may be also previously contacted, and further, another component may be also contacted.

When the respective components are used as a solution, the concentration of the component (I) and the component (III) are usually 0.0001 to 100 mmol/L converted to metal atom, and preferably 0.01 to 10 mmol/L, respectively. The concentration of the component (II) is usually 0.0001 to 100 mmol/L converted to metal atom, and preferably 0.01 to 10 mmol/L.

The method of feeding the respective components in a reactor is not particularly limited. A method of feeding the respective components in a solid condition, a method of feeding them in a condition of a solution in which they are dissolved in a hydrocarbon solvent from which components such as moisture, oxygen and the like deactivating catalyst components are removed, or a suspension or a slurry, and the like are mentioned.

Concerning the polymerization method, it should not be specifically limited. For example, there are mentioned a solvent polymerization or a slurry polymerization in which an aliphatic hydrocarbon such as butane, pentane, hexane, heptane, octane or the like; an aromatic hydrocarbon such as benzene, toluene or the like; or a halogenated hydrocarbon such as methylene dichloride or the like is used as a solvent, a bulk polymerization in which polymerization is carried out in a liquid monomer, a gas phase polymerization in which polymerization is carried out in a gaseous monomer, a high-pressure polymerization method in which polymerization is carried out in a supercritical liquid condition at a high temperature under a high pressure, etc. As polymerization form, either of a batch-wise type and a continuous type are possible.

The polymerization temperature is usually from $-100°$ C. to $350°$ C., preferably from $-20°$ C. to $30°$ C., and more preferably from $20°$ C. to $300°$ C. The polymerization pressure is usually from 1 to 3500 kg/cm$^2$G, preferably from 1 to 3000 kg/cm$^2$G, and more preferably from 1 to 2000 kg/cm$^2$G. In general, the polymerization time is appropriately determined according to the kind of a desired polymer and a reaction apparatus, and a range of form 1 minute to 20 hours can be adopted.

As monomers which can be used, any one of olefins having 2 to 100 carbon atoms, diolefins, cyclic olefins, alkenyl aromatic hydrocarbons and polar monomers can be used, and two or more monomers thereof can also be used, simultaneously. Specific examples thereof include olefins such as ethylene, propylene, 1-butene, 1-pentene, 4-methyl-1-pentene-1,2-methyl-1-hexene, 1-hexene, 1-heptene, 1-octene, 1-nonene, 1-decene, vinylcyclohexene and the like; diolefins such as 1,5-hexadiene, 1,4-hexadiene, 1,4-pentadiene, 1,7-octadiene, 1,8-nonadiene, 1,9-decadiene, 4-methyl-1,4-hexadiene, 5-methyl-1,4-hexadiene, 7-methyl-1,6-octadiene, 5-ethylidene-2-norbornene, dicyclopentadiene, 5-vinyl-2-norbornene, 5-methyl-2-norbornene, norbornadiene, 5-methylene-2-norbornene, 1,5-cyclooctadiene, 5,8-endomethylenehexahydronaphthalene, 1,3-butadiene, isoprene, 1,3-hexadiene, 1,3-octadiene, 1,3-cyclooctadiene, 1,3-cyclohexadiene and the like; cyclic olefins such as norbornene, 5-methylnorbornene, 5-ethylnorbornene, 5-butylnorbornene, 5-phenylnorbornene, 5-benzylnorbornene, tetracyclododecene, tricyclodecene, tricycloundecene, pentacyclopentadecene, pentacyclohexadecene, 8-methyltetracyclododecene, 8-ethyltetracyclododecene, 5-acetylnorbornene, 5-acetyloxynorbornene, 5-methoxycarbonylnorbornene, 5-ethoxycarbonylnorbornene, 5-methyl-5-methoxycarbonylnorbornene, 5-cyanonorbornene, 8-methoxycarbonyltetracyclododecene, 8-methyl-8-tetracyclododecene, 8-cyanotetracyclododecene and the like; alkenylbenzenes such as styrene, 2-phenylpropylene, 2-phenylbutene, 3-phenylpropylene and the like; alkylstyrenes such as p-methylstyrene, m-methylstyrene, o-methylstyrene, p-ethylstyrene, m-ethylstyrene, o-ethylstyrene, 2,4-dimethylstyrene, 2,5-dimethylstyrene, 3,4-dimethylstyrene, 3,5-dimethylstyrene, 3-methyl-5-ethylstyrene, p-tert-butylstyrene, p-sec-butylstyrene and the like; bis(alkenyl)benzenes such as divinylbenzene and the like; alkenyl aromatic hydrocarbons such as alkenylnaphthalenes and the like such as 1-vinylnaphthalene and the like; polar monomers such as α,β-unsaturated carboxylic acids such as acrylic acid, methacrylic acid, fumaric acid, maleic anhydride, itaconic acid, itaconic anhydride, bicyclo (2,2,1)-5-heptene-2,3-dicarboxylic acid and the like, and metal salts thereof such as sodium, potassium, lithium, zinc, magnesium, calcium and the like; α,β-unsaturated carboxylic acid esters such as methyl acrylate, ethyl acrylate, n-propyl acrylate, isopropyl acrylate, tert-butyl acrylate, 2-ethylhexyl acrylate, methyl methacrylate, ethyl methacrylate, n-propyl methacrylate, isopropyl methacrylate, n-butyl methacrylate, isobutyl methacrylate and the like; unsaturated dicarboxylic acids such as maleic acid, itaconic acid and the like; vinyl esters such as vinyl acetate, vinyl propionate, vinyl capronate, vinyl caprate, vinyl laurate, vinyl stearate, vinyl trifluoroacetate and the like; unsaturated carboxylic acid glycidylate such as acrylic acid glycidylate, methacrylic acid glycidylate, itaconic acid monoglycidylate and the like; etc.

The present invention can be applied to homopolymerzation or copolymerzation of these monomers. Specific examples of the monomer constituting the copolymer include ethylene and propylene, ethylene and 1-butene, ethylene and 1-hexene, propylene and 1-butene, and the like, but the present invention should not be limited thereto.

In order to control the molecular weight of a polymer, a chain transfer agent such as hydrogen or the like can be added.

The catalyst for addition polymerization of the present invention is particularly suitable as a catalyst for olefin polymerization, and suitably used for a production process of an olefin polymer. The olefin polymer is preferably a copolymer of ethylene with an t-olefin in particular, and specifically, a linear low density polyethylene (LLDPE) is preferable. Further, a propylene polymer is preferably as the olefin polymer in particular

EXAMPLE

The present invention is further illustrated in detail according to Examples and Comparative Examples below, but the present invention is not limited thereto.

The measurement values of respective items in Examples were measured according to methods described below.
(1) The content of α-olefin unit in a copolymer was determined by using a calibration curve from the characteristic absorption of ethylene and α-olefin using an infrared spectrometer (FT-IR7300, manufactured by NIPPON BUNKO Inc.) and was represented as a short-chain branch (SCB) number per 1000 carbon atoms.
(2) Intrinsic viscosity ([η]):
It was measured at 135° C. in a tetralin solution using an Ubbelohde viscometer.
(3) Measurement of $^{13}$C-NMR
JNM-EX270 (67.5 MHz, $^{13}$C) of Nihon Denshi Company was used for measuring $^{13}$C-NMR. A deuterated solvent described in Example was used and measurement was carried out at room temperature.
(4) Molecular weight and molecular weight distribution:
They were determined under the under-mentioned conditions according to a gel permeation chromatography (GPC). Calibration curve was prepared using a standard polystyrene. Molecular weight distribution was evaluated by a ratio (Mw/Mn) of weight average molecular weight (Mw) to number average molecular weight (Mn).
Equipment: 150° C. type, manufactured by Milipore Waters Co., Ltd.
Column: TSK-GEL GMH-HT; 7.5×600×2 columns
Measurement temperature: 140° C.
Solvent: O-dichlorobenzene
Measurement concentration: 5 mg/5 ml
(5) Melting point of a copolymer was determined using SSC-5200 of Seiko Co., Ltd. according to the condition below.
Raise of temperature: 40° C. to 150° C.(10° C./min.), retaining for 5 minutes.
Cooling: 150° C. to 40° C.(5° C./min.),
retaining for 10 minutes.
Measurement: 40° C. to 160° C.(5° C./min.)

Example 1

(1) Synthesis of compound (I-1)
Into a 200 ml four-necked flask in which the atmosphere was replaced with argon, 10 ml (10 mmol) of ZnEt$_2$ (diethylzinc) (1.02M, hexane solution) and 50 ml of toluene were charged and the mixture was cooled to −78° C. Thereto, 5.7 ml (10 mmol) of pentafluorophenol (1.78M, hexane solution) was added dropwise. After completion of dropwise addition, temperature was gradually raised to room temperature, and stirring was further carried out for 2 hours. Then, 89.0 mg (4.94 mmol) of H$_2$O was gradually added dropwise by a micro syringe at room temperature. The content became muddy in white. After completion of dropwise addition, stirring was further carried out for 11 hours. The white gel solid prepared was dried at room temperature under reduced pressure to obtain 2.56 g of a white powder. As a result of measurements of $^1$H-NMR and $^{13}$C-NMR, a spectrum according to an unreacted Zn-Et structure was confirmed.

$^1$H-NMR (THF-d8): δ 1.18 (t,3H, J=7.9 Hz, ZnCH$_2$CH$_3$), 0.28 (q,2H, J=7.9 Hz, ZnCH$_2$CH$_3$)

$^{13}$C-NMR(THF-d8): δ 141.9 (m), 141.4 (m, JC-F=233 Hz), 139.0 (m, JC-F=245 Hz), 131.7 (m, JC-F=236 Hz), 12.5 (s, ZnCH$_2$CH$_3$), −3.0 (s, ZnCH$_2$CH$_3$)
(2) Polymerization After drying under vacuum an autoclave reactor having an inner volume of 400 ml equipped with a stirrer and replacing the atmosphere thereof with argon, 190 ml of hexane as a solvent and 10 ml of 1-hexene as a comonomer were charged and the reactor was heated to 70° C. After the raise of temperature, ethylene was fed while adjusting at an ethylene pressure of 6 kg/cm$^2$. After the system was stabilized, 0.25 mmol of triisobutylaluminum was charged, successively, 1.0 μmol of ethylenebis (indenyl) zirconium dichloride was charged, 22.1 mg (86.2 μmol-Zn) of the component (I-1) obtained in the above-mentioned (1) was further charged, and polymerization was started. The polymerization was carried out for 30 minutes. As a result of the polymerization, 7.88 g of an ethylene-1-hexene copolymer was obtained. Polymerization activity was 1.6×10$^7$ g/mol/h. SCB=13.73, [η]=1.24 dl/g, Mw=79000, Mw/Mn=1.7.

Example 2

(1) Synthesis of compound (I-2)
Into a 200 ml four-necked flask in which the atmosphere was replaced with argon, 10 ml (10 mmol) of ZnEt$_2$ (1.02M, hexane solution) and 50 ml of toluene were charged and the mixture was cooled to −78° C. Thereto, 6.9 ml (10 mmol) of pentafluorophenol (1.48M, hexane solution) was added dropwise. After completion of dropwise addition, temperature was gradually raised to room temperature, and stirring was further carried out over night. Then, stirring was carried out for one hour under reflux condition, and the mixture was cooled to room temperature. Then, 93.8 mg (5.21 mmol) of H$_2$O was gradually added dropwise by a micro syringe. The content became white slurry-like. After completion of dropwise addition, stirring was carried out for 6 hours under reflux condition. Volatile materials were removed by distillation under reduced pressure from the white slurry product prepared, and the solid prepared was dried at room temperature under reduced pressure to obtain 2.21 g of a white powder.

(2) Polymerization

After drying under vacuum an autoclave reactor having an inner volume of 400 ml equipped with a stirrer and replacing the atmosphere thereof with argon, 190 ml of hexane as a solvent and 10 ml of 1-hexene as a comonomer were charged and the reactor was heated to 70° C. After the raise of temperature, ethylene was fed while adjusting at an ethylene pressure of 6 kg/cm$^2$. After the system was stabilized, 0.25 mmol of triisobutylaluminum was charged, and successively, 1.0 μmol of ethylenebis(indenyl) zirconium dichloride was charged, 23.4 mg (91.2 μmol-Zn) of the compound (I-2) obtained in the above-mentioned (1) was further charged, and polymerization was started. The polymerization was carried out for 30 minutes. As a result of the polymerization, 8.69 g of an ethylene-1-hexene copolymer was obtained. Polymerization activity was $1.7 \times 10^7$ g/mol/h. SCB=16.46, [θ]=1.33 dl/g, Mw=77000, Mw/Mn=2.0.

Example 3

(1) Synthesis of compound (I-3)

Into a 200 ml four-necked flask in which the atmosphere was replaced with argon after reduced pressure drying under vacuum, 10 ml (10 mmol) of a hexane solution of diethylzinc [1.02 mol/L (M)] and 50 ml of tetrahydrofuran were charged, and the mixture was cooled to −78° C. and stirred. Thereto, 6.9 ml (10 mmol) of pentafluorophenol (1.48M, hexane solution) was added dropwise. After completion of dropwise addition the temperature was gradually raised to room temperature, and stirring was carried out for 2 hours. Then, 93.7 mg (5.20 mmol) of H$_2$O was gradually added dropwise by a micro syringe. The content became a yellow transparent solution. After completion of dropwise addition, stirring was carried out for 20 hours. Volatile materials were removed by distillation under reduced pressure, and the solid prepared was dried at 120° C. for 8 hours under reduced pressure to obtain 2.34 g of an ivory powder. As a result of measurements of $^1$H-NMR and $^{13}$C-NMR, a spectrum derived from a Zn-Et structure could not be confirmed.

$^{13}$C-NMR(THF-d8): δ 141.9(m), 141.4 (m, JC-F=234 Hz), 139.0 (m, JC-F=249 Hz), 131.6 (m, JC-F=236 Hz)

(2) Polymerization

After drying under vacuum an autoclave reactor having an inner volume of 400 ml equipped with a stirrer and replacing the atmosphere thereof with argon, 190 ml of hexane as a solvent and 10 ml of 1-hexene as a comonomer were charged and the reactor was heated to 70° C. After the raise of temperature, ethylene was fed while adjusting at an ethylene pressure of 6 kg/cm$^2$. After the system was stabilized, 0.25 mmol of triisobutylaluminum was charged, successively, 1.0 μmol of ethylenebis(indenyl)zirconium dichloride was charged, 31.4 mg (122 μmol-Zn) of the compound (I-3) obtained in the above-mentioned (1) was further charged, and polymerization was started. The polymerization was carried out for 30 minutes. As a result of the polymerization, 15.75 g of an ethylene-1-hexene copolymer was obtained. Polymerization activity was $3.2 \times 10^7$ g/mol/h. SCB=15.23, [η]=1.24 dl/g, Mw=72000, Mw/Mn=2.0.

Example 4

(1) Synthesis of compound (I-4)

Into a 200 ml four-necked flask in which the atmosphere was replaced with argon after reduced pressure drying under vacuum, 20 ml (20 mmol) of a hexane solution of diethylzinc (1.02M) and 100 ml of tetrahydrofuran were charged, and the mixture was cooled to −78° C. and stirred. Thereto, 4.4 ml (5.1 mmol) of pentafluorophenol (1.17M, hexane solution) was added dropwise. After completion of dropwise addition, the temperature was gradually raised to room temperature, and stirring was carried out for 2 hours. Then, 321 μl (17.8 mmol) of H$_2$O was gradually added dropwise by a micro syringe. After completion of dropwise addition, stirring was carried out for 14 hours. Volatile materials were removed by distillation under reduced pressure, and the solid prepared was dried at 120° C. for 8 hours under reduced pressure to obtain an ivory powder.

(2) Polymerization

After drying under vacuum an autoclave reactor having an inner volume of 400 ml equipped with a stirrer and replacing the atmosphere thereof with argon, 190 ml of hexane as a solvent and 10 ml of 1-hexene as a comonomer were charged and the reactor was heated to 70° C. After the raise of temperature, ethylene was fed while adjusting at an ethylene pressure of 6 kg/cm$^2$. After the inside of system was stabilized, 0.25 mmol of triisobutylaluminum was charged, successively, 0.3 μmol of ethylenebis(indenyl) zirconium dichloride was charged, 9.0 mg (72 μmol-Zn) of the compound (I-4) obtained in the above-mentioned (1) was further charged, and polymerization was started. The polymerization was carried out for 30 minutes. As a result of the polymerization, 2.4 g of an ethylene-hexene-1 copolymer was obtained Polymerization activity was $1.6 \times 10^7$ g/mol/h. SCB=15.54.

Example 5

(1) Synthesis of compound (I-5)

Into a 200 ml four-necked flask in which the atmosphere was replaced with argon after reduced pressure drying under vacuum, 20 ml (20 mmol) of a hexane solution of diethylzinc (1.02 M) and 10 ml of tetrahydrofuran were charged, and the mixture was cooled to −78° C. and stirred. Thereto, 8.7 ml (10 mmol) of pentafluorophenol (1.17M, hexane solution) was added dropwise. After completion of dropwise addition, the temperature was gradually raised to room temperature, and stirring was carried out for 2 hours. Then, 275 μl (15.3 mmol) of H$_2$O was gradually added dropwise by a micro syringe. After completion of dropwise addition, stirring was carried out at room temperature over night. Volatile materials were removed by distillation under reduced pressure, and the solid prepared was dried at 12° C. for 8 hours under reduced pressure to obtain an ivory powder.

(2) Polymerization

After drying under vacuum an autoclave having an inner volume of 400 ml equipped with a stirrer and replacing the atmosphere thereof with argon, 190 ml of hexane as a solvent and 10 ml of 1-hexene as a comonomer were charged and the reactor was heated to 70° C. After the raise of temperature, ethylene was fed while adjusting at an ethylene pressure of 6 kg/cm$^2$. After the inside of system was stabilized, 0.25 mmol of triisobutylaluminum was charged, successively, 0.3 μmol of ethylenebis(indenyl) zirconium dichloride was charged, 9.3 mg (55 μmol-Zn) of the compound (I-5) obtained in the above-mentioned (1) was further charged, and polymerization was started. The polymerization was carried out for 30 minutes. As a result of the polymerization, 11.06 g of an ethylene-1-hexene copolymer was obtained. Polymerization activity was $7.4 \times 10^7$ g/mol/h. SCB=12.79.

Example 6

(1) Polymerization

After drying under vacuum an autoclave reactor having an inner volume of 400 ml equipped with a stirrer and replacing the atmosphere thereof with argon, 190 ml of hexane as a solvent and 10 ml of 1-hexene as a comonomer were charged and the reactor was heated to 70° C. After the raise of temperature, ethylene was fed while adjusting at an ethylene pressure of 6 kg/cm$^2$. After the system was stabilized, 0.25 mmol of triisobutylaluminum was charged, successively, 0.3 µmol of ethylenebis(indenyl) zirconium dichloride was charged, 23.2 mg (90.5 µmol-Zn) of the compound (I-3) obtained in Example 3(1) was further charged, and polymerization was started. The polymerization was carried out for 30 minutes. As a result of the polymerization, 6.9 g of an ethylene-1-hexene copolymer was obtained. Polymerization activity was 4.6×10$^7$ g/mol/h. SCB=15.39.

Example 7
(1) Synthesis of compound (I-6)

Into a 200 ml four-necked flask in which the atmosphere was replaced with argon after reduced pressure drying under vacuum, 20 ml (20 mmol) of a hexane solution of diethylzinc (1.02M) and 100 ml of tetrahydrofuran were charged, and the mixture was cooled to −78° C. and stirred. Thereto, 26.2 ml (30.7 mmol) of pentafluorophenol (1.17M, hexane solution) was added dropwise. After completion of dropwise addition, the temperature was gradually raised to room temperature, and stirring was carried out for 2 hours. Then, 92 µl (5.1 mmol) of H$_2$O was gradually added dropwise by a micro syringe. After completion of dropwise addition, stirring was carried out at room temperature over night. Volatile materials were removed by distillation under reduced pressure, and the solid prepared was dried at 120° C. for 8 hours under reduced pressure to obtain an ivory powder.

(2) Polymerization

After drying under vacuum an autoclave having an inner volume of 400 ml equipped with a stirrer and replacing the atmosphere thereof with argon, 190 ml of hexane as a solvent and 10 ml of 1-hexene as a comonomer were charged and the reactor was heated to 70° C. After the raise of temperature, ethylene was fed while adjusting at an ethylene pressure of 6 kg/cm$^2$. After the inside of system was stabilized, 0.25 mmol of triisobutylaluminum was charged, successively, 0.39 mol of ethylenebis(indenyl) zirconium dichloride was charged, 27.0 mg (78.5 µmol-Zn) of the compound (I-6) obtained in the above-mentioned (1) was further charged, and polymerization was started. The polymerization was carried out for 30 minutes. As a result of the polymerization, 1.3 g of an ethylene-hexene-1 copolymer was obtained. Polymerization activity was 8.7×10$^6$ g/mol/h. SCB=17.04.

Example 8
(1) Polymerization of propylene

A magnetic stirrer was placed in an autoclave having an inner volume of 100 ml, it was dried under vacuum, and the atmosphere was replaced with argon. Thereto, 70.6 mg (275 µmol-Zn) of the compound (I-2) obtained in Example 2(1), 0.5 mmol of triisobutylaluminum and 2 µmol of ethylenebis (indenyl)zirconium dichloride were charged. In the autoclave, 40 g of propylene was charged, temperature was raised to 40° C., and polymerization was started. The polymerization was carried out for 60 minutes. As a result of the polymerization, 2.23 g of a propylene polymer was obtained. Polymerization activity was 2.2×10$^6$ g/mol/h. Mw=21000, Mw/Mn=1.9.

Example 9
(1) Synthesis of Compound (I-7)

Into a 300 ml four-necked flask in which the atmosphere was replaced with argon after reduced pressure drying under vacuum, 16.49 g (90.07 mmol) of pentafluoroaniline and 70 ml of toluene were charged, and the mixture was cooled to 0° C. and stirred. Thereto, 176.6 ml of diethylzinc (1.02M, hexane solution) was added, then the temperature was gradually raised to room temperature, and stirring was carried out over night. The content article became a white slurry. After stirring was carried out for 8 hours under reflux condition, volatile materials were removed by distillation under reduced pressure to obtain 18.32 g of a solid product.

After drying the solid product under reduced pressure in vacuum, 3.68 g of the solid product and 100 ml of toluene were charged in the 300 ml four-necked flask in which the atmosphere was replaced with argon, and the mixture was stirred at room temperature. Thereto, 17.0 ml (19.9 mmol) of pentafluorophenol (1.17M, hexane solution) was added, and stirring was carried out for 68 hours. Volatile materials were removed by distillation under reduced pressure to obtain a white solid.

(2) Polymerization

After drying under vacuum an autoclave having an inner volume of 400 ml equipped with a stirrer and replacing the atmosphere thereof with argon, 190 ml of hexane as a solvent and 10 ml of 1-hexene as a comonomer were charged and the reactor was heated to 70° C. After the raise of temperature, ethylene was fed while adjusting at an ethylene pressure of 6 kg/cm$^2$. After the inside of system was stabilized, 0.25 mmol of triisobutylaluminum was charged, successively, 1 µmol of ethylenebis(indenyl) zirconium dichloride was charged, 40.8 mg (120 µmol-Zn) of the compound (I-7) obtained in the above-mentioned (1) was further charged, and polymerization was started. The polymerization was carried out for 30 minutes. As a result of the polymerization, 1.02 g of an ethylene-1-hexene copolymer was obtained. Polymerization activity was 2.0×10$^6$ g/mol/h.

Example 10

Into a 300 ml four-necked flask in which the atmosphere was replaced with argon, 106 ml of tetrahydrofuran and 40 ml (80 mmol) of ZnEt$_2$ (2M, hexane solution) were charged, and the mixture was cooled to 4° C. Thereto, 14.5 ml (32 mmol) of pentafluorophenol (2.21M, tetrahydrofuran solution) was added dropwise for 50 minutes. After completion of dropwise addition, stirring was further carried out at 50° C. for 1 hour. The temperature was lowered to 20° C. by ice bath, and 7.3 ml (72.3 mmol) of H$_2$O (9.9M, tetrahydrofuran solution) was added dropwise for 1 hour. After completion of dropwise addition, stirring was further carried out for 2 hours, then the mixture was stood alone at room temperature over night. Then, stirring was carried out for 8 hours under reflux condition (63° C.). As a result, the component (A) was obtained as an yellow transparent solution.

Example 11

Into a 200 ml four-necked flask in which the atmosphere was replaced with argon, 40 ml of tetrahydrofuran and 40 ml (80 mmol) of ZnEt$_2$ (2M, hexane solution) were charged, and the mixture was cooled to 500. Thereto, 34.3 ml (80 mmol) of 3,4,5-trifluorophenol (2.33M, tetrahydrofuran solution) was added dropwise for 120 minutes. After completion of dropwise addition, stirring was carried out at 5° C. for 90 minutes and then, further at 40° C. for 70 minutes. Then, the temperature was lowered to 20° C. by ice bath, and 0.72 ml (40 mmol) of H$_2$O was added dropwise for 80 minutes. After completion of dropwise addition, stirring was carried out at 200° C. for 60 minutes and then, further, at 40° C. for 120 minutes. As a result, the mixture was separated into a transparent liquid article and an yellow gel article. After standing them alone at room temperature over night, the volatile components were removed by distillation, and drying was carried out at 120° C. for 8 hours under reduced pressure. As a result, 17.05 g of an yellow solid product was obtained.

Example 12

Into a 200 ml four-necked flask in which the atmosphere was replaced with argon, 40 ml of tetrahydrofuran and 40 ml (80 mmol) of $ZnEt_2$ (2M, hexane solution) were charged, and the mixture was cooled to 50° C. Thereto, 13.7 ml (32 mmol) of 3,4,5-trifluorophenol (2.33M, tetrahydrofuran solution) was added dropwise for 45 minutes. After completion of dropwise addition, stirring was carried out at 5° C. for 90 minutes and then, further at 40° C. for 70 minutes. Then, the temperature was lowered to 20° C. by ice bath, and 1.30 ml (72 mmol) of $H_2O$ was added dropwise for 145 minutes. After completion of dropwise addition, stirring was carried out at 20° C. for 60 minutes and then, further, at 40° C. for 120 minutes. As a result, the mixture was separated into a transparent liquid article and an yellow gel article. After standing them alone at room temperature over night, the volatile components were removed by distillation, and drying was carried out at 120° C. for 8 hours under reduced pressure. As a result, 10.39 g of an yellow solid product was obtained.

Example 13

Into a 200 ml four-necked flask in which the atmosphere was replaced with argon, 40 ml of tetrahydrofuran and 40 ml (80 mmol) of $ZnEt_2$ (2M, hexane solution) were charged, and the mixture was cooled to 5° C. Thereto, 34.3 ml (80 mmol) of 3,5-difluorophenol (2.33M, tetrahydrofuran solution) was added dropwise for 120 minutes. After completion of dropwise addition, stirring was carried out at 5° C. for 90 minutes and then, further at 40° C. for 70 minutes. Then, the temperature was lowered to 20° C. by ice bath, and 0.72 ml (40 mmol) of $H_2O$ was added dropwise for 80 minutes. After completion of dropwise addition, stirring was carried out at 20° C. for 60 minutes and then, further, at 40° C. for 120 minutes. As a result, a white yellow slurry article was obtained. After standing it alone at room temperature over night, the volatile components were removed by distillation, and drying was carried out at 120° C. for 8 hours under reduced pressure. As a result, 14.66 g of an yellow solid product was obtained.

Example 14

Into a 200 ml four-necked flask in which the atmosphere was replaced with argon, 40 ml of tetrahydrofuran and 40 ml (80 mmol) of $ZnEt_2$ (2M, hexane solution) were charged, and the mixture was cooled to 5° C. Thereto, 34.3 ml (80 mmol) of perfluoro-tert-butanol (2.33M, tetrahydrofuran solution) was added dropwise for 120 minutes. After completion of dropwise addition, stirring was carried out at 5° C. for 90 minutes and then, further at 40° C. for 70 minutes. Then, the temperature was lowered to 20° C. by ice bath, and 0.72 ml (40 mmol) of $H_2O$ was added dropwise for 80 minutes. After completion of dropwise addition, stirring was carried out at 20° C. for 60 minutes and then, further, at 40° C. for 120 minutes. As a result, a white yellow solution was obtained. After standing it alone at room temperature over night, the volatile components were removed by distillation, and drying was carried out at 120° C. for 8 hours under reduced pressure. As a result, 26.35 g of an yellow solid product was obtained.

Example 15

Into a 200 ml four-necked flask in which the atmosphere was replaced with argon, 40 ml of tetrahydrofuran and 40 ml (80 mmol) of $ZnEt_2$ (2M, hexane solution) were charged, and the mixture was cooled to 5° C. Thereto, 34.3 ml (80 mmol) of 1,1,1,3,3,3-hexafluoro-2-propanol (2.33M, tetrahydrofuran solution) was added dropwise for 120 minutes. After completion of dropwise addition, stirring was carried out at 5° C. for 90 minutes and then, further at 40° C. for 70 minutes. Then, the temperature was lowered to 20° C. by ice bath, and 0.72 ml (40 mmol) of $H_2O$ was added dropwise for 80 minutes. After completion of dropwise addition, stirring was carried out at 20° C. for 60 minutes and then, further, at 40° C. for 120 minutes. As a result, a white yellow solution was obtained. After standing it alone at room temperature over night, the volatile components were removed by distillation, and drying was carried out at 120° C. for 8 hours under reduced pressure. As a result, 15.47 g of an yellow solid product was obtained.

Comparative Example 1

(1) Polymerization

After drying under vacuum an autoclave having an inner volume of 400 ml equipped with a stirrer and replacing the atmosphere thereof with argon, 190 ml of hexane as a solvent and 10 ml of 1-hexene as a comonomer were charged and the reactor was heated to 70° C. After the raise of temperature, ethylene was fed while adjusting at an ethylene pressure of 6 kg/cm$^2$. After the inside of system was stabilized, 0.25 mmol of triisobutylaluminum was charged, successively, 1.01 mol of ethylenebis(indenyl) zirconium dichloride was charged, 0.1 ml (100 mol) of $ZnEt_2$ (1.02M, hexane solution) was further charged, and polymerization was started. The polymerization was carried out for 30 minutes. As a result of the polymerization, only a trace of a polymer was obtained.

Example 16

(1) Synthesis of $\mu$-oxo-bis(diethylzinc)

Into a 200 ml four-necked flask in which the atmosphere was replaced with argon after reduced pressure drying under vacuum, 10 ml (10 mmol) of a hexane solution of diethylzinc (1.02 mol/L) and 50 ml of toluene were charged and the mixture was stirred. Thereto, 89.2 mg (4.95 mmol) of $H_2O$ was gradually added dropwise at room temperature.

The content article became opaque in yellow in accordance with proceeding of the reaction. After completion of dropwise addition, stirring was further carried out for 11 hours. The solvent was removed by distillation under reduced pressure, and drying was carried out to obtain 0.245 g of an yellow solid.

(2) Polymerization

After drying under vacuum an autoclave having an inner volume of 400 ml equipped with a stirrer and replacing the atmosphere thereof with argon, 190 ml of hexane as a solvent and 10 ml of 1-hexene as a comonomer were charged and the reactor was heated to 70° C. After the raise of temperature, ethylene was fed while adjusting at an ethylene pressure of 6 kg/cm$^2$. After the inside of system was stabilized, 0.25 mmol of triisobutylaluminum was charged, successively, 1.0, mol of ethylenebis(indenyl) zirconium dichloride was charged, 29.9 mg (146 $\mu$mol) of 9-oxo-bis(diethylzinc) obtained in the above-mentioned (1)

was further charged, and polymerization was started. The polymerization was carried out for 30 minutes. As a result of the polymerization, 0.663 g of an ethylene-1-hexene copolymer was obtained. Polymerization activity was $1.3\times10^6$ g/mol/h. SCB=13.96, [θ]=1.30 dl/g, Mw=88000, Mw/Mn= 1.9.

Example 17

(1) Synthesis of bis(pentafluorophenoxy)zinc

Into a 200 ml four-necked flask in which the atmosphere was replaced with argon after reduced pressure drying under vacuum, 50 ml of hexane and 10 ml (10 mmol) of a hexane solution of diethylzinc (1.00 mol/L) were charged and the mixture was cooled to −78° C. Thereto, 20 ml (20 mmol) of a hexane solution (1.0 mol/L) of pentafluorophenol was gradually added dropwise at room temperature. The content article became white slurry in accordance with proceeding of the reaction. After completion of dropwise addition, the temperature was gradually raised to room temperature, and stirring was further carried out for 4 hours. The white solid prepared was separated by filtration with a glass filter, and drying was carried out under reduced pressure to obtain 3.41 g (7.90 mmol, 79%) of bis(pentafluorophenoxy)zinc as a white solid.

$^{13}$C-NMR (THF-d8): δ 141.4 (m, JC-F=233 Hz), 141.8 (m), 139.0 (m, JC-F=249 Hz), 131.7 (m, JC-F=236 Hz)

(2) Polymerization

After drying under vacuum an autoclave having an inner volume of 400 ml equipped with a stirrer and replacing the atmosphere thereof with argon, 190 ml of hexane as a solvent and 10 ml of 1-hexene as a comonomer were charged and the reactor was heated to 70° C. After the raise of temperature, ethylene was fed while adjusting at an ethylene pressure of 6 kg/cm$^2$. After the inside of system was stabilized, 0.25 mmol of triisobutylaluminum was charged, successively, 1.0 μmol of ethylenebis(indenyl) zirconium dichloride was charged, 40 mg (92 μmol) of the zinc compound obtained in the above-mentioned (1) was further charged, and polymerization was started. The polymerization was carried out for 30 minutes. As a result of the polymerization, 1.35 g of an ethylene-1-hexene copolymer was obtained. Polymerization activity was $2.7\times10^6$ g/mol/h. SCB=16.8, [θ]=1.41 dl/g, Mw 97000, Mw/Mn=2.2. Melting point was 111.5° C.

Example 18

(1) Synthesis of bis(pentafluorophenoxyzincoxy) methylborane compound

Into a 200 ml four-necked flask in which the atmosphere was replaced with argon, 655.4 mg (10.6 mmol) of methylboric acid (97%) and 50 ml of toluene were charged and the mixture was cooled to −78° C. While vigorously stirring the slurry article, 20.8 ml (21.2 mmol) of ZnEt$_2$ (1.02M, hexane solution) was added dropwise. A white gel precipitate was prepared in accordance with increase of the amount of dropwise addition. After completion of dropwise addition, the temperature was gradually raised to room temperature, and stirring was further carried out for 2 hours. Thereto, 11.9 ml (21.2 mmol) of pentafluorophenol (1.78M, hexane solution) was gradually added dropwise, and stirring was further carried out for 11 hours. The solvent was removed by distillation under reduced pressure, and drying was carried out to obtain 6.06 g of a white powder.

(2) Polymerization

After drying under vacuum an autoclave having an inner volume of 400 ml equipped with a stirrer and replacing the atmosphere thereof with argon, 190 ml of hexane as a solvent and 10 ml of 1-hexene as a comonomer were charged and the reactor was heated to 70° C. After the raise of temperature, ethylene was fed while adjusting at an ethylene pressure of 6 kg/cm$^2$. After the inside of system was stabilized, 0.25 mmol of triisobutylaluminum was charged, successively, 1.0% mol of ethylenebis(indenyl) zirconium dichloride was charged, 34.2 mg (61.7 μmol) of the zinc compound obtained in the above-mentioned (1) was further charged, and polymerization was started. The polymerization was carried out for 30 minutes. As a result of the polymerization, 3.42 g of an ethylene-1-hexene copolymer was obtained. Polymerization activity was $6.8\times10^6$ g/mol/h.

Example 19

(1) Synthesis of compound (I-8)

Into a 100 ml flask in which the atmosphere was replaced with argon, 18.3 ml (18.7 mmol) of diethylzinc (1.02M, hexane solution) and 10 ml of toluene were charged and the mixture was cooled to −78° C. Thereto, 10.5 ml (18.7 mmol) of pentafluorophenol (1.78M, hexane solution) was gradually added dropwise. After completion of dropwise addition, temperature was gradually raised to room temperature, and stirring was further carried out for 1 hour. Then, 10 ml of a toluene solution of 1.01 g (9.36 mmol) of 1,3-cyclopentanediol (a mixture of cis-isomer and trans-isomer; manufactured by Aldrich Co., Ltd.; purity=95%) was gradually added dropwise at room temperature, and stirring was carried out over night. Then, the solvent was removed by distillation under reduced pressure, and the solid prepared was dried at room temperature under reduced pressure to obtain 5.44 g of the compound (I-8).

(2) Polymerization

After drying under vacuum an autoclave having an inner volume of 400 ml equipped with a stirrer and replacing the atmosphere thereof with argon, 190 ml of hexane as a solvent and 10 ml of 1-hexene as a comonomer were charged and the reactor was heated to 70° C. After the raise of temperature, ethylene was fed while adjusting at an ethylene pressure of 6 kg/cm$^2$. After the inside of system was stabilized, 0.25 mmol of triisobutylaluminum was charged, successively, 1.0 μmol of ethylenebis(indenyl) zirconium dichloride was charged, 36.3 mg (122 μmol-Zn) of the compound (I-8) obtained in the above-mentioned (1) was further charged, and polymerization was started. The polymerization was carried out for 30 minutes. As a result of the polymerization, 0.53 g of an ethylene-1-hexene copolymer was obtained. Polymerization activity was $1.1\times10^6$ g/mol/h.

Example 20

(1) Synthesis of compound (I-9)

Into a 100 ml flask in which the atmosphere was replaced with argon, 1.01 g (8.04 mmol) of 1,2,3-trihydroxybenzene and 30 ml of toluene were charged, and the mixture was stirred and cooled to 0° C. Thereto, 15.8 ml (16.1 mmol) of diethylzinc (1.02M, hexane solution) was added dropwise. After completion of dropwise addition, temperature was gradually raised to room temperature, and stirring was further carried out for 24 hours. Thereto, 4.0 ml (8.0 mmol) of pentafluorophenol (2M, toluene solution) was added dropwise at room temperature. After completion of dropwise addition, and stirring was further carried out over night. Then, volatile materials were removed by distillation, and the solid prepared was dried at room temperature under reduced pressure to obtain the compound (I-9).

(2) Polymerization

After drying under vacuum an autoclave having an inner volume of 400 ml equipped with a stirrer and replacing the atmosphere thereof with argon, 190 ml of hexane as a solvent and 10 ml of 1-hexene as a comonomer were charged and the reactor was heated to 70° C. After the raise of temperature, ethylene was fed while adjusting at an ethylene pressure of 6 kg/cm². After the inside of system was stabilized, 0.25 mmol of triisobutylaluminum was charged, successively, 1.0 µmol of ethylenebis(indenyl) zirconium dichloride was charged, 26.0 mg (11 µmol-Zn) of the compound (I-9) obtained in the above-mentioned (1) was further charged, and polymerization was started. The polymerization was carried out for 30 minutes. As a result of the polymerization, 0.24 g of an ethylene-1-hexene copolymer was obtained. Polymerization activity was $4.8 \times 10^5$ g/mol/h.

Example 21

(1) Synthesis of compound (I-10)

Into a 100 ml flask in which the atmosphere was replaced with argon, 1.02 g (8.07 mmol) of 1,2,3-trihydroxybenzene and 30 ml of toluene were charged, and the mixture was stirred and cooled to oOC. Thereto, 23.7 ml (24.2 mmol) of diethylzinc (1.02M, hexane solution) was added dropwise. After completion of dropwise addition, temperature was gradually raised to room temperature, and stirring was further carried out for 24 hours. Thereto, 12.1 ml (24.2 mmol) of pentafluorophenol (2M, toluene solution) was added dropwise at room temperature. After completion of dropwise addition, and stirring was further carried out over night. Then, volatile materials were removed by distillation, and the solid prepared was dried at room temperature under reduced pressure to obtain 7.89 g of the compound (I-10).

(2) Polymerization

After drying under vacuum an autoclave having an inner volume of 400 ml equipped with a stirrer and replacing the atmosphere thereof with argon, 190 ml of hexane as a solvent and 10 ml of 1-hexene as a comonomer were charged and the reactor was heated to 70° C. After the raise of temperature, ethylene was fed while adjusting at an ethylene pressure of 6 kg/cm². After the inside of system was stabilized, 0.25 mmol of triisobutylaluminum was charged, successively, 1.0% mol of ethylenebis(indenyl) zirconium dichloride was charged, 38.6 mg (133 µmol-Zn) of the compound (I-10) obtained in the above-mentioned (1) was further charged, and polymerization was started. The polymerization was carried out for 30 minutes. As a result of the polymerization, 0.13 g of an ethylene-1-hexene copolymer was obtained. Polymerization activity was $2.6 \times 10^5$ g/mol/h.

Example 22

(1) Synthesis of Compound (I-11)

Into a 100 ml flask in which the atmosphere was replaced with argon, 8.0 ml (8.2 mmol) of diethylzinc (1.02M, hexane solution) and 10 ml of toluene were charged, and the mixture was stirred and cooled to −78° C. Thereto, 4.6 ml (8.2 mmol) of pentafluorophenol (1.78M, toluene solution) was gradually added dropwise. After completion of dropwise addition, temperature was gradually raised to room temperature, and stirring was further carried out for 1 hour. Then, 0.97 g (2.0 mmol) of calix[4]arene (89%) (manufactured by aldrich Co,) (2M, toluene solution) was added, and stirring was carried out over night. Then, volatile materials were removed by distillation, and the solid prepared was dried at room temperature under reduced pressure to obtain 2.52 g of the compound (I-11).

(2) Polymerization

After drying under vacuum an autoclave having an inner volume of 400 ml equipped with a stirrer and replacing the atmosphere thereof with argon, 190 ml of hexane as a solvent and 10 ml of 1-hexene as a comonomer were charged and the reactor was heated to 70° C. After the raise of temperature, ethylene was fed while adjusting at an ethylene pressure of 6 kg/cm². After the inside of system was stabilized, 0.25 mmol of triisobutylaluminum was charged, successively, 1.0/1 mol of ethylenebis(indenyl) zirconium dichloride was charged, 41.2 mg (117 µmol-Zn) of the compound (I-11) obtained in the above-mentioned (1) was further charged, and polymerization was started. The polymerization was carried out for 30 minutes. As a result of the polymerization, 0.084 g of an ethylene-hexene-1 copolymer was obtained. Polymerization activity was $1.7 \times 10^5$ g/mol/h.

As described above in detail, according to the present invention, a compound other than a compound of Group XIII as a compound capable of forming a catalyst for addition polymerization which reveals a high polymerization activity by using as a catalyst aid component for activation, is provided, and a production method of the compound, a catalyst component for addition polymerization comprising the compound, a catalyst for addition polymerization which is made by using the compound and reveals a high polymerization activity, and an efficient process for producing an olefin polymer using the catalyst for addition polymerization, are provided.

What is claimed is:

1. An electron withdrawing group-containing metal compound (I) selected from the group consisting of [A] to [E] described below:

[A] A compound obtained by contacting (a), (b) and (c) described below in the presence of an ether compound as a solvent:
(a) a compound represented by the general formula [1], $$M^1L^1C \qquad [1]$$

(b) a compound represented by the general formula [2]

$$R^1_{p-1}T^1H \qquad [2], \text{ and}$$

(c) a compound represented by the general formula [3]

$$R^2_{q-2}T^1H_2 \qquad [3]$$

wherein in each of the general formulae [1] to [3], $M^1$ represents an atom of the Group III to the Group XII or lanthanide series of the Periodic Table; c represents a valence of $M^1$; $L^1$ represents a hydrogen atom, a halogen atom or a hydrocarbon group; when a plural number of $L^1$'s exist, they may be mutually the same or different; $R^1$ represents an electron-withdrawing group or a group containing an electron-withdrawing group; $R^2$ represents a hydrocarbon group or a halogenated hydrocarbon group; when a plural number of $R^2$'s exist, they may be mutually the same or different; each of $T^1$ and $J^1$ independently represents an atom of Group XV or Group XVI of the Periodic Table; and each of p and q represents a valence of $T^1$ and $J^1$, respectively;

[B] A compound obtained by contacting (d), (e) and (f) described below:
(d) a compound represented by the general formula [4]

$$M^2L^2d \qquad [4]$$

(e) a compound represented by the general formula [5]

$$R^3_{r-1}T^2H \qquad [5] \text{ and}$$

(f) a compound represented by the general formula [6]

$$R^4(J^2H_{e-1})_f \quad [6]$$

wherein in each of the general formulae [4] to [6], $M^2$ represents an atom of Group III to Group XII or lanthanide series of the Periodic Table; d represents a valence of $M^2$; $L^2$ represents a hydrogen atom, a halogen atom or a hydrocarbon group; when a plural number of $L^2$'s exist, they may be mutually the same or different; $R^3$ represents an electron-withdrawing group or a group containing an electron-withdrawing group; $R^4$ represents an organic group having a valence of f; each of $T^2$ and $J^2$ independently represents an atom of the Group XV or Group XVI of the Periodic Table; r represents a valence of $T^2$; e represents a valence of $J^2$; and f is an integer of 2 to 10;

[C] A compound represented by the general formula [7]

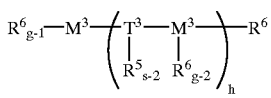  [7]

wherein $M^3$ represents an atom of the Group III to Group XII or lanthanide series of the Periodic Table; when a plural number of $M^3$'s exist, they may be mutually the same or different; $T^3$ represents an atom of the Group XIV, Group XV or Group XVI of the Periodic Table; when a plural number of $T^3$'s exist, they may be mutually the same or different; $R^5$ represents an electron-withdrawing group or a group containing an electron-withdrawing group; when a plural number of $R^5$'s exist, they may be mutually the same or different; $R^6$ represents a hydrocarbon group; a plural number of $R^6$'s may be mutually the same or different; g represents a valence of $M^3$; s represents a valence of $T^3$; and h represents a numeral of 1 or more;

[D] A compound represented by the general formula [8], $$M^4(X^1R^7_i)_t R^8_{j-t} \quad [8]$$

wherein $M^4$ represents an atom of the Group III to Group XII or lanthanide series of the Periodic Table; $X^1$ represents an atom of the Group XIV, Group XV or Group XVI of the Periodic Table; when a plural number of $X^1$'s exist, they may be mutually the same or different; $R^7$ represents an electron-withdrawing group or a group containing an electron-withdrawing group; when a plural number of $R^7$'s exist, they may be mutually the same or different; $R^8$ represents a hydrogen atom, a halogen atom or a hydrocarbon group; a plural number of $R^8$'s may be mutually the same or different; j represents a valence of $M^4$; t represents a numeral satisfying $0<t\leq j$; and i represents a numeral less by one than the valence of $X^1$; and

[E] A compound represented by the general formula [9]

$$[(R^9_{u-1}X^2)k_{-1}\,M^5O]_m\,T^4R^{10}_{3-m} \quad [9]$$

wherein $M^5$ represents an atom of the Group III to Group XII or lanthanide series of the Periodic Table; when a plural number of $M^5$'s exist, they may be mutually the same or different; $X^2$ represents an atom of the Group XIV, Group XV or Group XVI of the Periodic Table; when a plural number of $X^2$'s exist, they may be mutually the same or different; $R^9$ represents an electron-withdrawing group or a group containing an electron-withdrawing group; when a plural number of $R^9$'s exist, they may be mutually the same or different; $T^4$ represents an atom of the Group XIII of the Periodic Table, $R^{10}$ represents a hydrogen atom, a halogen atom or a hydrocarbon group; when a plural number of $R^{10}$'s exist, they may be mutually the same or different; k represents a valence of $M^5$; u represents a valence of $X^2$; and m represents a numeral satisfying $1\leq m\leq 3$.

2. The compound according to claim 1, wherein each of $T^1$, $T^2$, $T^3$, $X^1$ and $X^2$ is independently a nitrogen atom or an oxygen atom.

3. The compound according to claim 1, wherein each of $R^1$, $R^3$, $R^5$, $R^7$ and $R^9$ is independently a halogenated hydrocarbon group.

4. The compound according to claim 2, wherein each of $R^1$, $R^3$, $R^5$, $R^7$ and $R^9$ is independently a halogenated hydrocarbon group.

5. The compound according to claim 1, wherein each of $M^1$, $M^2$, $M^3$, $M^4$ and $M^5$ is independently an atom of the Group XII.

6. The compound according to claim 1, wherein each of $T^1$, $T^2$, $T^3$, $X^1$ and $X^2$ is independently a nitrogen atom or an oxygen atom and each of $M^1$, $M^2$, $M^3$, $M^4$ and $M^5$ is independently an atom of the Group XII.

7. The compound according to claim 5, wherein said atom of the Group XII is zinc.

8. The compound according to claim 6, wherein said atom of the Group XII is zinc.

9. The compound according to claim 1, wherein $T^4$ in the general formula [9] is a boron atom.

10. The compound according to claim 1, wherein $X^1R^7_i$ is a fluoroalkyloxy group or a fluoroaryloxy group in the general formula [8].

11. The compound according to claim 1, wherein the compound [C] is a $\mu$-oxo-bis(alkylzinc) or a $\mu$-oxo-bis(arylzinc).

* * * * *